(12) United States Patent
Tang-Schomer

(10) Patent No.: US 11,291,840 B2
(45) Date of Patent: Apr. 5, 2022

(54) NEURONAL STIMULATION MODEL, DEVICE AND METHODS USING ALTERNATE CURRENT

(71) Applicant: Min Tang-Schomer, Marlborough, CT (US)

(72) Inventor: Min Tang-Schomer, Marlborough, CT (US)

(*) Notice: Subject to any disclaimer, the term of this patent is extended or adjusted under 35 U.S.C. 154(b) by 0 days.

(21) Appl. No.: 16/154,843

(22) Filed: Oct. 9, 2018

(65) Prior Publication Data
US 2019/0105498 A1 Apr. 11, 2019

Related U.S. Application Data

(60) Provisional application No. 62/627,966, filed on Feb. 8, 2018, provisional application No. 62/569,696, filed on Oct. 9, 2017.

(51) Int. Cl.
| | | |
|---|---|---|
| *A61N 1/36* | (2006.01) | |
| *A61N 1/05* | (2006.01) | |
| *A61N 5/06* | (2006.01) | |
| *A61B 90/00* | (2016.01) | |
| *G16H 50/50* | (2018.01) | |

(Continued)

(52) U.S. Cl.
CPC .......... *A61N 1/36082* (2013.01); *A61B 90/37* (2016.02); *A61N 1/0534* (2013.01); *A61N 1/36146* (2013.01); *A61N 5/0622* (2013.01); *C12M 21/08* (2013.01); *C12M 35/02* (2013.01); *C12N 13/00* (2013.01); *G16H 50/50* (2018.01)

(58) Field of Classification Search
CPC .............. A61N 1/0534; A61N 1/36082; A61N 1/36146; A61N 5/0622; C12N 13/00; C12M 21/08; C12M 35/02; A61B 90/37; G16H 50/50
USPC ...................................................... 607/2, 45
See application file for complete search history.

(56) References Cited

U.S. PATENT DOCUMENTS

| | | | |
|---|---|---|---|
| 9,605,253 B2* | 3/2017 | Voldman ................ | A61N 1/205 |
| 2005/0181502 A1* | 8/2005 | Furcht .................. | C12N 5/0607 |
| | | | 435/354 |

(Continued)

OTHER PUBLICATIONS

Koppes, Abigail N., Angela M. Seggio, and Deanna M. Thompson. "Neurite outgrowth is significantly increased by the simultaneous presentation of Schwann cells and moderate exogenous electric fields." Journal of neural engineering 8.4 (2011): 046023. (Year: 2011).*

(Continued)

*Primary Examiner* — Carl H Layno
*Assistant Examiner* — Jane C Kalinock
(74) *Attorney, Agent, or Firm* — Cantor Colburn LLP

(57) ABSTRACT

The present disclosure relates generally to models and methods to modulate neuronal network activities simulating normal brain functions or neurological disorders in culture by applying alternating electric field. The electric field has alternating polarity and changing frequencies to achieve neuronal synchrony. The present disclosure also provides method of modulating modulate directed growth of neuronal axon by applying an alternating field electrical signal. The present disclosure also provides methods of screening compounds using the disclosed models, kits and systems thereof.

Figure 7A:
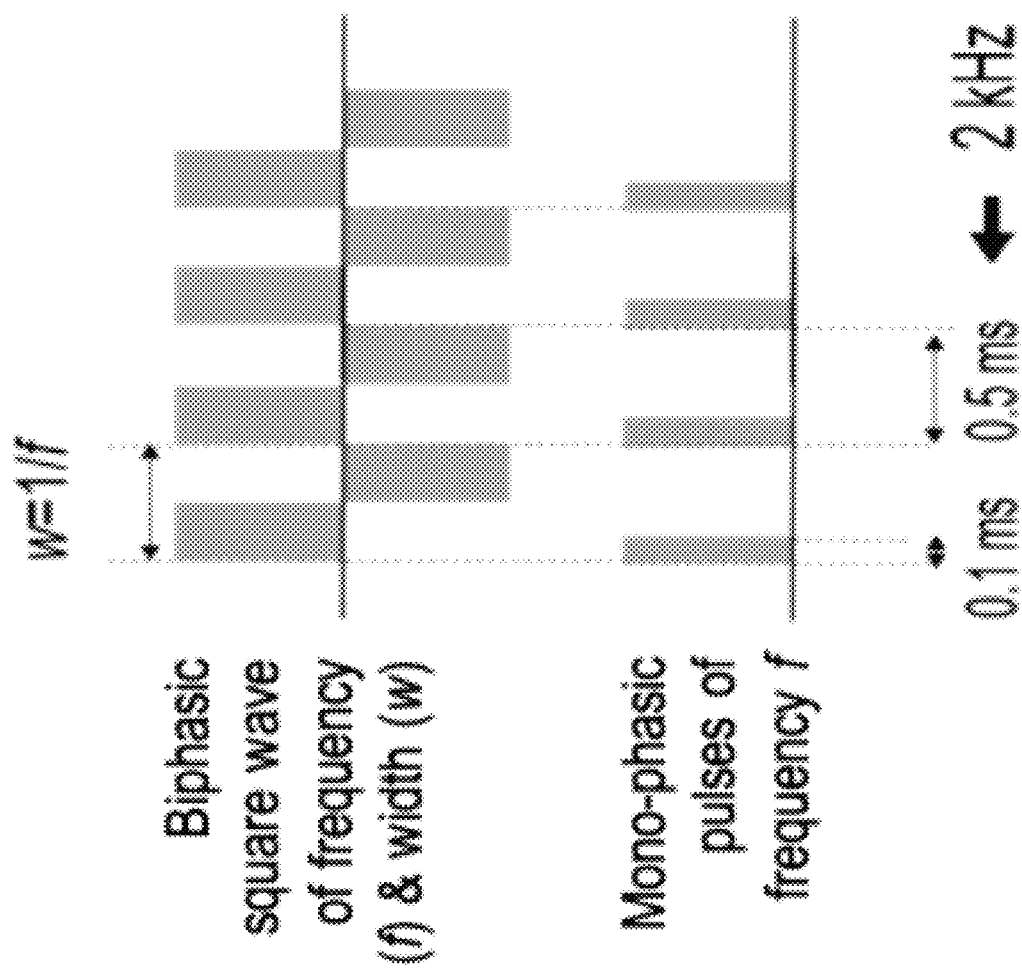

19 Claims, 30 Drawing Sheets
(22 of 30 Drawing Sheet(s) Filed in Color)

(51) Int. Cl.
C12M 1/42 (2006.01)
C12M 3/00 (2006.01)
C12N 13/00 (2006.01)

(56) References Cited

U.S. PATENT DOCUMENTS

2016/0312171 A1* 10/2016 Narkilahti .............. C12M 35/08
2020/0071648 A1* 3/2020 Moore ..................... A61N 1/08

OTHER PUBLICATIONS

Aurand, Emily, et al. "Building biocompatible hydrogels for tissue engineering of the brain and spinal cord." Journal of functional biomaterials 3.4 (2012): 839-863.
Bagley, Elena E., et al. "Short-term field stimulation mimics synaptic maturation of hippocampal synapses." The Journal of physiology 590.7 (2012): 1641-1654.
Balkowiec, et al. "Cellular mechanisms regulating activity-dependent release of native brain-derived neurotrophic factor from hippocampal neurons." Journal of Neuroscience 22.23 (2002): 10399-10407.
Bakkum, et al. "Long-term activity-dependent plasticity of action potential propagation delay and amplitude in cortical networks." PLOS one 3.5 (2008): e2088.
Bakkum, Douglas J., et al. "Spatio-temporal electrical stimuli shape behavior of an embodied cortical network in a goal-directed learning task." Journal of neural engineering 5.3 (2008): 310-323.
Barros, Claudia S., et al. "Extracellular matrix: Functions in the nervous system. Cold Spring Harb Perspect Biol doi."(2011).
Bassett, Danielle S., et al. "Robust detection of dynamic community structure in networks." Chaos: An Interdisciplinary Journal of Nonlinear Science 23.1 (2013): 013142.
Bestmann, et al. "Understanding the behavioural consequences of noninvasive brain stimulation." Trends in cognitive sciences 19.1 (2015): 13-20.
Bikson, Marom, et al. "Effects of uniform extracellular DC electric fields on excitability in rat hippocampal slices in vitro." The Journal of physiology 557.1 (2004): 175-190.
Billeh, Yazan N., et al. "Revealing cell assemblies at multiple levels of granularity." Journal of neuroscience methods 236 (2014): 92-106.
Birdno, Merrill J., et al. "Mechanisms of deep brain stimulation in movement disorders as revealed by changes in stimulus frequency." Neurotherapeutics 5.1 (2008): 14-25.
Bito, Haruhiko, et al. "CREB phosphorylation and dephosphorylation: a Ca2+-and stimulus duration-dependent switch for hippocampal gene expression." Cell 87.7 (1996): 1203-1214.
Blondel, Vincent D., et al. "Fast unfolding of communities in large networks." Journal of statistical mechanics: theory and experiment 2008.10 (2008): P10008.
Borgens, et al. "Uncoupling histogenesis from morphogenesis in the vertebrate embryo by collapse of the transneural tube potential." Developmental dynamics 203.4 (1995): 456-467.
Borgens, et al. "Transected dorsal column axons within the guinea pig spinal cord regenerate in the presence of an applied electric field." Journal of Comparative Neurology 250.2 (1986): 168-180.
Borgens, R. B., et al. "An imposed oscillating electrical field improves the recovery of function in neurologically complete paraplegic dogs." Journal of Neurotrauma 16.7 (1999): 639-657.
Broggini, et al. "Pre-ictal increase in theta synchrony between the hippocampus and prefrontal cortex in a rat model of temporal lobe epilepsy." Experimental neurology 279 (2016): 232-242.
Brummer, S. B., et al. "Electrochemical considerations for safe electrical stimulation of the nervous system with platinum electrodes." IEEE Transactions on Biomedical Engineering 1 (1977): 59-63.
Buzsaki, Gyorgy, et al. "Neuronal oscillations in cortical networks." science 304.5679 (2004): 1926-1929.

Cao, Bing, et al. "Impairment of decision making associated with disruption of phase-locking in the anterior cingulate cortex in viscerally hypersensitive rats." Experimental neurology 286 (2016): 21-31.
Carballo-Molina, Oscar A., et al.. "Hydrogels as scaffolds and delivery systems to enhance axonal regeneration after injuries." Frontiers in cellular neuroscience 9 (2015): 13.
Chao, Moses V. "Neurotrophins and their receptors: a convergence point for many signalling pathways." Nature Reviews Neuroscience 4.4 (2003): 299-309.
Chao, Zenas C., et al. "Region-specific network plasticity in simulated and living cortical networks: comparison of the center of activity trajectory (CAT) with other statistics." Journal of Neural Engineering 4.3 (2007): 294-308.
Chao, Zenas C., et al. "Effects of random external background stimulation on network synaptic stability after tetanization." Neuroinformatics 3.3 (2005): 263-280.
Chwalek, Karolina, et al. "Engineered 3D silk-collagen-based model of polarized neural tissue." Journal of visualized experiments: JoVE 104 (2015).
Chwalek, Karolina, et al. "In vitro bioengineered model of cortical brain tissue." Nature protocols 10.9 (2015): 1362-1373.
Darbon, Pascal, et al. "Mechanisms controlling bursting activity induced by disinhibition in spinal cord networks." European Journal of Neuroscience 15.4 (2002): 671-683.
Davenport, Roger W., et al. "Hippocampal growth cone responses to focally applied electric fields." Journal of neurobiology 24.1 (1993): 89-100.
Domachuk, Peter, et al. "Bioactive "self-sensing" optical systems." Applied physics letters 95.25 (2009): 253702.
Eytan, et al. "Selective adaptation in networks of cortical neurons." Journal of Neuroscience 23.28 (2003): 9349-9356.
Ferrucci, R., et al. "Transcranial direct current stimulation improves recognition memory in Alzheimer disease." Neurology 71.7 (2008): 493-498.
Frohlich, Flavio. "Endogenous and exogenous electric fields as modifiers of brain activity: rational design of noninvasive brain stimulation with transcranial alternating current stimulation." Dialogues in clinical neuroscience 16.1 (2014): 93.
Gabriel, Sami, et al. "The dielectric properties of biological tissues: II. Measurements in the frequency range 10 Hz to 20 GHz." Physics in medicine & biology 41.11 (1996): 2251-2269.
Goold, Carleton P., et al. "Single-cell optogenetic excitation drives homeostatic synaptic depression." Neuron 68.3 (2010): 512-528.
Graves, Matthew S., et al. "Electrically mediated neuronal guidance with applied alternating current electric fields." Annals of Biomedical Engineering 39.6 (2011): 1759-1767.
Gross, Robert E., et al. "Advances in neurostimulation for movement disorders." Neurological research 22.3 (2000): 247-258.
Hilton, Brett J., et al. "Can injured adult CNS axons regenerate by recapitulating development?" Development 144.19 (2017): 3417-3429.
Hinkle, et al.. "The direction of growth of differentiating neurones and myoblasts from frog embryos in an applied electric field." The Journal of physiology 314.1 (1981): 121-135.
Hoffman-Kim, et al. "Topography, cell response, and nerve regeneration." Annual review of biomedical engineering 12 (2010): 203-231.
Holtmaat , et al. "Experience-dependent structural synaptic plasticity in the mammalian brain." Nature Reviews Neuroscience 10.9 (2009): 647-658.
Hronik-Tupaj, Marie, et al. "Neural responses to electrical stimulation on patterned silk films." Journal of biomedical materials research Part A 101.9 (2013): 2559-2572.
Hummel, Friedhelm, et al. "Effects of non-invasive cortical stimulation on skilled motor function in chronic stroke." Brain 128.3 (2005): 490-499.
Jayakar, P., et al. "A safe and effective paradigm to functionally map the cortex in childhood." Journal of clinical neurophysiology: official publication of the American Electroencephalographic Society 9.2 (1992): 288-293.

(56) References Cited

OTHER PUBLICATIONS

Jefferys, J. G. "Nonsynaptic modulation of neuronal activity in the brain: electric currents and extracellular ions." Physiological reviews 75.4 (1995): 689-723.
Jin, et al. "Tissue engineering bioreactor systems for applying physical and electrical stimulations to cells." Journal of Biomedical Materials Research Part B: Applied Biomaterials 103.4 (2015): 935-948.
Jimbo, Yasuhiko, et al. "The dynamics of a neuronal culture of dissociated cortical neurons of neonatal rats." Biological cybernetics 83.1 (2000): 1-20.
Jimbo, Y., et al. "Simultaneous induction of pathway-specific potentiation and depression in networks of cortical neurons." Biophysical journal 76.2 (1999): 670-678.
Kamioka, Hiroyuki, et al. "Spontaneous periodic synchronized bursting during formation of mature patterns of connections in cortical cultures." Neuroscience letters 206.2-3 (1996): 109-112.
Khambhati,Ankit N., et al. "Dynamic network drivers of seizure generation, propagation and termination in human neocortical epilepsy." PLoS computational biology 11.12 (2015): e1004608.
Kilgore, Kevin L., et al. "Nerve conduction block utilising high-frequency alternating current." Medical and Biological Engineering and Computing 42.3 (2004): 394-406.
Kim, Dae-Hyeong, et al. "Silicon electronics on silk as a path to bioresorbable, implantable devices." Applied physics letters 95.13 (2009): 133701.
Kim, Dae-Hyeong, et al. "Dissolvable films of silk fibroin for ultrathin conformal bio-integrated electronics." Nature materials 9.6 (2010): 511-517.
Kirkby, Lowry A., et al. "A role for correlated spontaneous activity in the assembly of neural circuits." Neuron 80.5 (2013): 1129-1144.
Koser, David E., et al. "Mechanosensing is critical for axon growth in the developing brain." Nature neuroscience 19.12 (2016): 1592-1598.
Lancaster, Madeline A., et al. "Cerebral organoids model human brain development and microcephaly." Nature 501.7467 (2013): 373-379.
Lancichinetti, A., et al. "Consensus clustering in complex networks. Sci. Rep. 2, 336." (2012).
Larson, et al. "Patterned stimulation at the theta frequency is optimal for the induction of hippocampal long-term potentiation." Brain research 368.2 (1986): 347-350.
Leondopoulos, Stathis S., et al. "Chronic stimulation of cultured neuronal networks boosts low-frequency oscillatory activity at theta and gamma with spikes phase-locked to gamma frequencies." Journal of neural engineering 9.2 (2012): 026015. Feb. 23, 2012.
Luhmann, Heiko J., et al. "Spontaneous neuronal activity in developing neocortical networks: from single cells to large-scale interactions." Frontiers in neural circuits 10 (2016): 40.
Madhavan, Radhika, et al. "Multi-site stimulation quiets network-wide spontaneous bursts and enhances functional plasticity in cultured cortical networks." Engineering in Medicine and Biology Society, 2006. EMBS'06. 28th Annual International Conference of the IEEE. IEEE, 2006. 1593-1596.
Maeda, Eisaku, et al. "The mechanisms of generation and propagation of synchronized bursting in developing networks of cortical neurons." Journal of Neuroscience 15.10 (1995): 6834-6845.
Malenka, Robert C., et al. "LTP and LTD: an embarrassment of riches." Neuron 44.1 (2004): 5-21.
Marom, et al. "Development, learning and memory in large random networks of cortical neurons: lessons beyond anatomy." Quarterly reviews of biophysics 35.1 (2002): 63-87.
Mathie, et al. "Neuronal ion channels and their sensitivity to extremely low frequency weak electric field effects." Radiation protection dosimetry 106.4 (2003): 311-315.
Mccaig, Colin D. "Electric fields, contact guidance and the direction of nerve growth." Development 94.1 (1986): 245-255.
Mccaig, C. D., et al. "Electrical fields, nerve growth and nerve regeneration." Experimental physiology 76.4 (1991): 473-494.
Mcintyre, Cameron C., et al. "Extracellular stimulation of central neurons: influence of stimulus waveform and frequency on neuronal output." Journal of neurophysiology 88.4 (2002): 1592-1604.
Morin, Fabrice O., et al. "Investigating neuronal activity with planar microelectrode arrays: achievements and new perspectives." Journal of bioscience and bioengineering 100.2 (2005): 131-143.
Myers, Jonathan P., et al. "Regulation of axonal outgrowth and pathfinding by integrin-ECM interactions." Developmental neurobiology 71.11 (2011): 901-923.
O'Brien, Ricahrd J., et al. "Activity-dependent modulation of synaptic AMPA receptor accumulation." Neuron 21.5 (1998): 1067-1078.
O'Keefe, John, et al. "Phase relationship between hippocampal place units and the EEG theta rhythm." Hippocampus 3.3 (1993): 317-330.
Opitz, et al. "Spontaneous development of synchronous oscillatory activity during maturation of cortical networks in vitro." Journal of neurophysiology 88.5 (2002): 2196-2206.
Park, James, et al. "Single-cell transcriptional analysis reveals novel neuronal phenotypes and interaction networks involved in the central circadian clock." Frontiers in neuroscience 10 (2016): 481.
Pan, et al. "Strict perpendicular orientation of neural crest-derived neurons in vitro is dependent on an extracellular gradient of voltage." Journal of neuroscience research 90.7 (2012): 1335-1346.
Pan, Liangbin, et al. "An in vitro method to manipulate the direction and functional strength between neural populations." Frontiers in neural circuits 9 (2015): 32.
Patel, et al. "Orientation of neurite growth by extracellular electric fields." Journal of Neuroscience 2.4 (1982): 483-496.
Patel, et al. "Perturbation of the direction of neurite growth by pulsed and focal electric fields." Journal of Neuroscience 4.12 (1984): 2939-2947.
Parodi, P., et al. "Segmentation of the response of a neuronal network into clusters with similar activity." BioSystems 48.1-3 (1998): 171-178.
Radman, Thomas, et al. "Role of cortical cell type and morphology in subthreshold and suprathreshold uniform electric field stimulation in vitro" Brain stimulation 2.4 (2009): 215-228.
Rajnicek, Ann M., et al. "Growth cone steering by a physiological electric field requires dynamic microtubules, microfilaments and Rac-mediated filopodial asymmetry." Journal of cell science 119.9 (2006): 1736-1745.
Rajnicek, Ann M., et al. "Electric field-induced orientation of rat hippocampal neurones in vitro." Experimental physiology 77.1 (1992): 229-232.
Rebola, et al. "Activity-dependent synaptic plasticity of NMDA receptors." The Journal of physiology 588.1 (2010): 93-99.
Rogers, Sherry L., et al. "Neurite extension by peripheral and central nervous system neurons in response to substratum-bound fibronectin and laminin." Developmental biology 98.1 (1983): 212-220.
Robinson, H. P., et al. "Periodic synchronized bursting and intracellular calcium transients elicited by low magnesium in cultured cortical neurons." Journal of neurophysiology 70.4 (1993): 1606-1616.
Ross, Bernhard, et al. "Synchronization of beta and gamma oscillations in the somatosensory evoked neuromagnetic steady-state response." Experimental neurology 245 (2013): 40-51.
Schubert, David. "Collaborative interactions between growth factors and the extracellular matrix." Trends in cell biology 2.3 (1992): 63-65.
Shahaf, et al. "Learning in networks of cortical neurons." Journal of Neuroscience 21.22(2001): 8782-8788.
Shapiro, Scott. "A review of oscillating field stimulation to treat human spinal cord injury." World neurosurgery 81.5-6 (2014): 830-835.
Shi, et al. "Three-dimensional gradients of voltage during development of the nervous system as invisible coordinates for the establishment of embryonic pattern." Developmental Dynamics 202.2 (1995): 101-114.
Singer, Wolf. "Neuronal synchrony: a versatile code for the definition of relations?." Neuron 24.1 (1999): 49-65.

(56) References Cited

OTHER PUBLICATIONS

Sood, Disha, et al. "Fetal brain extracellular matrix boosts neuronal network formation in 3D bioengineered model of cortical brain tissue." ACS biomaterials science & engineering 2.1 (2015): 131-140.

Staubli, Ursula, et al. "GABAB receptor antagonism: facilitatory effects on memory parallel those on LTP induced by TBS but not HFS." Journal of Neuroscience 19.11 (1999): 4609-4615.

Sun, et al. "Self-organization of repetitive spike patterns in developing neuronal networks in vitro." European Journal of Neuroscience 32.8 (2010): 1289-1299.

Tan, Huiling, et al. "Complementary roles of different oscillatory activities in the subthalamic nucleus in coding motor effort in Parkinsonism." Experimental neurology 248 (2013): 187-195.

Tandon, Nina, et al. "Electrical stimulation systems for cardiac tissue engineering." Nature protocols 4.2 (2009): 155-173.

Tang-Schomer, Min D., et al. "Neural circuits with long-distance axon tracts for determining functional connectivity." Journal of neuroscience methods 222 (2014): 82-90.

Tang-Schomer, Min D., et al. "Bioengineered functional brain-like cortical tissue." Proceedings of the National Academy of Sciences 111.38 (2014): 13811-13816.

Tang-Schomer, Min D., et al. "Film-Based Implants for Supporting Neuron-Electrode Integrated Interfaces for The Brain." Advanced functional materials 24.13 (2014): 1938-1948.

Tateno, et al. "Activity-dependent enhancement in the reliability of correlated spike timings in cultured cortical neurons." Biological cybernetics 80.1 (1999): 45-55.

Tateno, et al. "Analytical characterization of spontaneous firing in networks of developing rat cultured cortical neurons." Physical Review E 65.5 (2002): 051924.

Terzuolo, C. A., et al. "Measurement of imposed voltage gradient adequate to modulate neuronal firing." Proceedings of the National Academy of Sciences 42.9 (1956): 687-694.

Tien, Lee W., et al. "Silk as a multifunctional biomaterial substrate for reduced glial scarring around brain-penetrating electrodes." Advanced Functional Materials 23.25 (2013): 3185-3193.

Uhlhaas, Peter J., et al. "Abnormal neural oscillations and synchrony in schizophrenia." Nature reviews neuroscience 11.2 (2010): 100-113.

Wagenaar, Daniel A., et al. "Controlling bursting in cortical cultures with closed-loop multi-electrode stimulation." Journal of Neuroscience 25.3 (2005): 680-688.

Wagenaar, Daniel A., et al. "Effective parameters for stimulation of dissociated cultures using multi-electrode arrays." Journal of neuroscience methods 138.1-2 (2004): 27-37.

Wagner, et al. "Noninvasive human brain stimulation." Annu. Rev. Biomed. Eng. 9 (2007): 527-565.

Wood, Matthew D., et al. "Applied electric field enhances DRG neurite growth: influence of stimulation media, surface coating and growth supplements." Journal of neural engineering 6.4 (2009): 046003.

Yaffe, Robert B., et al. "Physiology of functional and effective networks in epilepsy." Clinical Neurophysiology 126.2 (2015): 227-236.

Yao, Li, et al. "Electrical signals polarize neuronal organelles, direct neuron migration, and orient cell division." Hippocampus 19.9 (2009): 855-868.

Yi, Guo-Sheng, et al. "Morphology controls how hippocampal CA1 pyramidal neuron responds to uniform electric fields: a biophysical modeling study." Scientific Reports 7.1 (2017): 3210.

Zhang, Li I., et al. "Electrical activity and development of neural circuits." Nature neuroscience 4.11s (2001): 1207-1214.

Zoladz, Jerzy A, et al. "The effect of physical activity on the brain derived neurotrophic factor: from animal to human studies." Journal of physiology and pharmacology: an official journal of the Polish Physiological Society 61 5 (2010): 533-41.

\* cited by examiner

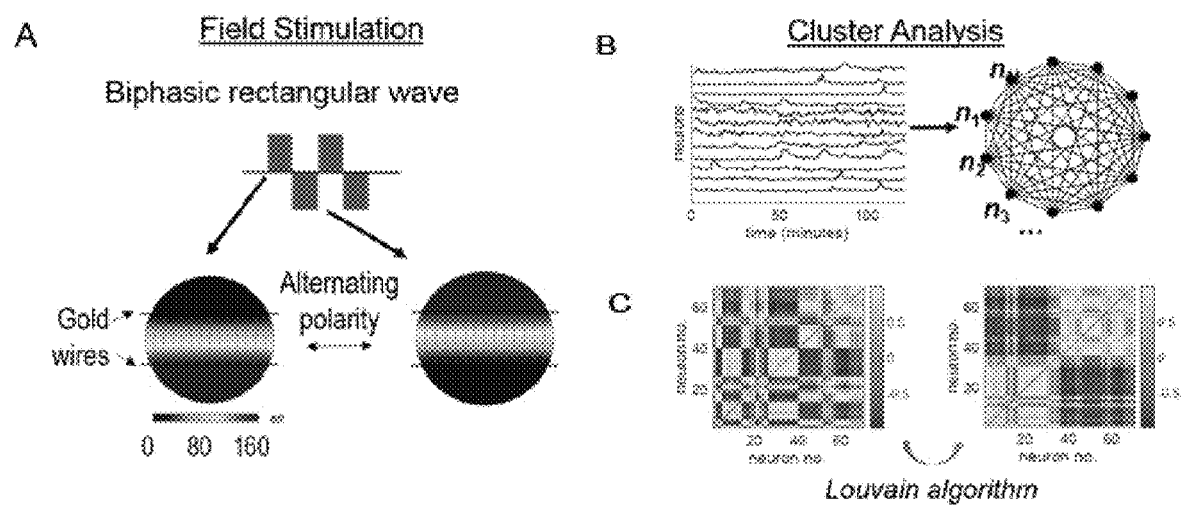
FIGS. 1 A-C

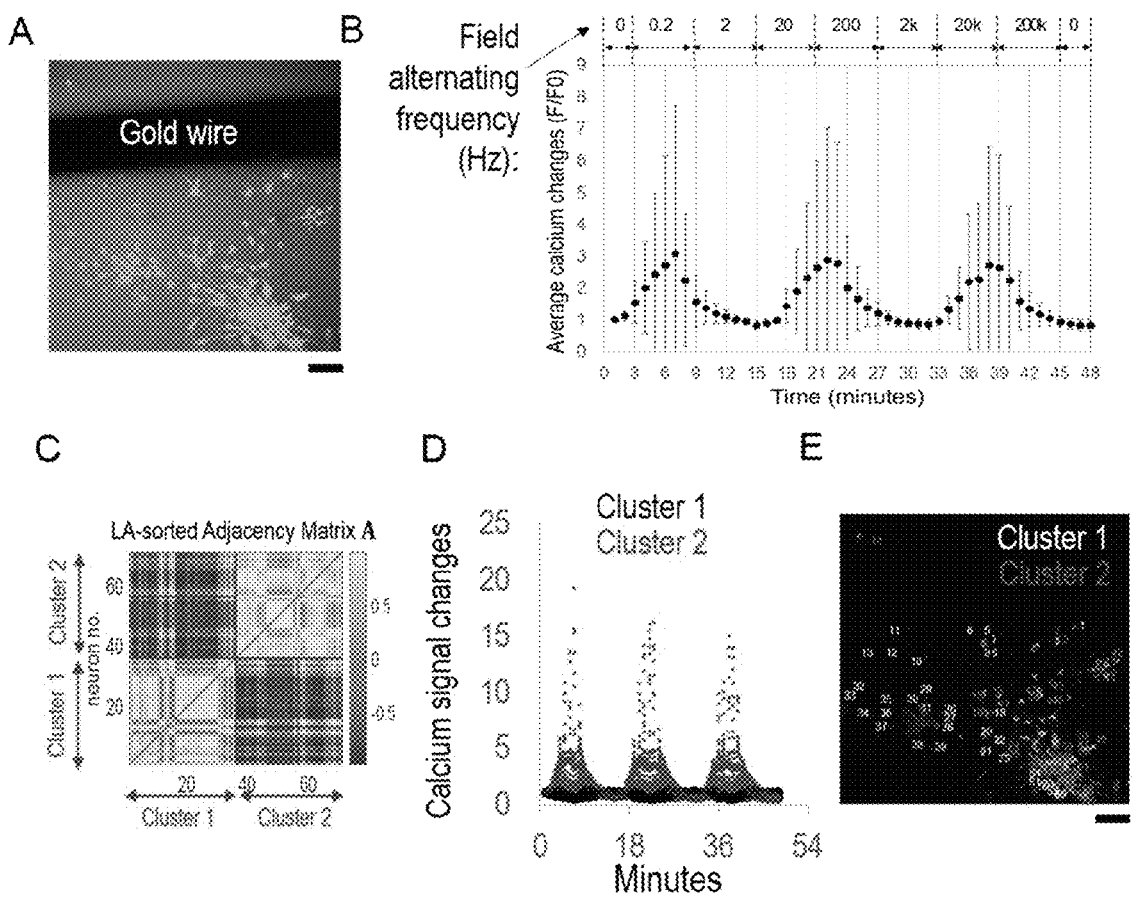
FIGS. 2 A-E

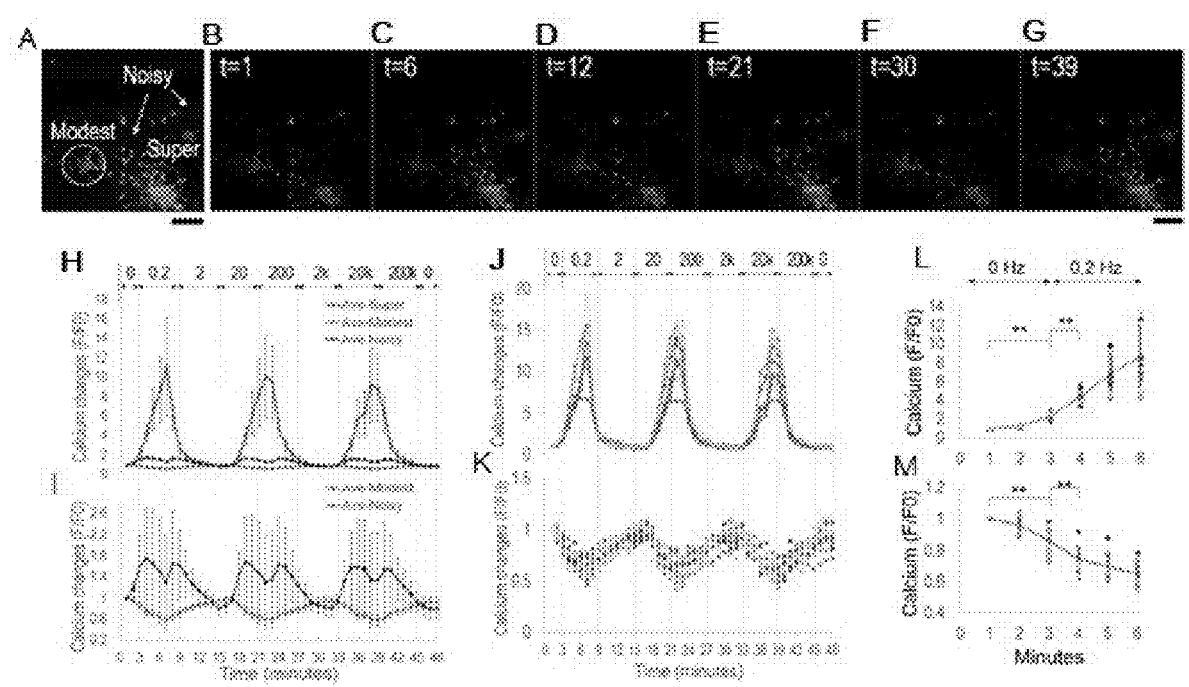
FIGS. 3 A-M

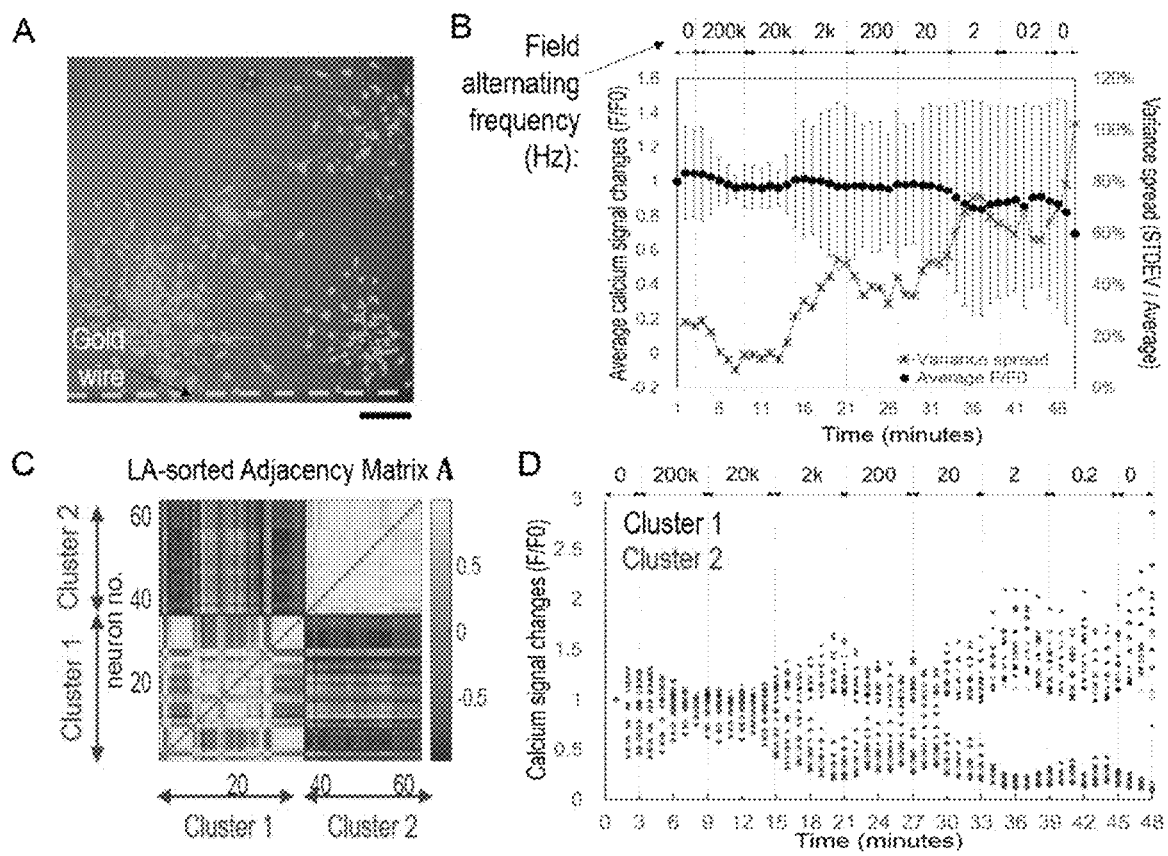
FIGS. 4 A-D

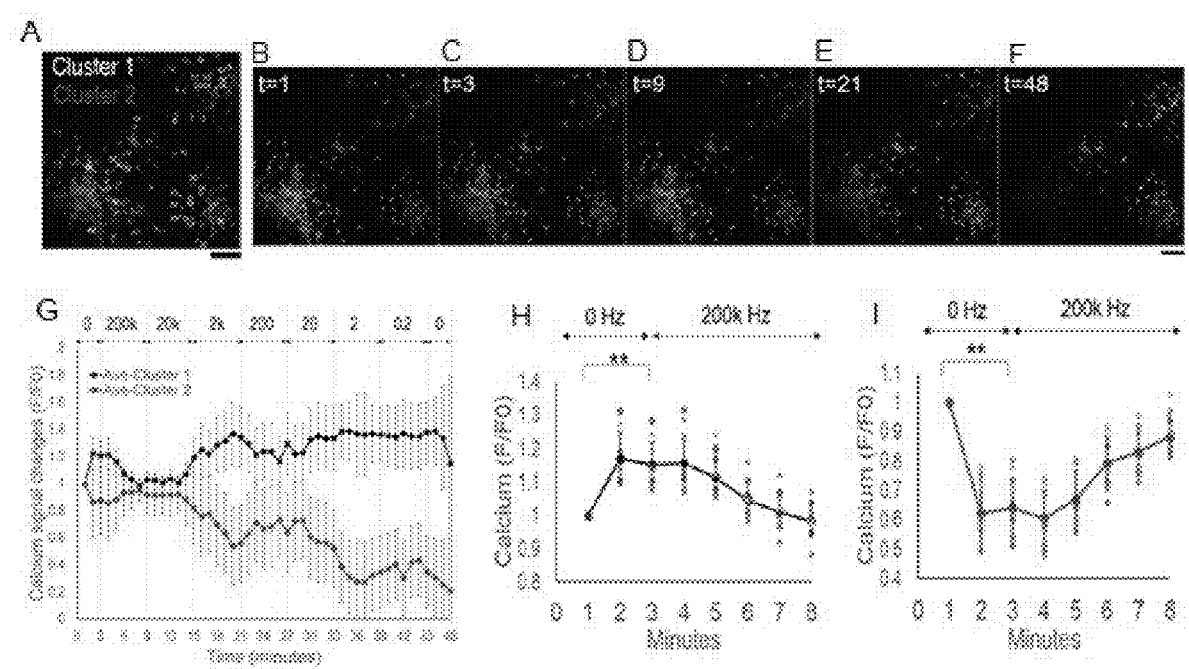
FIGS. 5 A-I

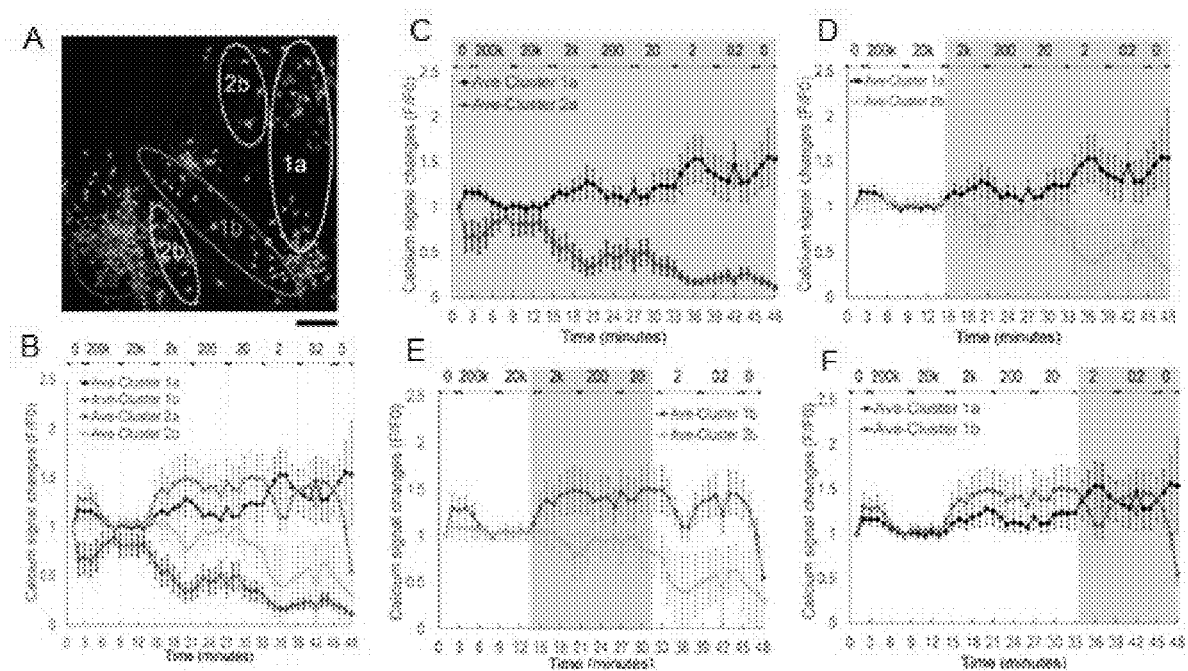
FIGS. 6 A-F

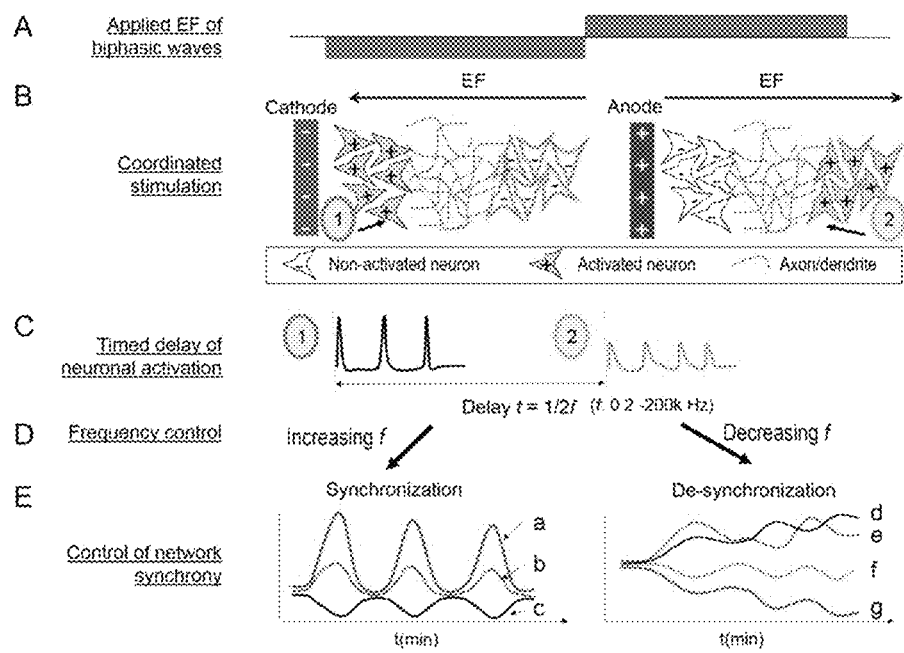
FIGS. 8 A-E

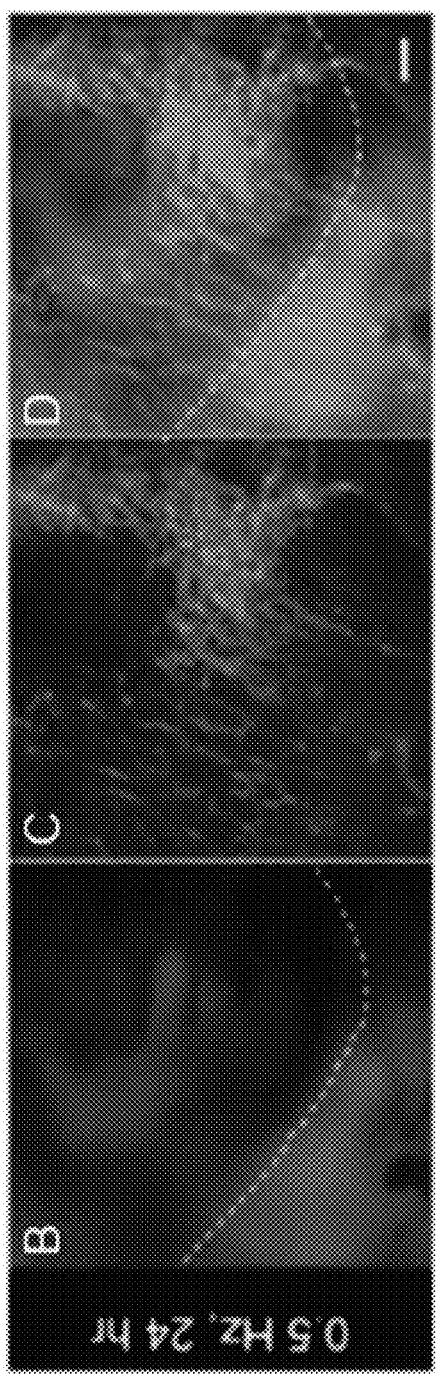
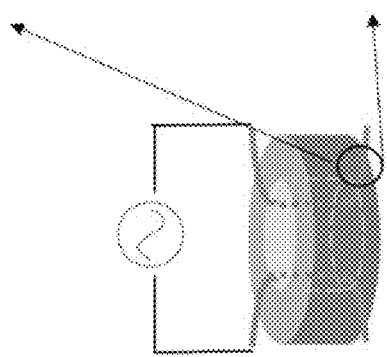
FIG. 10D
FIG. 10C
FIG. 10B
FIG. 10A

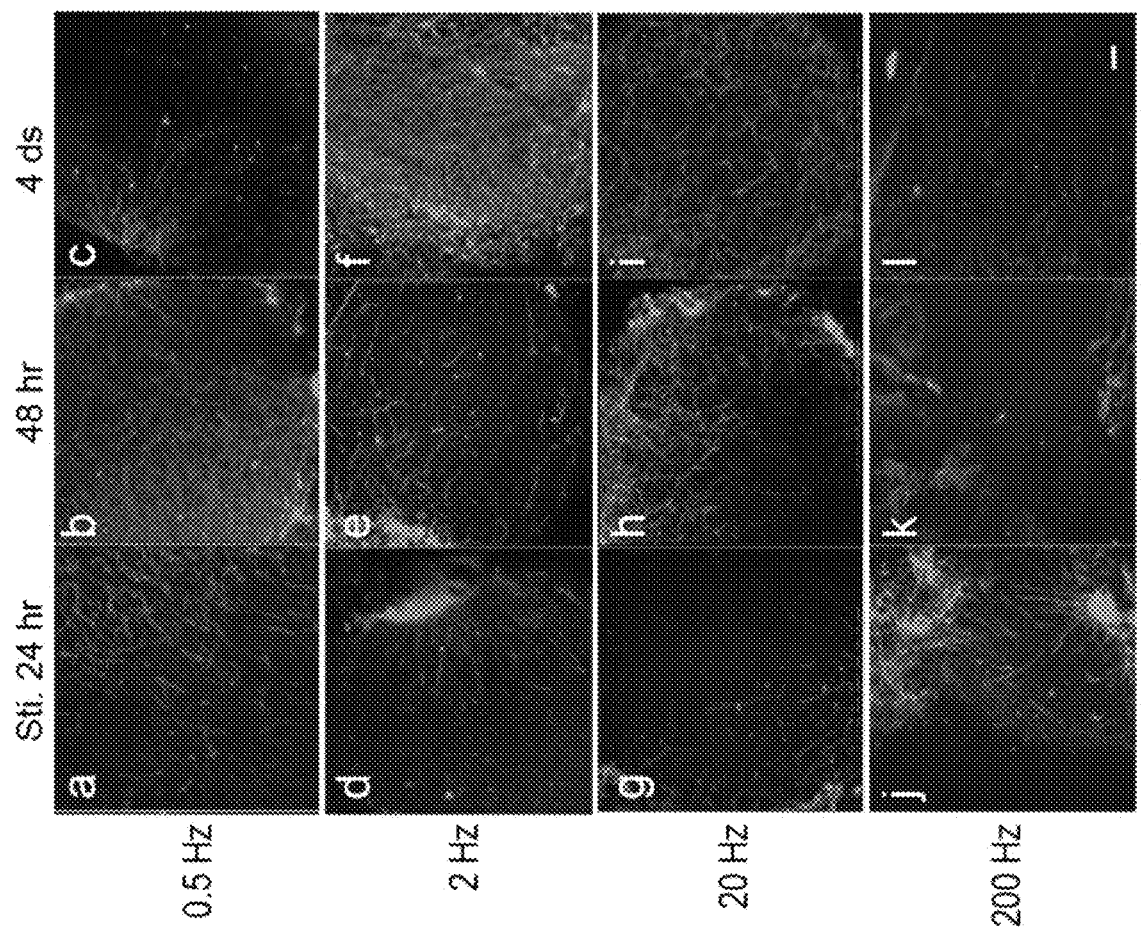
FIGS. 11A-L

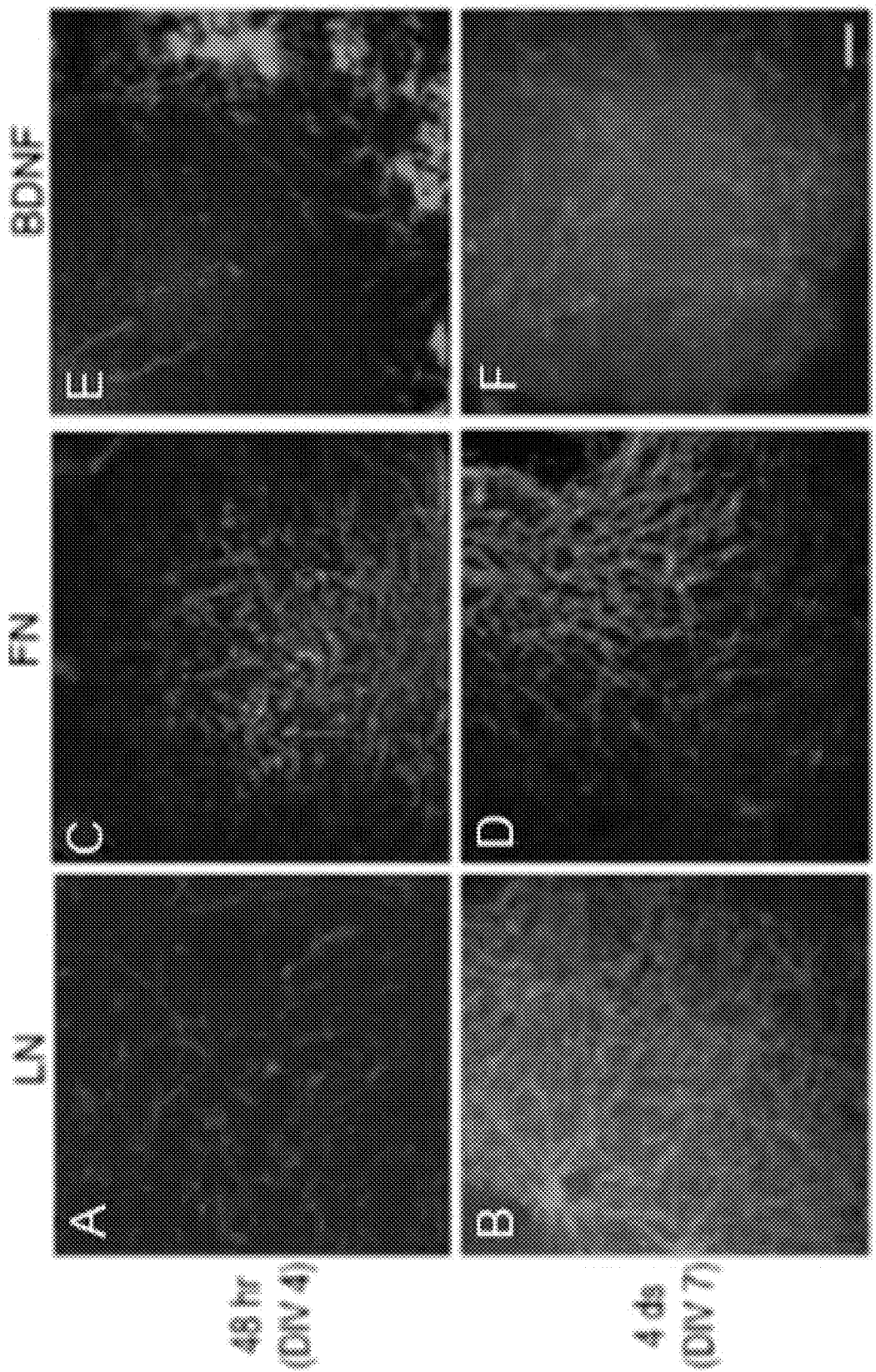
FIGS. 13A-F

NEURONAL STIMULATION MODEL, DEVICE AND METHODS USING ALTERNATE CURRENT

1. FIELD

The present disclosure relates generally to models and methods to modulate neuronal network activities by applying electric field (EF) to neuronal networks of neuronal cells in culture. In particular, the present disclosure relates to network control mechanism, involving coordinated stimulation of different subpopulations of neurons by alternating field polarity to achieve neuronal network synchrony in neural systems. The present disclosure provides model and modulation of neuronal network behavior for brain function assays and neuromodulation approaches. The present disclosure provides method of modulating directed growth of neuronal axon by applying an alternating electrical field to neuronal cells in a 3D culture. The present disclosure also provides methods of screening compounds using the disclosed models, kits and systems thereof.

2. BACKGROUND

Synchronized neural activities underlie many cognitive and behavioral responses during normal brain functioning (Buzsaki and Draguhn, 2004) and neurological disorders such as epilepsy (Yaffe et al., 2015) and schizophrenia (Uhlhaas and Singer, 2010). Neurons organize into functional networks that generate synchronized activities either spontaneously (Kirkby et al., 2013; Luhmann et al., 2016) or upon exogenous stimulus (Zhang and Poo, 2001; Tagawa et al., 2008). This process involves intrinsic molecular programs at the cellular level (Mathie et al., 2003; Holtmaat and Svoboda, 2009; Rebola et al., 2010; Bagley and Westbrook, 2012) and large scale (ensembles) information processing at the network level (Marom and Shahaf, 2002). Stimulating the central nervous system (CNS) with applied electric or magnetic field are used to probe neural networks in functional studies of the brain (Wagner et al., 2007; Bestmann et al., 2015). The applied electromagnetic fields affect CNS by generating a distributed electric field (EF) around the brain tissue underneath (McIntyre and Grill, 2002; Frohlich, 2014). Despite the wide ranging neuro-modulatory effects of exogenous EF on the nervous system, the underlying mechanism for induced network changes remains elusive.

Major challenges for functional studies lie in the complexity of neural networks and the highly variable dynamics of neuronal responses. Neuronal response depends on the stimulus as well as the cell's intrinsic properties. Features of a stimulus (intensity, waveform, frequency, duration, polarity) have effects for different neurons. Neuronal sensitivity depends on the cell's channel protein and receptor composition, synapse maturate state, and cell morphology (Mathie et al., 2003; Holtmaat and Svoboda, 2009; Rebola et al., 2010; Bagley and Westbrook, 2012; O'Brien et al., 1998; Yi et al., 2017). Models with defined network architecture and cell compositions, such as ex vivo brain slices or specific CNS pathways, are used to determine conditions capable of evoking functionally relevant responses.

In vitro cortical cultures allow much more detailed observation and manipulation than intact brains. Cultures exhibit spontaneous periodic calcium transients or bursting activities (Robinson et al., 1993; Jimbo et al., 2000; Maeda et al., 1995; Opitz et al., 2002), with increased propensity for synchronized bursting as the culture matures (Kamioka et al., 1996; Tateno et al., 2002; Sun et al., 2010). Interrogated by site-specific stimuli with varying temporal and spatial features, in vitro cortical networks exhibit in vivo-relevant adaptive behavior (Eytan et al., 2003). Studies have shown pathway-specific (rather than neuron-specific) changes in neuronal responsiveness (potentiation or depression) (Jimbo et al., 1999), and stimuli context-dependent plasticity (Bakkum et al., 2008a). Network-level signal propagation involves intrinsic firing of random neurons, recruitment of other neurons, and repetitive excitation leading to synchronous burst firing (Jimbo et al., 2000; Sun et al., 2010; Bakkum et al., 2008a; Chao et al., 2007). There is a need to identify stimulation conditions that can induce synchronized activities of a random network of in vitro cortical cultures.

Brain diseases and disorders, such as epilepsy and Alzheimer's, are becoming more prevalent in the general population. However, no adequate treatments or therapies are currently available, mainly due to a lack of understanding of the underlying mechanisms. Since conventional research methods, such as animal models and 2D tissue cultures, do not capture the complexity of human physiology, new methods are needed to study the human brain. A central challenge in Neuroscience is to understand how complex three-dimensional networks of neuronal cells form synapses and generate neuronal activity. Traditional neuronal cell culture experiments and electrophysiological techniques have limited in vitro studies of neuronal cells to the examination of relatively few cells interacting in only two dimensions. In order to study the principles of neuronal network formation in native neuronal tissue, in vitro methods must be developed to control neuronal cell activities, such as synchronization, directed growth and formation of synapses using non-invasive techniques for examining and stimulating individual cells. Currently available models have failed to support neuronal cell branching in three dimensions at an appropriate scale. Thus, there is a need for synchronization/asynchronization of the firing of neurons and directed growth of neurons in 3D.

3. SUMMARY

The present disclosure relates generally to models and methods to modulate neuronal network activities simulating normal brain functions and neurological disorders in a 3-dimensional (3D) culture. In particular, the present disclosure relates to the use of applied alternating electric field (EF) on neuronal networks of in vitro brain culture in a 3D system. In particular, the present disclosure relates to the surprising discovery of network control mechanism, involving coordinated stimulation of different subpopulations of neurons by alternating field polarity. Also disclosed is temporal coordination of distributed neuronal activity underlying network synchrony in neural systems. In particular, application of EF of a particular alternating frequency for a period of time results in neuronal communities of similar activity patterns. Large scale, synchronized oscillations of random network were induced by alternating EF of changing frequencies. The present disclosure provides model and modulation of neural network behavior for brain function assays and neuromodulation approaches. The present disclosure provides method of modulating directed growth of neuronal axon by applying an alternating field electrical signal in the presence of growth factors to neuronal axon of brain cell culture in a 3D system. The present disclosure also provides methods of screening compounds using the disclosed models, kits and systems thereof.

One of the main challenges in studying neural development is the lack of in vitro model and tools for modulating neural development. The present disclosure successfully engineered an in vitro system that promotes synchronization/asynchronization of neurons as well as modulating directed growth and maintenance of neurons. We have now surprisingly found a method of controlling neuronal network synchrony by applying an alternating electrical field to living neurons. The present disclosure provides a model for manipulating neuron activities and directed growth. The model is useful for screening for useful compounds that modulate neuronal cell activities and development. In one aspect, it is useful as an assay for diagnosing disorder from individual patient where a personalized model of neuronal cell culture can be made.

The system comprises a composition subjected to an alternating electric filed that supports growth and maintenance of viable neuronal cell in a 3D culture. In one aspect, the disclosure provides a neuronal cell culture under optimal culture conditions, while the neuronal cells can be analyzed using both optical, biochemical, electronic measurement methods.

In one aspect, the presently disclosed method provides a 3D culturing condition subjected to an alternating electric field where the neuronal axon has a growth of about 10-20%, about 20-30%, about 30-40% more in length compared to the axons of un-stimulated neurons In certain embodiments, the present system and methods may be used for research and/or clinical application (e.g., cell-based therapies, transplantation, regenerative medicine, diagnostics, screening and cell/tissue banking).

Provided herein is a method of modulating neuronal network activities comprising applying an alternating electric field (EF) to a neuronal network of neuronal cells in a 3D culture for a period of time, wherein the activities are synchronizing or desynchronizing the neuronal network of neuronal cells.

Provided herein is a method to synchronize oscillations of a random neuronal network comprising applying an alternating EF to a neuronal network of neuronal cell in a 3D culture for a period of time, wherein the EF comprises one or more frequencies, wherein the EF is applied by increasing the frequency from about 0.2 Hz to about 200 kHz.

Provided herein is a method to desynchronize oscillations of a neuronal network comprising applying an alternating EF to a neuronal network of neuronal cell in a 3D culture for a period of time, wherein the EF has one or more frequencies, wherein the EF is applied by decreasing the frequency from 200 kHz to 0.2 Hz.

Provided herein is a method to modulate directed growth of neuronal axon comprising applying an alternating field electrical signal to a neuronal cell comprising an axon in a 3D culture for a period of time.

Provided herein is a method to modulate directed growth of neuronal axon comprising applying an alternating field electrical signal to a neuronal cell comprising an axon in a subject for a period of time.

Provided herein is a system or apparatus for modulating neuronal network activities comprising: (i) providing an alternating electric field (EF) on neuronal network of neuronal cell in a 3D culture for a period of time; and (ii) measuring the activities of the neuronal network.

Provided herein is a system or apparatus for directed growth of neurons, the system comprising: (i) culturing the neurons on a 3D scaffold; (ii) providing growth enhancing molecules, trophic factors and nanoparticles on the 3D scaffold in a culture medium; and (iii) applying an alternating electrical field to the neurons thereby stimulating the neuron to grow.

Provided herein is a method for identifying an agent that modulates synchronization in a neuronal network comprising neuronal cells, said method comprises: (i) applying an alternating field electrical signal to the neuronal network in a 3D culture for a period of time; (ii) exposing the neuronal network to the agent; (iii) measuring the synchronization of the neuronal network, wherein a change of the synchronization of the neuronal network as compared with the neuronal network without exposure to the agent indicates that the agent is a modulator of the synchronization of the neuronal network.

Provided herein is a method for identifying an agent that modulates directed growth of neuronal cell comprising an axon comprising: (i) applying an alternating field electrical signal to the neuronal cell in a 3D culture for a period of time, (ii) exposing the neuronal cell to the agent; (iii) measuring the directed growth of the neuronal axon, wherein a change of the directed growth of the neuronal axon as compared with the neuronal axon of a neuronal cell in a 3D culture without exposure to the agent indicates that the agent is a modulator of the directed growth of the neuronal cell.

4.1 BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A.-C. Schematics of stimulation setup and network analysis. A. Field stimulation. Stimulus was delivered by substrate-embedded gold wires spanning the cortical culture. A biphasic, rectangular wave. COMSOL simulation of the electric field (160 mV peak-to-peak amplitude, 6 mm-apart electrode distance), as previously described (Tang-Schomer et al., 2014c). Field distribution at the positive and negative phases of the wave is shown. B.-C. Cluster analysis. B. Labeled neurons n_1, n_2, . . . n_N are envisioned as the nodes of an all-to-all graph (right) and the connection between any two neurons n_i, n_j is weighted by the Pearson correlation coefficient w_ij between the correspondent fluorescence intensity time series (left). C. Correlation-based weighted adjacency matrix A before (left) and after (right) sorting the neurons according to the community partition given by the Louvain algorithm. Color-map reports the range of correlation coefficients.

FIGS. 2A.-E. Network synchronization under alternating field with increasing frequencies. The cortical culture was exposed to an alternating field with frequencies increasing from 0.2 Hz to 200 kHz for 6 minutes per condition. A. Fluorescence image of fluo-4 stained neurons overlay with bright field image. The dark area is the film-embedded gold wire. Scale bar, 100 µm. B. Average calcium signal time series from 70 neurons. Error bar depicts the standard derivation. C. Correlation-based weighted adjacency matrix A after sorting the neurons according to the community partition given by the Louvain algorithm. Two clusters were obtained. Red lines mark the separation between Cluster 1 and Cluster 2. Color bar reports the range of Pearson's correlation coefficient values. D. Functional clusters color-coded onto the calcium signal time series. Cluster 1 (non-responders) in black, and Cluster 2 (super-responders) in red. E. Functional clusters mapped onto the original fluorescence image of the culture. Neurons in Cluster 1 (non-responders) in white, and those in Cluster 2 (super-responders) in red. Scale bar, 100 µm.

FIGS. 3A.-M. Oscillatory patterns of neuronal sub-populations under alternating EF of increasing frequencies. A. Neurons sub-divided into groups of Super-responders (Super), modest responders (Modest), and noisy responders (Noisy). B.-G. Representative fluorescence images of fluo-4 stained neurons at specified time points (in minutes). Note the differences of different groups' intensity changes. Scale bar, 100 µm. H.-I. Average calcium signal time series from each sub-population. H. Super-responders (red), modest-responders (blue) and noisy-responders (black). I. Magnified plots of modest-responders (blue) and noisy-responders (black). Error bar depicts the standard derivation. J.-K. Individual calcium signal time series of super-responders J. and modest-responders K. L.-M. Calcium signal time series of the first 6 minutes of stimulation experiment, 0-3 min no stimulation and transition to 0.2 Hz from the $3^{rd}$ minute. L. Super-responders. M. Modest-responders. Error bar depicts the standard derivation. ANOVA test, **, $p<0.01$.

FIGS. 4A.-D. Symmetrical sub-population's oscillatory patterns under alternating EF with decreasing frequencies. The cortical culture was exposed to an alternating field with frequencies decreasing from 200 kHz to 0.2 Hz for 6 minutes per condition. A. Fluorescence image of fluo-4 stained neurons overlay with bright field image. The substrate-embedded gold wire is right blow the imaged area outside the field of view. Scale bar, 100 µm. B. Average calcium signal time series from 63 neurons (dot), and variance spread defined as standard derivation divided by the mean (cross). Note the large error bar (standard derivation) in lower frequencies. C. Correlation-based weighted adjacency matrix A after sorting the neurons according to the community partition given by the Louvain algorithm. Two clusters were obtained. Red lines mark the separation between Cluster 1 and Cluster 2. Color bar reports the range of Pearson's correlation coefficient values. D. Functional clusters color-coded onto the calcium signal time series. Cluster 1 in black, and Cluster 2 in red. Note the symmetry of their signal patterns.

FIGS. 5A.-I. Inhibition of spontaneous activity by high frequency alternating EF. A. Functional clusters mapped onto the original fluorescence image of the culture under alternating EF with decreasing frequencies. Neurons in Cluster 1 in white, and those in Cluster 2 in red. B.-F. Representative fluorescence images of fluo-4 stained neurons at specified time points (in minutes). Note the differences of different groups' intensity changes. Scale bar, 100 µm. G. Average calcium signal time series from Cluster 1 (black) and Cluster 2 (red). Error bar depicts the standard derivation. H.-I. Calcium signal time series of the first 6 minutes of stimulation experiment, 0-3 min no stimulation and transition to 200 kHz from the $3^{rd}$ minute. H. Cluster 1. I. Cluster 2. Error bar depicts the standard derivation. ANOVA test, **, $p<0.01$.

FIGS. 6A.-F. Network de-synchronization under alternating EF with decreasing frequencies. A. Functional clusters (1a, 1b, 2a, 2b) mapped onto the original fluorescence image of the culture under alternating EF with decreasing frequencies. Scale bar, 100 µm. B. Average calcium signal time series of each sub-population (1a, black; 1b, blue; 2a, red; 2b, yellow). C.-F. Pair-wise comparison of sub-population's calcium signal time series. C. Cluster 1a vs. 2a. D. Cluster 1a vs. 2b. E. Cluster 1b vs. 2b. F. Cluster 1a vs. 1b. Grey background highlights the symmetrical areas of the plots.

FIGS. 7A.-E. Lack of network synchronization under monophasic EF. A. Wave function comparison of biphasic square wave and monophasic pulses of the same frequency. The monophasic pulse (0.1 ms) trains capture the initial field changes of each positive phase of the corresponding biphasic wave. B.-C. Fluorescence images of neurons B. and corresponding calcium time series C. under pulse trains of increasing frequencies. D.-E. Fluorescence images of neurons D. and corresponding calcium time series E. under pulse trains of decreasing frequencies. Only neurons with significant spiking activities are shown in the calcium time series, and marked onto the corresponding images. Scale bar, 100 µm.

FIGS. 8A.-E. Hypothesis of coordinated stimulation by alternating EF of changing frequencies. A. Biphasic wave stimulation is applied. B. Two populations (1 and 2) with different EF threshold are located at different distances from a nearby electrode. When the electrode is cathode (left), population 1 is activated (in green, + indicating depolarization) and population 2 non-activated (in white, − indicating no change or hyperpolarization). When the electrode turns to anode (right), population 1 is in-activated and population 2 activated. C. Calcium transients occur upon neuronal activation (left for population 1; right for population 2). There would be a timed delay of the population activation, as the inverse of two times of the EF frequency. D. Control of the EF alternating frequency provides a means to alter the timed delay, thus associate or dissociate the two neuronal populations' activities. E. Network synchrony control by EF alternating frequency. (Left) Increasing EF frequency provides repetitive stimulus, and the wide span of frequency range activate different sub-populations. Combined, these conditions lead to network synchrony. The initial evoked response to the applied EF depends on neurons' spontaneous state at the time of stimulus, therefore, resulting in population-specific oscillations with different amplitude or phase patterns (a, b, c). (Right) Conversely, decreasing EF frequency could "unbound" the endogenous activities of different neuronal populations. The initial high frequency (i.e. 200 kHz) stimulation supresses all activities. As the frequency decreases, the timing between neuronal activation increases. Therefore, the sub-populations are less likely to fire together, resulting in divergent oscillation patterns of different amplitude (d vs. e in the early stages, and f vs. g) or different phase patterns (d vs e). Biphasic wave stimulation of a random network produces coordinated activation of different sub-populations A., illustrated as 1 (left) and 2 (right), due to the alternating field polarity. B. Applied field frequency (f) introduces a timed delay (½f) of the coordinated activities of distributed sub-populations. B. Increasing polarity alternating rate increases the temporal association of different sub-populations, leading to synchronous response of group-specific oscillations entrained in the network-level oscillation. C-left. Conversely, an initial high frequency stimulation supresses global activities. As the field alternating rate decreases, different sub-populations are less coordinated, and the network diverges into group-specific activities of different amplitude and phase patterns. C-right.

Figure 9A:
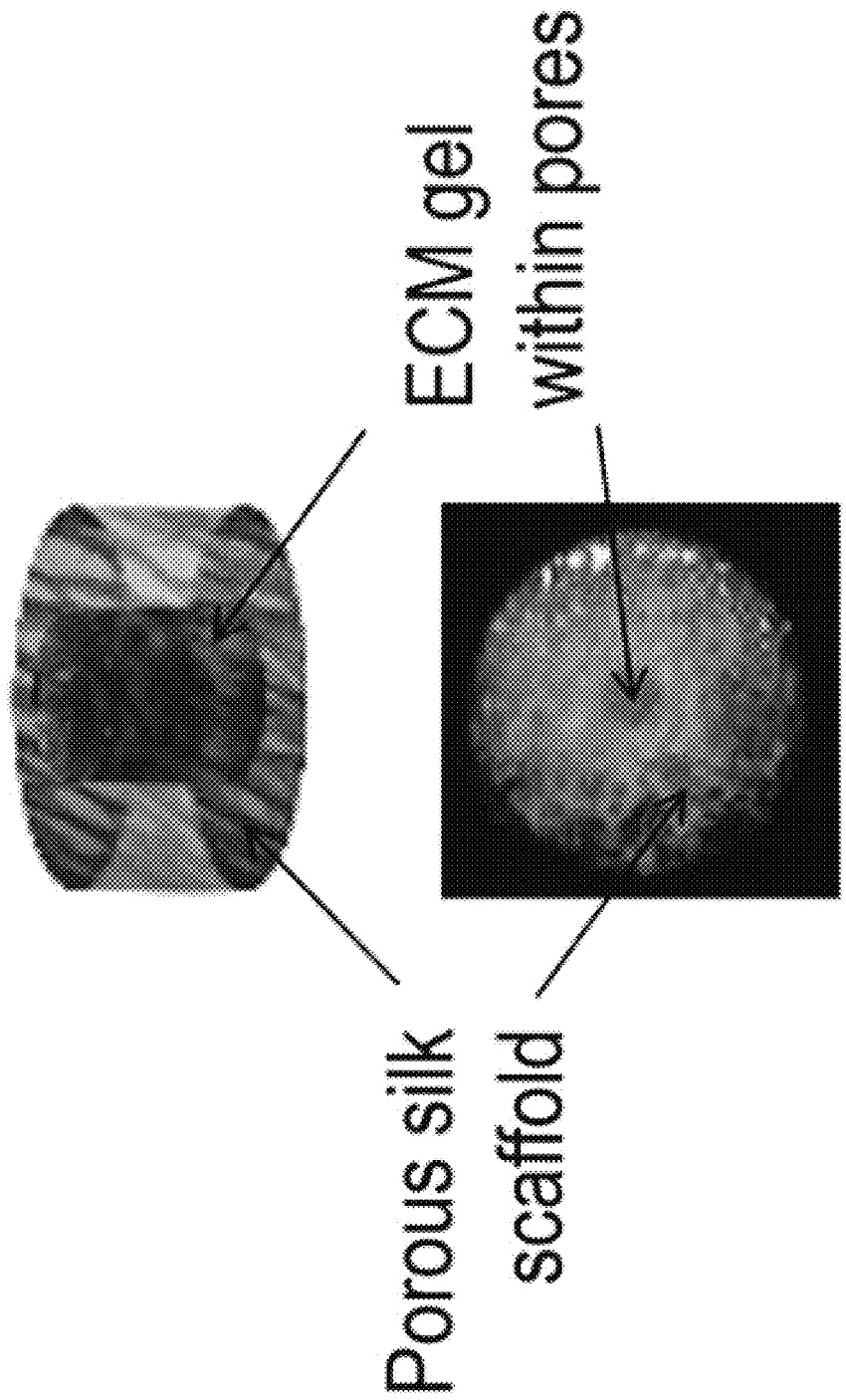
Figures 9B, 9C:
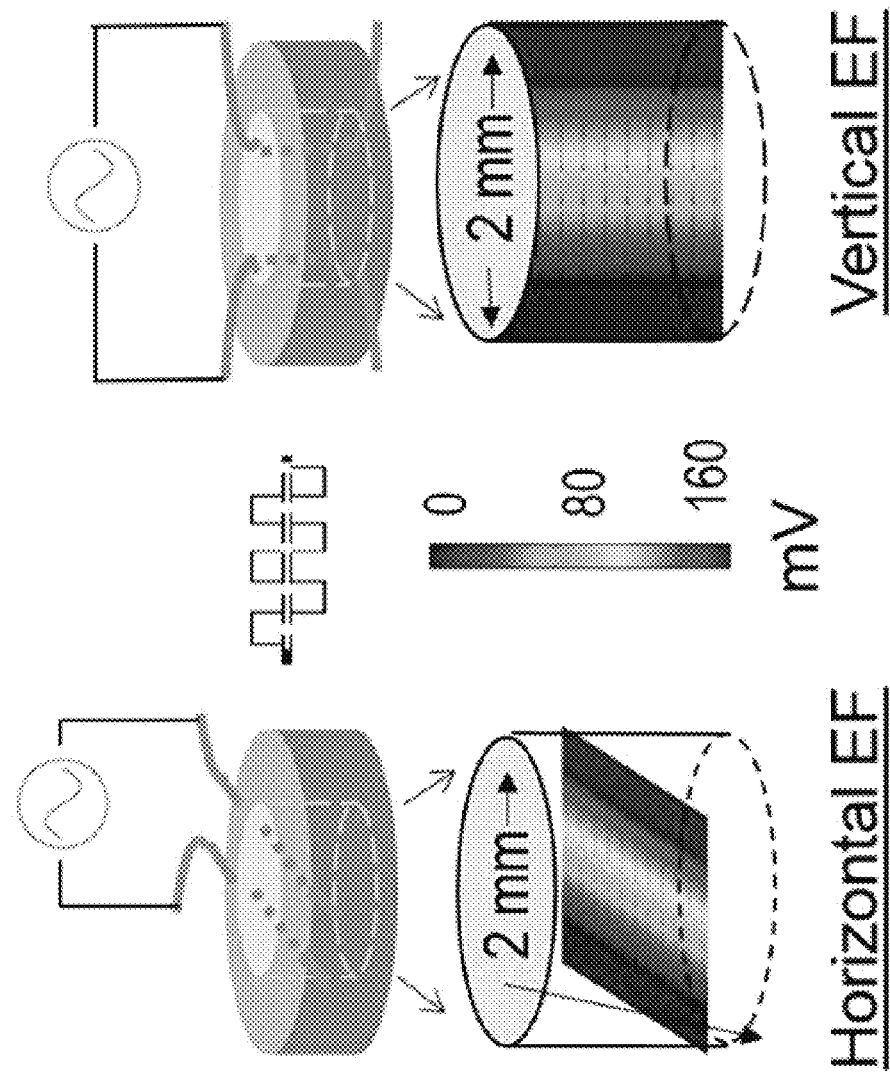

FIGS. 9A.-D. Schematics of 3D brain tissue model, electrical stimulation and local soluble factor delivery. A. 3D donut-shaped silk protein material-based neuronal culture. Neuronal cell bodies are confined to the scaffold region; whereas axon outgrowth occur in the center extracellular matrix (ECM) gel filled region. B.-C. Delivery of alternating electric fields. A pair of thin gold wires (dia. 100 µm; distance, ~2 mm) are threaded into a 3D scaffold, abutting the central core and embedded within the ECM gel matrix. The placement of the wires is either horizontal B. or vertical C. D. Local delivery of soluble factors. A 10 µL Hamilton syringe is used to deliver 1 µL solution into the ECM gel-filled center of a 3D culture.

FIGS. 10A.-J. Axon 3D growth at 24 hr after electrical stimulation. A.-D. Neurite orientation near an electrode. A. Schematics of a 3D tissue model with vertically placed electrode pair. The circled area shows the imaged region in B-D. B. Bright field showing the embedded electrode marked as a dashed line. C. 2D projection of β III-tubulin stained neurites. D. Overlay image of neurites trespassing the electrode (dashed line). Scale bar, 100 μm. E.-H. Neurite extension into the gel-filled center core. E. Schematics of a 3D tissue model with horizontally placed electrode pair. The circled area shows the imaged region F-H. F.-H. Overlay of 2D projections of β III-tubulin stained axons with bright field images of embedded electrodes (dashed line). Scale bar, 100 μm. I.-J. 3D neurite tracing and measurement. I. Representative 3D traced neurites as purple lines. Numbers in μm. J. Axon length measurements. Students' t-test, *, $p<0.05$; **, $p<0.01$.

FIGS. 11A.-N. Axon 3D growth after 4 days of continuous electrical stimulation. A.-I. Representative 2D projections of β III-tubulin stained axons in the center core region of 3D donut-shaped brain tissue models, under 0.5 Hz (A, B, C), 2 Hz (D, E, F), 20 Hz (G, H, I) and 200 Hz (J, K, L). Scale bar, 100 μm. M. Quantification of axon 3D growth, in control (black) and under 0.5 Hz (green), 2 Hz (blue), and 20 Hz (red) N. Quantification of axon lengths of after 4 days of stimulation. Students' t-test, *, $p<0.05$; **, $p<0.01$.

Figure 12C:
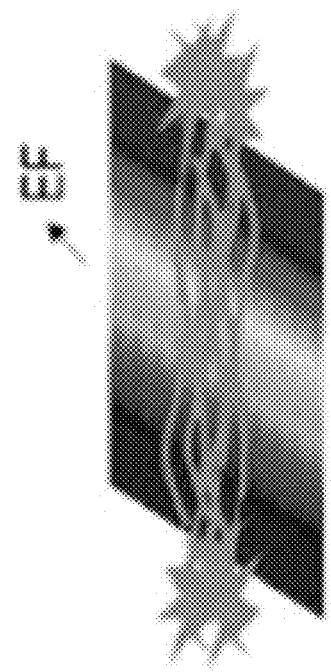
Figure 12B:
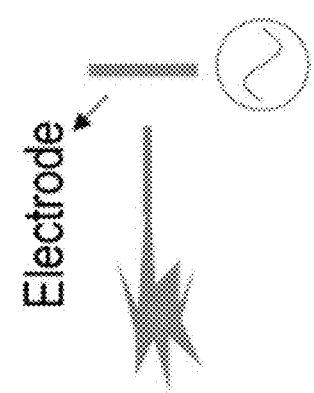
Figure 12A:
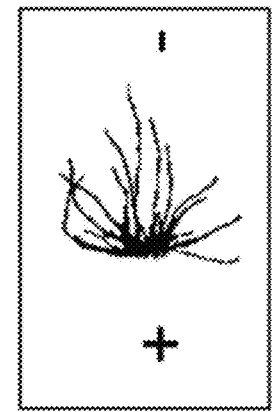
Figures 12D, 12E, 12F:
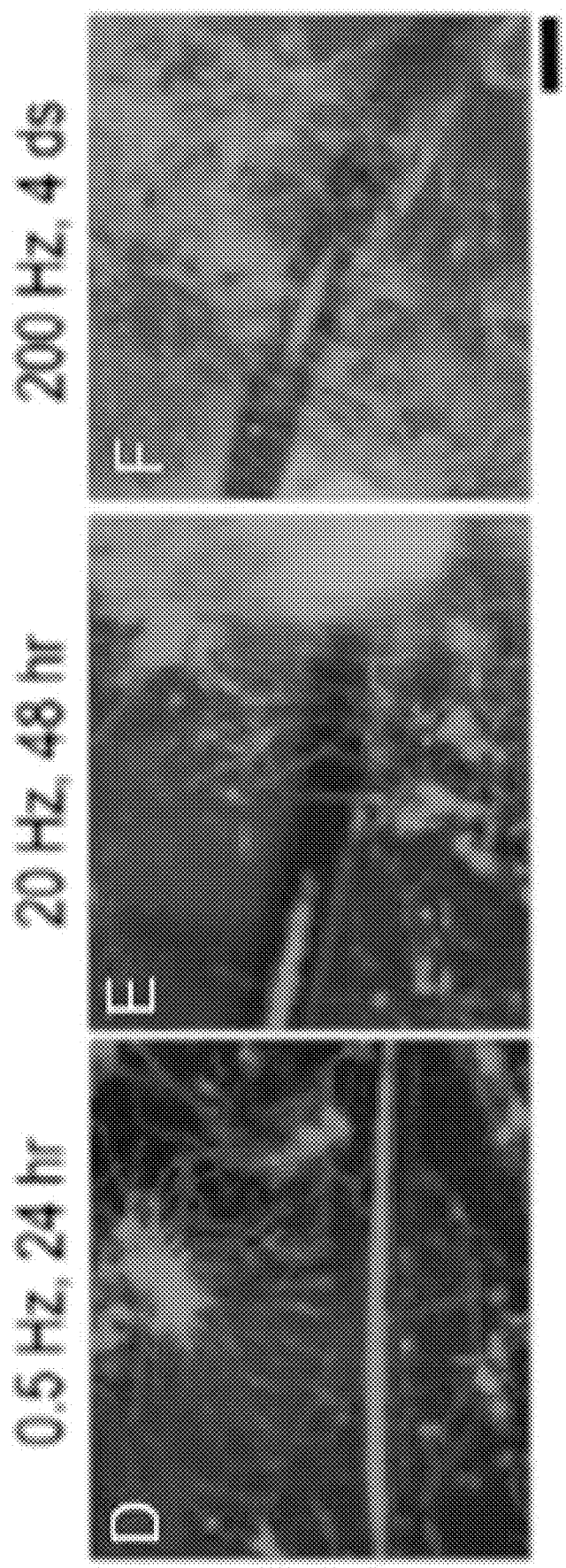

FIGS. 12A.-K. Axon 3D orientation under electrical stimulation. A.-C. Schematics of axon orientation under electrical fields. A. DC field-induced cathode-orientation of neurite outgrowth. B.-C. Hypothesized neurite orientation in AC field. B. A neuron extends its neurite perpendicularly towards an adjacent electrode as an on-off cathode. C. Between paired electrodes, once the axon has traversed away from its originating electrode for half a distance of an EF, it would seek the other closer electrode as the cathode; the outcome would be axon tracts in parallel to the EF direction. D.-G. Neurite orientation adjacent to electrodes. D.-F. Representative 2D projections of β III-tubulin stained neurites trespassing electrodes. Scale bar, 100 μm. G. Histogram of the neurite's angle relative to its adjacent electrode. H.-L. Neurite orientation between paired electrodes. H.-J. Representative 2D projection of β III-tubulin stained axons in the gel-filled center region. EF direction marked in white arrows. Scale bar, 100 μm. K. Histogram of the axon's angles relative to the EF direction.

FIGS. 13A-M. Axon 3D growth after local delivery of soluble factors and comparison to electrical stimulation. A.-F. Representative 2D projections of β III-tubulin stained axons in the center region of 3D tissue models, at 48 hr and 4 ds after local delivery of laminin (LN) (A, B), fibronectin (FN) (C, D), and BDNF (E, F). Scale bar, 100 μm. G.-J. Representative 2D projections of β III-tubulin stained axons in the center region of 3D tissue models, of control G. and at 4 ds after local delivery of GDNF H., NGF I., and NT3 (J.; Inset, 48 hr after delivery). Scale bar, 100 μm. K. Quantification of axon 3D lengths after 48 hr soluble factor delivery. L. Quantification of axon 3D length growth of 3D cultures with 48 hr and 4 days exposure (Exp.) of soluble factors. M. Comparison of axon lengths of DIV7 3D cultures of control (Ctrl) and those with 4 days of 2 Hz stimulation and exposure to LN, FN and BDNF. All quantifications used Students' t-test, *, $p<0.05$; **, $p<0.01$.

FIGS. 14A-B. Electric Field Setup for Neuronal Cultures. Micro-electrodes are either embedded in a 2D substrate (A) or a 3D scaffold (B) to deliver external electrical stimulus from connected functional generators. For 2D cultures (A), the electrodes can be embedded wires (a), or as an array printed onto a substrate (b) that supports live neurons. For 3D cultures (B), the wire electrodes can be introduced horizontally (a) or vertically (b) to the direction of neuronal growth. The color map shows COMSOL simulated electric field distribution. EF, electric field.

4.2. DEFINITIONS

The term "neuronal network" means a group of connected neurons that performs a certain function.

The term "neuronal communities" means a group of nodes that tend to interact with other nodes in the same group more often than the nodes outside the group. For a neuronal community, each neuron is a node.

The term "synchronize" means a correlated appearance in time of two or more events associated with various aspects of neuronal activity.

The term "asynchronize" means a lack of detectable correlated appearance in time of two or more events associated with neuronal activity.

The term "random network" or "random neurons" or "random neuronal network" mean a group of nodes with no correlated activities between any two nodes. For a neuronal network, each neuron is a node. "Random neurons" refer to a group of neurons with no correlated activities between any cells.

The term "substantially free" of an agent should be understood as meaning free of the agent, or that any amount of the agent present in the composition is so low so as not to have any effect on the process, on the outcome of the process or on the properties of the biological material (for example cell viability) after it is taken out of the conditions. In certain embodiment, the term "substantially free" of an agent means that the agent is less than 5% w/w (or % w/v, or % v/v), less than 4% w/w (or % w/v, or % v/v), less than 3% w/w (or % w/v, or % v/v), less than 2% w/w (or % w/v, or % v/v), less than 1% w/w (or % w/v, or % v/v), less than 0.5% w/w (or % w/v, or % v/v), less than 0.2% w/w (or % w/v, or % v/v), less than 0.1% w/w (or % w/v, or % v/v), less than 0.05% w/w (or % w/v, or % v/v), less than 0.02% w/w (or % w/v, or % v/v), or less than 0.01% w/w (or % w/v, or % v/v).

The term "about" in reference to a numeric value refers to ±0.5.

The term "extra cellular matrix (ECM)" refers to the extracellular part of animal tissue that usually provides structural support to the cells in addition to performing various other important functions. The extracellular matrix is the defining feature of connective tissue in animals. Extracellular matrix includes the interstitial matrix and the basement membrane. Interstitial matrix is present between various cells (i.e., in the intercellular spaces). Gels of polysaccharides and fibrous proteins fill the interstitial space and act as a compression buffer against the stress placed on the ECM. Basement membranes are sheet-like depositions of ECM on which various epithelial cells rest.

5. DETAILED DESCRIPTION

Disclosed are novel method to apply alternating electric field on random neuronal networks, and guiding principles for control of network synchrony in vitro.

It is surprising to discover that when applying alternating current to neurons, rather than activating a particular type of neurons, the alternating current can synchronize the firing of the neurons. If there is no change in frequency, random neurons are activated. However, when the frequency is increased, the neurons start to synchronize at the same frequency in a large spatial scale (different subgroups divided into different synchronization) and for a long duration (1 hour or more). Neurons started to synchronize according to the position from the source of the applied current and the neurons are divided into subgroups. When frequency is lowered, the neurons start to divide into subgroups. The neurons are asynchronized when the frequency is lowered. Both synchronization and asynchronization of the neurons can be used as a disease model.

It is discovered that electrical stimulation at certain frequencies under alternative current can stimulate growth and orient the direction of how mammalian axons are grown in a 3D culture. Provided herein is a method to induce cortical network activities including, but not limited to, temporal and spatial associations of neuronal populations by varying the frequencies and directions of applied electrical stimulus. Provided herein is an in vitro model of a subject with normal brain function. Provided herein is an in vitro model of a subject with a neurological disorder. In certain embodiments, the present invention provides disease model for disorder including, but not limited to, Alzheimer's disease, stroke and spinal cord injury. In certain embodiments, the present disclosure provides an in vitro system that mimics neuronal activity. In one aspect, provided herein is a method of screening for psychotropic drugs. The present disclosure provides methods to mitigate disease in the central nervous system. In one aspect, the disclosure is directed to a product that is placed as an interface for directed growth in culturing neuronal cells. In one aspect, the disclosure is directed to an apparatus comprising a 3D scaffold, electrode embedded in scaffold in the presence of neuronal cell culture medium, wherein the electrode is connected to an alternating electrical field.

The advancement of 3D tissue engineering provides new avenues for developing human brain tissue models. 3D constructs more closely resemble in vivo tissue in terms of cellular communication, the formation of biochemical and physio-chemical gradients and the development of extracellular matrix (ECM). The matrix helps the cells to move within the 3D construct similar to the way cells would move in living tissue. 3D constructs are thus improved models for cell migration, differentiation, survival, and growth. Furthermore, 3D tissue cultures provide more accurate depiction of cell polarization, since in 2D, the cells can only be partially polarized. The latter is particularly important for neuronal cells.

Therefore, the 3D culture according to the present disclosure is preferred over the prior art known in the field, particularly for personalized neuronal cell model for individual subject and for testing of compounds and intervention strategies that modulate the neuronal cells. These strategies include methods such as electrical stimulation, electromagnetic stimulation, ultrasound wave stimulation, etc. that are not biochemically based.

In one aspect, the 3D tissue culture method of the present disclosure provides drug efficacy and/or toxicity screenings, investigative/mechanistic toxicology, target discovery/identification, drug repositioning studies, and pharmacokinetics, pharmacodynamics assays, and regenerative medicine.

In one embodiment, the 3D scaffold is made of silk fibroin solution prepared from *Bombyx mori* (commonly known as silkworm) cocoons. The versatility of the silk material processing provides a scaffold base that has mechanical properties similar to the native brain tissue. As an inert biomaterial, the silk fibroin-based scaffold base does not react with neurons. In certain embodiments, addition of a polylysine coating encourages neuronal attachment. The porous structure allows infusion of exogenous ECM components to produce a genuine 3D microenvironment; permitting separate examinations of bio-active components, such as ECM protein types, from the properties of a 3D structure, such as stiffness and shape.

Gold wire-embedded silk protein film-based substrate was used to investigate the effects of applied electric field (EF) on random neuronal networks of in vitro cortical cultures. Two weeks-old cultures were exposed to EF of 27 mV/mm for 20-50 minutes and monitored by time-lapse calcium imaging. The network activity was represented by time series of calcium signals mapped to the source neurons. Computational analysis based on graph theory was used for unbiased detection of neuronal communities of similar activity patterns. Large scale, synchronized oscillations of the random network were induced by alternating EF of changing frequencies. Field polarity change was found to be necessary for network synchrony as monophasic fields of similar frequency changes failed to induce correlated activities among neurons. Change of the EF frequency was also critical as alternating EF of a constant frequency did not produce synchronized activities. The initial evoked response showed group-specific changes dependent on the sub-population's spontaneous activity prior to the stimulation. The binary changes of either activity increase or decrease resulted in opposite phase patterns of different sub-populations. Sub-population specific oscillatory patterns were entrained by network-level synchronous oscillations when the alternating EF frequency was increased from 0.2 Hz to 200 kHz. Conversely, as the EF frequency decreased over the same range span, more complex behavior emerged showing sub-population specific amplitude and phase patterns. Disclosed herein is a network control mechanism, involving coordinated stimulation of different sub-populations by alternating field polarity. The timed delay by change of EF frequency presented a means for temporal coordination of distributed neuronal activity underlying network synchrony in other neural systems. These novel EF effects on random neuronal networks provide important understanding of neural network behavior for brain functional studies and testing neuromodulation approaches.

In one aspect of the present disclosure, control of axon growth and alignment in a CNS environment is critical for nervous system development and regenerative growth. The present disclosure explores the effects of exogenous stimulus of electrical signals and soluble factors on axon 3D growth, using a silk protein material-based 3D brain tissue model. A pair of gold wires were threaded into the 3D tissue model, positioned at the interface of the scaffold region and the center gel region, spanning the axon growth area. This setup delivered applied electrical field directly to growing axons, and the effects were compared to local delivery of soluble factors including extracellular (ECM) components and neurotrophic factors. In one embodiment, dissociated rat cortical neurons were exposed to an alternating field of 80 mV/mm at 0.5 Hz to 2 kHz or soluble factors for up to 4 days, starting on day 3 in vitro (DIV 3), and evaluated by of β III-tubulin immunostaining, confocal imaging and 3D neurite tracing. In one embodiment, 0.5 to 20 Hz were found to promote axon length growth, with 2 Hz producing the biggest effect of ~30% axon length increase compared to control cultures. In one embodiment, ECM components of laminin and fibronectin delivery resulted significantly greater axon length initial growth compared to neurotrophic factors, such as BDNF, GDNF, NGF and NT3. In one embodiment, though axon lengths under 2 Hz stimulation and LN or FN exposure were statistically similar, significant AC-induced axon orientation was found under all frequencies tested. In one embodiment, the effects include perpendicular orientation of axons trespassing an electrode and aligned axon tracts in parallel to the field direction. In one embodiment, the electrode in AC field acts as an alternating cathode that attracts the growing tip of the axon, and AC field between pair electrodes orient axon tract formation in parallel to the field direction. Provided in this disclosure is the use of alternating electric field stimulation to direct axon 3D length growth and orientation. In one aspect, the present disclosure provides stimulation parameters, in conjunction of delivery of growth promoting soluble factors in a brain mimetic 3D environment. In one aspect, the present disclosure teaches the fundamental effects of electrical fields on nervous system development and for testing neuromodulation approaches to promote neural regeneration.

5.1 Methods of Analyzing Neuronal Activities-Synchronization/Asynchronization of Neurons In certain embodiments, the present disclosure identifies stimulation conditions that can induce synchronized activities of a random network of in vitro cortical cultures. To avoid some of the model-specific features with point stimulation, a uniform field with substrate-embedded electrode pair was applied spanning the culture.

Population-wide analysis of neuronal activities requires the detection of families of neurons having a similar activity pattern, so that the original neuronal network can be decomposed into distinct clusters. With electrical recordings, algorithms are needed for detecting bursts and defining their attributes (time stamp, duration) as unitary events, and for correlation analysis of the time series of bursts. Alternatively, calcium live imaging can be used to monitor large populations of neurons within a field of view simultaneously. Synchronized calcium transients are direct result of propagation of bursts of action potentials that are generated periodically by in vitro cortical cultures. When mapped onto the source neurons, calcium time series allow for direct comparison of the temporal and spatial patterns of neuronal activities. Computational analysis of calcium signals based on graph theory and network community detection were developed to identify functionally correlated neuronal clusters. A local greedy-optimization algorithm was tested (Blondel et al., 2008) to automatically determine the best partition of the neuronal population (i.e., number of communities and composition of each detected community) with minimal computational cost. Communities returned by the algorithm are entirely based on calcium signals and therefore capture a common behavior across neurons.

Community detection in functional networks were used for the unsupervised identification of neuronal communities that, within a given culture, exhibit homogenous fluorescence-based discharge patterns. Locally-greedy, resolution-adaptive algorithms (Bassett et al., 2013) and null models (Newman, 2010) are available to guarantee fast neuron clustering, while avoiding the detection of spurious and statistically nonsignificant communities. Synchronized neuronal activities have been observed experimentally in vitro and in vivo using a variety of techniques, including calcium imaging, multielectrode array recordings, and paired patch-clamp recordings (reviewed in Kirkby et al, Neuron, v 80, issue 5, 2013). Correlated activities of individual neurons are used to determine network synchronization.

In certain embodiments, provided herein are systems and methods for producing synchronous neural responses. A method according to one embodiment includes selecting a target stimulation frequency of an alternating current that is above a threshold frequency, with the threshold frequency corresponding to a refractory period for neurons of a target sensory neural population. In one embodiment, an alternating current is directed to a target neuron population at a stimulation frequency with individual neurons of the neural population completing corresponding individual refractory periods at the same time, resulting in synchronous neuron response to the electrical signal. In one embodiment, a direct current is directed to a target neuron population at a stimulation frequency with individual neurons of the neural population completing corresponding individual refractory periods at different times, resulting in synchronous neuron response to the electrical signal.

As used herein, the refractory period refers generally to the period of time during which an activated neuron (e.g., a neuron that has fired an action potential) is unable to fire an additional action potential. Unless otherwise noted, a refractory period as used herein generally refers to the entire or total refractory period, e.g., the combined absolute refractory period and relative refractory period. The refractory period can correspond to an average expected refractory period for a population of neurons, or to a refractory period of a particular neuron.

5.2 Neuronal Cells

The present disclosure provides a method to control network synchrony by applying an electric field with alternating polarity and changing frequencies. In certain embodiments, the method provides synchronized neuronal activities.

In another aspect, the present disclosure provides a process for directed growth and maintenance of neuronal cells by subjecting the neuronal cells to alternating electric field. The present disclosure provides 3D scaffolds subjected to an electric field with alternating polarity and changing frequencies for the directed growth and maintenance of neuronal cells that are superior than 2D culture. In certain embodiments, the neurons that are useful in the present disclosure may be obtained in the brain or spinal cord. The neurons that are useful include but are not limited to hippocampal, peripheral neurons such as dorsal root ganglia, cerebral neurons, e.g., purkinje cells, retinal ganglion cells, inner and outer hair cells in the cochlea, spinal cord neurons, etc. In one embodiment, the neuronal cells were cultured on a 2-dimensional culture surface before being transferred to a 3-D scaffolds.

The composition of the present disclosure comprises neuronal cells that are primary cells, stem cells, immortalized cells and a combination thereof. Cells that are cultured directly from a subject are known as primary cells. With the exception of some derived from tumors, most primary cell cultures have limited lifespan. After a certain number of population doublings, primary cells undergo the process of senescence and stop dividing, while generally retaining viability.

Stem cells are undifferentiated, or partly differentiated, biological cells that can differentiate into specialized cells and can divide (through mitosis) to produce more stem cells. They are found in multicellular organisms. In mammals, there are two broad types of stem cells: embryonic stem cells, which are isolated from the inner cell mass of blastocysts, and adult stem cells, which are found in various tissues. In adult organisms, stem cells and progenitor cells act as a repair system for the body, replenishing adult tissues. The third type of stem cells are engineered stem/progenitor cells; one example being induced pluripotent cells that are transformed fibroblasts with stem cell-properties.

An immortalized cell line is a population of cells from a multicellular organism which would normally not proliferate indefinitely but, due to mutation, have evaded normal cellular senescence and instead can keep undergoing division. The cells can therefore be grown for prolonged periods in vitro. The mutations required for immortality can occur naturally or be intentionally induced for experimental purposes.

In one embodiment, the neuronal cells are not expanded prior to, during or after plating, and/or the cells are not passaged after plating. Most primary cells, such as neuronal cells have only a limited capacity of being expanded. In contrast thereto, stem cells, immortalized cells and tumor cells have, generally speaking, the capacity of being expanded. Plating of cells plays a role only in one particular subdivision of 3D cell culture, namely in those types of cell culture where cells are expanded prior to transferring them into a 3D tissue culture process. As discussed above this applies only to a very limited number of primary cells, as well as to stem cells, tumor cells and immortalized cells.

In certain embodiments, the neuronal cells are mammalian cells, including, but not limited to, human cells, murine cells, porcine cells, canine cells, equine cells, rodent cells and bovine cells.

In some embodiments, the tissues are obtained from an infant, child, adult, and elderly subject. In one embodiment, the tissues are obtained from an embryo. The tissues of the disclosed methods can be isolated or obtained from juvenile, adult, or post-mortem tissues of a mammal. The cells of the disclosed methods can be isolated or obtained from the central nervous system ("CNS").

The disclosed methods include obtaining neuronal cells residing in regions of a mammalian CNS such as the neuroepithelium. Other CNS regions from which neuronal cells can be isolated include the ventricular and subventricular zones of the CNS and other CNS regions which include mitotic precursors as well as post-mitotic neurons. In an embodiment, the disclosed methods can employ neuronal cells residing in regions of a developing mammalian CNS.

In an embodiment, the neuronal cells are produced from tissues in the CNS in an area which is naturally neurogenic for a desired population of neurons. The desired population of cells may include the cells of a specific neuronal phenotype which can replace or supplement such phenotype lost or inactive in a neurological condition.

A variety of different neuronal subtypes, including those useful for treatment of specific neurodegenerative diseases or conditions can be obtained from neuronal cells developed from different areas or regions of the CNS. In certain embodiments, the CNS tissues are obtained across different gestational ages during fetal development. Neuronal cells that are developed from tissues isolated from different areas or regions of the CNS and across different gestational ages are used for optimal expansion and neuronal differentiation capacity. In some embodiments, the neuronal cells establish physiological relevance in the present disclosed cultured method.

5.3 Application of Electric Field

Electrical field in biphasic waves, may be applied to cortical neurons by a pair of substrate-embedded gold wires spanning the in vitro culture. The biphasic wave introduced EF of alternating polarity during the positive and negative phases of the wave function, at the rate of the wave frequency.

The parameters of stimulus (amplitude, frequency, duration) may be determined by paring with intracellular recording of evoked responses of targeted neurons. In certain embodiments, a voltage of about 100-120 mV, about 120-130 mV, about 130-140 mV, about 140-150 mV, about 150-160 mV across about 2-4 mmm, about 4-6 mm, about 6-8 mm, or about 8-10 mm showed a system frequency-dependent calcium response of cortical neurons. In certain embodiments, the electric field setup generated a theoretical EF strength of about 0.1-15 mV/mm, 15-20 mV/mm, about 20-27 mV/mm, about 27-30 mV/mm, about 30-35 mV/mm, or about 35-40 mV/mm, above the threshold extracellular voltage gradient of about 0.1-1 mV/mm, 1-3 mV/mm, about 3-5 mV/mm, about 5-8 mV/mm, or about 8-10 mV/mm for evoked neuronal response.

In certain embodiments, the field intensity in an in vitro system is 200-300 µV/mm, 300-400 µV/mm, 400-500 µV/mm. In certain embodiments, the duration is 1-2 weeks, 2-3 weeks, 3-4 weeks, 4-6 weeks, 6-8 weeks, 8-10 weeks, 10-12 weeks, 12-15 weeks. In one embodiment, the field intensity and duration is 200 µV/mm for up to 4 weeks. In one embodiment, the oscillating electric fields is 500-600 µV/mm for 18 days. In one embodiment the oscillating electric fields is 500-600 µV/mm, 15-min on/15-min off, for up to 15 weeks. In one embodiment, the electric current is applied to neurons in culture.

In certain embodiments, the field intensity in an in vivo system is 200-300 µV/mm, 300-400 µV/mm, 400-500 µV/mm. In certain embodiments, the duration is 1-2 weeks, 2-3 weeks, 3-4 weeks, 4-6 weeks, 6-8 weeks, 8-10 weeks, 10-12 weeks, 12-15 weeks. In one embodiment, the field intensity and duration is 200 µV/mm for up to 4 weeks. In one embodiment, the oscillating electric fields is 500-600 µV/mm for 18 days. In one embodiment the oscillating electric fields is 500-600 µV/mm, 15-min on/15-min off, for up to 15 weeks. In certain embodiments, the electric current is directly applied to live neurons and live systems.

In certain embodiments, biphasic waves with field polarity alternate from about 0.2-0.5 Hz, about 0.5-1 Hz, about 1-10 Hz, about 10-20 Hz, about 20-30 Hz, about 30-40 Hz, about 40-50 Hz, about 50-60 Hz, about 60-80 Hz, about 80-100 Hz, about 100-120 Hz, about 120-140 Hz, about 140-160 Hz, about 160-180 Hz or about 180-200 Hz, or about 200-2000 Hz may be applied. In certain embodiments, the neuronal cells are exposed to alternating electric field of increasing frequencies. In certain embodiments, the neuronal cells are exposed to alternating electric field of decreasing frequencies.

In certain embodiments, the electrical stimulation has a duration of about 2-4 hrs, 4-6 hrs, 6-8 hrs, 8-10 hrs, 10-12 hrs, 12-14 hrs, 14-16 hrs, 16-18 hrs, 18-20 hrs, 20-22 hrs, 22-24 hrs, 24-48 hrs, 2-4 days, 4-7 days, 1-2 weeks or 2-4 weeks. In certain embodiments, the neuronal cell is subjected to varying frequencies at about 0.2-0.5 Hz, about 0.5-1 Hz, about 1-2 Hz, about 2-4 Hz, about 4-6 Hz, about 5-10 Hz, about 10-15 Hz, about 15-20 Hz, about 20-40 Hz, about 40-60 Hz, about 60-80 Hz, about 80-100 Hz, about 100-150 Hz, about 150-200 Hz, about 200-250 Hz, about 250-500 Hz, about 500-1000 Hz, or about 1-2 kHz. In certain embodiments, the axon length has grown about 400-600 µm, about 600-800 µm, about 800-1000 µm, about 1000-1100 µm, about 1100-1200 µm, about 1200-1300 µm, about 1300-1400 µm, or about 1400-1500 µm, 1500-3000

µm. In certain embodiments, the neuronal cell showed signs of cell death after about 20-24 hrs, about 24-36 hrs, about 36-48 hrs, about 2-3 days, about 3-4 days, about 4-6 days of stimulation.

5.4 Directional Growth

When electric field is applied to a neuronal cell cultured in a 3D scaffold, axon growth is measured for various electrical stimulation duration. In certain embodiments, the electrical stimulation has a duration of about 2-4 hrs, 4-6 hrs, 6-8 hrs, 8-10 hrs, 10-12 hrs, 12-14 hrs, 14-16 hrs, 16-18 hrs, 18-20 hrs, 20-22 hrs, 22-24 hrs, 24-48 hrs, 2-4 days, 4-7 days, 1-2 weeks or 2-4 weeks. In certain embodiments, the neuronal cell is subjected to varying frequencies at about 0.2-0.5 Hz, about 0.5-1 Hz, about 1-2 Hz, about 2-4 Hz, about 4-6 Hz, about 5-10 Hz, about 10-15 Hz, about 15-20 Hz, about 20-40 Hz, about 40-60 Hz, about 60-80 Hz, about 80-100 Hz, about 100-150 Hz, about 150-200 Hz, about 200-250 Hz, about 250-500 Hz, about 500-1000 Hz, or about 1-2 kHz. In certain embodiments, the axon length has grown about 400-600 µm, about 600-800 µm, about 800-1000 µm, about 1000-1100 µm, about 1100-1200 µm, about 1200-1300 µm, about 1300-1400 µm, or about 1400-1500 µm. In certain embodiments, the neuronal cell showed signs of cell death after about 20-24 hrs, about 24-36 hrs, about 36-48 hrs, about 2-3 days, about 3-4 days, about 4-6 days of stimulation.

In certain embodiments, the neurons are grown in a controlled direction that facilitates a formation of neuronal network in a short period of time. In some embodiments, synapses may be formed in about 1-2 days, about 2-4 days, about 4-7 days, about 1-2 weeks, about 2-4 weeks.

In a 3D environment, neurons have a higher degree of freedom of neurite movement and growth. In one embodiment, neurons adjacent to electrodes grew their extensions in perpendicular to the electrode. In certain embodiments, the angle between the neurites and the electrode is about 40-45, 45-50, 50-55, 55-60, 60-65, 65-70, 75-80, 80-85 85-90 degrees. In certain embodiments, the angle between the neurites and the electric field direction is about 0-5, 5-10, 10-15, 15-20, 20-25, 25-30 degrees. The percentage of neurite that has an angle in the above range is about 20-30%, 30-40%, 40-50%, 50-60%, 60-70%, 70-80%, 80-90%, or 90-100%.

5.5 Culture Medium

One of the conventional methods in growing and maintaining mammalian neuronal cells is to use 2D plastic substrate. However, this often produces less than ideal conditions to grow, expand and maintain neuronal cells. This is in part due to a failure to replicate the conditions experienced by neuronal cells during normal neuronal cell development, a process which differs from 2D culture. 3D culture systems aim to more faithfully replicate some of the conditions during neurogenesis. In particular, such 3D systems allow cells to interact with each other to a greater degree and allow the development of complex multicellular neural aggregates than using 2D cell culture.

The 3D systems comprise a bioactive scaffold onto which the cells can be seeded and to which they can adhere. Such a scaffold directs the growth and proliferation of cells in a desired 3D configuration and provides certain molecular signals which help the cells to form the desired structures. Scaffolds may compose of a variety of materials which facilitate growth, proliferation and differentiation of the cells which are seeded onto it. For example, scaffolds are commonly composed of polymeric materials which are arranged into the form of a porous sponge. Cells seeded onto this scaffold can attach and grow inside the pore structure of the scaffold through the network of interconnecting tunnels and channels inside the scaffold, with pore size being an important consideration when selecting an appropriate scaffold. Bioactive agents, such as extracellular matrix (ECM) components, may also be used to enhance scaffold function when deposited onto a scaffold surface, permitting greater cell adhesion.

5.6 Matrigel and Extracellular Matrix (ECM)

For successful growth and maintenance of neuronal cells, a robust and consistent culture that has stable expansion capacities is desirable. As described above, the culture methods can be optimized to achieve long-term, stable expansion of neuronal cells from different areas and ages of CNS development in the subject.

Although extracellular matrix proteins can be effective in promoting cell adhesion, different amino acid polymers, such as poly-L/D-ornithine or poly-L/D-lysine, can be toxic to the cells at certain concentrations for each individual cell line. The duration of incubation can also affect the final amount of the polymer deposited on the dish surface affecting the viability of the cells. For the neuronal cells employed in the disclosed methods, concentrations of polymer can be within a range of between about 0.1 µg/mL and about 1 mg/mL. In one embodiment, 10 µg/ml of polylysine is dissolved in 0.01 M HEPES buffer or water at neutral pH and applied to a culture vessel. The culture vessel is incubated for ≥1 hour at room temperature. The culture vessel is then thoroughly rinsed with water and dried prior to use.

The disclosed methods can also include double-coating the culture vessels with an extracellular matrix protein. In an embodiment, the culture vessel is treated with laminin, fibronectin or a fibronectin derivative following the application of poly-L/D-ornithine or poly-L/D-lysine described above. In an embodiment, fibronectin protein prepared from human plasma is used. It should be appreciated, however, that any other suitable form or source of fibronectin protein can be used such as porcine or bovine fibronectin, recombinant fibronectin, fragments of fibronectin proteins, synthetic peptides, and other chemical mimetics of fibronectin. In an embodiment, between about 0.1 µg/mL to about 1 mg/mL of laminin or fibronectin can be applied.

In certain embodiments, the present composition comprises matrigel, ECM or a combination thereof. In certain embodiments, the matrigel and ECM have a molecular weight (or weight average molecular mass, or average molecular mass) ranging from about 25,000 dalton (Da) to about 40,000 dalton, from about 25,000 dalton to about 50,000 dalton, from about 40,000 dalton to about 50,000 dalton, from about 40,000 dalton to about 100,000 dalton, from about 50,000 dalton to about 100,000 dalton, from about 100,000 dalton to about 200,000 dalton, from about 100,000 dalton to about 250,000 dalton, from about 80,000 dalton to about 200,000 dalton, from about 150,000 dalton to about 200,000 dalton, from about 100,000 dalton to about 150,000 dalton, or from about 50,000 dalton to about 500,000 dalton or from 400,000 dalton to about 900,000 dalton. In certain embodiments, the laminin is 400k-900k dalton.

In certain embodiments, matrigel and ECM have an isoelectric point (pI) ranging from about 4.5 to about 9, from about 5 to about 9, from about 5 to about 7, from about 6 to about 7, from about 5 to about 6, from about 7 to about 9, or from about 4.7 to about 5.2.

In certain embodiments, matrigel and ECM are derived from raw materials including, but not limited to, the skin, bones, connective tissues, tendons, ligaments, etc. of animals such as cattle, chicken, pigs, and fish. In one embodiment, matrigel and ECM are of bovine source, porcine source, rodent (mouse or rat) source or a combination thereof.

In certain embodiments, the present composition may further comprise amino acids (0.01-1 g/L), vitamins (1 ug-1 g/L), glucose (1-10 g/L), cytokines, lipids, growth factors, antibiotics (e.g., penicillin, streptomycin, etc.) (1 Unit-500 Units/mL), antimycotics, steroid hormones, protein hormones, serum (0.2-10% v/v), proteins, salts (0.1 ug-10 g/L), formamide, methoxylated compounds, and/or polymers (e.g., polyvinyl pyrrolidone and polyvinyl alcohol.

In certain embodiments, the present composition further comprises one or more salts, including inorganic salts, and/or organic salts. Non-limiting examples of inorganic salts include, potassium chloride, sodium bicarbonate, sodium chloride, and sodium phosphate monobasic, potassium phosphate monobasic, potassium phosphate dibasic, sodium bicarbonate, calcium chloride, magnesium chloride, potassium bicarbonate, potassium monophosphate, and combinations thereof. In certain embodiments, the salt is at a concentration of 0.1 ug-10 g/L. In certain embodiments, the composition does not comprise serum.

5.7 Cell Viability

As used herein, the term "viability" refers to the percentage of viable cells (e.g., based on an intact cell membrane system). In certain embodiments, viable cells are metabolically active or would become metabolically active after their release to a suitable culturing condition.

In certain embodiments, the viability of the neuronal cells is at least about 50%, at least about 55%, at least about 60%, at least about 65%, at least about 70%, at least about 75%, at least about 80%, at least about 85%, at least about 90%, or at least about 95%.

In certain embodiments, the present compositions and methods ensure that the cells display a limited amount of, or minimal, necrosis and apoptosis in culture. In certain embodiments, necrosis and/or apoptosis is observed in less than about 25%, less than about 20%, less than about 15%, less than about 10%, less than about 5%, or less than about 1% of the cells.

Cell viability can be measured by any methods known in the art. In certain embodiments, cell viability is measured using a Trypan blue internalization test or by measuring propidium iodide uptake. In certain embodiments, cell viability is measured by assaying the ability of cells to attach efficiently (e.g., the attachment assays). In certain embodiments, proliferation assays can be used to determine if the attached cells can proliferate as expected. Attachment and proliferation efficiency can be compared to control cells.

For neuronal cells, the methods described herein may further ensure that the neuronal cells maintain their characteristics. This can be established by the determination of specific expression of markers using RT-PCR.

5.8 Method and Apparatus

The present disclosure provides method and apparatus for directed growth of axons and dendrites in a 3D cell culture which are useful as a model to study axonal pathfinding, target cell selection, synapse formation, synaptic physiology, neuronal plasticity, drug screening and gene perturbations. As axon growth and neurite extension process in cell cultures is often stochastic and rely on random chance that any two cultured neurons may establish the physical contacts necessary to develop synapses. The present disclosure provides a reliable tool to culture neuronal cells under strategically directed growth conditions along alternating electric field produced by a well-defined array of electrodes embedder in a 3D culture. In certain embodiments, the neuronal cells are directed to grow in search of target cells. In certain embodiments, the 3D culture comprises growth enhancing molecules such as Schwann cells, chemical agents (e.g., chemical, trophic, substrate adhesion molecules or a combination thereof), and optionally a patterned deposition of a chemical agent in a 3D scaffold. The present disclosure also allows study of the mechanisms by which growth cones of developing or injured neurons find their path en route towards their targets and how this growth is affected by extrinsic factors. This information is important for designing strategies that would be required for successful regeneration after nerve injuries in mammals.

The present disclosure provides a system for directed growth of neurons, the system comprises: culturing the neurons on a 3D scaffold; providing growth enhancing molecules, trophic factors and nanoparticles on the 3D scaffold in a culture medium; applying an alternating electrical field to the neurons thereby stimulating the neuron to grow. In certain embodiment, the axon connects (i.e., forms a synapse with) another neuron. In one embodiment, the present disclosure provides a system that ensures the rapid and directed growth of axons and dendrites.

In one embodiment, the apparatus comprises providing an alternating electric field on neuronal network of neuronal cells in a 3D culture. In one embodiment, the apparatus comprises an electric field sensor for monitoring neuronal cell electrical activity.

5.9 Kits

The present disclosure also provides for a kit. Such a kit may include one or more containers comprising: (i) neuronal cells; (ii) a 3D scaffold with embedded metal wires in a culture medium; and (iii) an adaptor for connecting the metal wires with an alternating electric field. In one embodiment, the kit comprises the neuronal cells as disclosed herein.

In some embodiments, the kit can comprise instructions for use in any of the methods described herein. The kit comprises an instruction for modulating neuronal network activities. In one embodiment, the kit comprises an instruction for synchronize oscillations of a random neuronal network. In one embodiment, the kit comprises an instruction for directed growth of neurons. In one embodiment, the kit comprises an instruction for identifying an agent that modulates neuronal network activities or directed growth. The kit may further comprise a description of selecting a subject suitable for treatment based on identifying whether the subject is in need of the treatment. In some embodiments, the instructions comprise a description of administering the neuronal cells to a subject who is in need of the treatment. In certain embodiments, instructions supplied in the kits are typically written instructions on a label or package insert. The label or package insert may also indicate clinical and/or research applications of the neuronal cells.

The kits provided herein are in suitable packaging. Suitable packaging includes, but is not limited to, vials, bottles, jars, flexible packaging, and the like. Also contemplated are packages for use in combination with a specific device, such as a culture dish.

The kits optionally may provide additional components such as buffers and interpretive information. Normally, the kit comprises a container and a label or package insert(s) on or associated with the container. In some embodiment, the disclosure provides articles of manufacture comprising contents of the kits described above.

Also provided is a cell culture chamber or a device comprising the composition of the present disclosure.

5.10 Methods of Treatment

The present invention is useful in various methods of treatment. The present method comprises the step of administering the composition to a subject (e.g., a patient). Cellular therapy, or cell therapy, generally encompasses transplantation of human or animal cells to replace or repair damaged tissue and/or cells. Cell therapy has been used to repair spinal cord injuries and help patients with neurological disorders such as Alzheimer's disease, Parkinson's disease, and epilepsy.

The present invention can be used in applications where it is useful to grow cells for a period of time for use in later cell therapies. This can include growing a patient's own cells for later transplantation, as well as for use in research or therapies. The disclosed methods include the use of neuronal cells to ameliorate a neurodegenerative condition. In one embodiment, the neuronal cells of the disclosed methods may include pre-differentiated neuronal cells for transplantation. In one embodiment, for maximum yield of the cells and for simplicity of the procedure, a confluent culture is harvested for transplantation which comprises primarily a population of differentiated and undifferentiated cells.

The neuronal cells in the disclosed methods can be derived from one site and transplanted to another site within the same subject as an autograft. Furthermore, the neuronal cells in the disclosed methods can be derived from a genetically identical donor and transplanted as an isograft. Still further, the neuronal cells in the disclosed methods can be derived from a genetically non-identical member of the same species and transplanted as an allograft. Alternatively, neuronal cells can be derived from non-human origin and transplanted as a xenograft. With the development of powerful immunosuppressant, allograft and xenograft of non-human neural precursors, such as neural precursors of porcine origin, can be grafted into human subjects. Cell therapy typically involves the injection of either whole cells or cell extracts that are xenogenic, allogenic (from another human donor), or autologous (wherein the cells are extracted from and transplanted back into the same patient).

The disclosed methods can generate and maintain a large numbers of neurons in vitro. While most of the neuronal cells are differentiated as produced by the presently disclosed method, when the neuronal cells are not differentiated prior to transplant, the neuronal cells can proliferate up to two to four cell divisions in vivo before differentiating, thereby further increasing the number of effective donor cells. Upon differentiation, the neurons secrete specific neurotransmitters. In addition, the neurons secrete into the surrounding area of the transplant in vivo growth factors, enzymes and other proteins or substances which are beneficial for different conditions. Accordingly, a variety of conditions can be treated by the disclosed methods because of the ability of the implanted cells to generate neurons in vivo and because the neurodegenerative conditions may be caused by or result in missing elements including neuron-derived elements. Therefore, subjects suffering from degeneration of CNS tissues due to lack of such neuron-derived elements, such as growth factors, enzymes and other proteins, can be treated effectively by the disclosed methods.

The present invention also provides methods for transplanting neuronal cells into a subject using the cultured neuronal cells for transplantation. In some embodiments, the transplanted neuronal cells are xenogenic to the non-human animal. In some embodiments, the transplanted neuronal cells are human cells.

Disclosed herein are methods for treating neurodegenerative disease, including but not limited to, Alzheimer's disease, Parkinson's and Huntington's disease by transplantation of neural cells. The present disclosure provides methods include identifying, isolating, expanding, and preparing the donor cells to be used as treatment of the neurodegenerative condition. The donor cells to be transplanted can be selected to correspond to the elements or lack thereof that contributes to the condition, its symptoms and/or its effects.

The cells of the disclosed methods include cells that, upon transplantation, generate an amount of neurons sufficient to integrate within the neuronal infrastructure to ameliorate a disease state or condition. Disclosed herein are methods including treating neurodegenerative diseases or conditions by transplanting neuronal cells isolated from the central nervous system of a mammal and that have been expanded in vitro. For example, transplantation of the neuronal cells can be used to improve ambulatory function in a subject suffering from spasticity, rigidity, seizures, or paralysis.

A method of treatment can include supplying to an injured neural area, via transplantation, a suitable number of neuronal cells to attenuate defective neural circuits, including hyperactive neural circuits.

In one embodiment, the disclosed method includes restoring motor function in a motor neuron disease. A suitable number or a therapeutically effective amount of neuronal cells can be provided to at least one area of neurodegeneration, such as a degenerative spinal cord, to restore motor function. The neuronal cells exert their therapeutic effect by replacing degenerated neuronal cells. In some embodiments, the neuronal cells exert their therapeutic effect by expressing and releasing trophic molecules which protect the neurons of the degenerating tissue so that more of them survive for longer period of time. Neuronal cells can be prompted to project into ventral roots and innervate muscle where they engage in extensive reciprocal connections with host motor neurons in subjects with degenerative motor neuron disease. Neuronal cells can be grafted into the lumbar cord where these cells can form synaptic contacts with host neurons and express and release motor neuron growth factors.

The disclosed methods include providing neuronal cells that integrate with the host tissue and provide one or more growth factors to the host neurons thereby protecting them from degenerative influences present in the tissue. The methods include introducing a sufficient number of neuronal cells to an area of a spinal cord such that an effective amount of at least one growth factor is secreted by the neuronal cells.

The disclosed methods include providing a method for using animal models in the preclinical evaluation of stem cells for cell replacement in neurodegenerative conditions.

The cells can be either undifferentiated, pre-differentiated or fully differentiated in vitro at the time of transplantation. In one embodiment, the cells are induced to differentiate into neural lineage. The cells of the disclosed methods can undergo neuronal differentiation in situ in the presence of pro-inflammatory cytokines and other environmental factors existing in an injured tissue.

Using the disclosed methods, neural circuits can be treated by transplanting or introducing the cells into appropriate regions for amelioration of the disease, disorder, or condition. Generally, transplantation occurs into nervous tissue or non-neural tissues that support survival of the grafted cells. Neuronal cell grafts employed in the disclosed methods survive well in a neurodegenerative environment where the neuronal cells can exert powerful clinical effects in the form of delaying the onset and progression of neurodegenerative conditions or disease.

In some instances, transplantation can occur into remote areas of the body and the cells can migrate to their intended target. Accordingly, the disclosed methods can also include partial grafting of human neuronal cells. As used herein, the term "partial grafting" can refer to the implantation of expanded neuronal cells in only a portion of an area or less than an entire area of neurodegeneration. For example, partial grafting of human neuronal cells into the lumbar segments of spinal cord. At least a portion of the effects of neuronal cells on degenerating motor neurons include delivery of neurotrophins and trophic cytokines to degenerating host motor neurons via classical cellular mechanisms.

As used herein, a neurodegenerative condition can include any Disease or disorder or symptoms or causes or effects thereof involving the damage or deterioration of neurons or the nervous system. Neurodegenerative conditions can include, but are not limited to, Alexander Disease, Alper's Disease, Alzheimer Disease, Amyotrophic Lateral Sclerosis, Ataxia Telangiectasia, Canavan Disease, Cockayne Syndrome, Corticobasal Degeneration, Creutzfeldt-Jakob Disease, Huntington Disease, Kennedy's Disease, Krabbe Disease, Lewy Body Dementia, Machado-Joseph Disease, Multiple Sclerosis, Parkinson Disease, Pelizaeus-Merzbacher Disease, Niemann-Pick's Disease, Primary Lateral Sclerosis, Refsum's Disease, Sandhoff Disease, Schilder's Disease, Steele-Richardson-Olszewski Disease, Tabes Dorsalis or any other condition associated with damaged neurons. Other neurodegenerative conditions can include or be caused by traumatic spinal cord injury, ischemic spinal cord injury, stroke, traumatic brain injury, and hereditary conditions.

The conditions which may be treated as disclosed herein may derive from traumatic spinal cord injury, ischemic spinal cord injury, traumatic brain injury, stroke, multiple sclerosis, cerebral palsy, epilepsy, Huntington's disease, amyotropic lateral sclerosis, chronic ischemic, hereditary conditions, or any combination thereof.

As disclosed herein, introducing the therapeutically effective amount of the neuronal cell population may include injecting at least a portion of the therapeutically effective amount into a plurality of areas of the recipient spinal cord.

In one embodiment, the method comprises treatment of chronic pain.

The cell density for administration can vary from about 1,000 cells per microliter to about 1,000,000 cells per microliter depending upon factors such as the site of the injection, the neurodegenerative status of the injection site, the minimum dose necessary for a beneficial effect, and toxicity side-effect considerations. In an embodiment, the disclosed methods include: injecting cells at a cell density of about 5,000 to about 50,000 cells per microliter.

The volume of media in which the expanded cells are suspended for delivery to a treatment area can be referred to herein as the injection volume. The injection volume depends upon the injection site and the degenerative state of the tissue. More specifically, the lower limit of the injection volume can be determined by practical liquid handling of viscous suspensions of high cell density as well as the tendency of the cells to cluster. The upper limit of the injection volume can be determined by limits of compression force exerted by the injection volume that are necessary to avoid injuring the host tissue, as well as the practical surgery time.

In one embodiment, the method of treatment comprises applying electric field of alternating polarity and changing frequencies directly to neuronal cells in a subject. In certain embodiments, the neuronal cells subjected to the method of the present disclosure has directed growth and form synapses with other neurons to establish a neural network.

5.11 Screening Assays

Due to the limitations of the ability to design effective screening tools, individualized therapy has been difficult to achieve using the culture methods currently available. The 3D neural culture system described herein offers a unique opportunity to combine methodologies to accurately deliver a diagnostic screening tool as well as to deliver an individualized therapy. Upon isolation of a patient's brain tissue, neuronal cells from the brain tissue can be grown and maintained in the 3D culture system provided. The neuronal cells may be observed and tested for any abnormal phenotypes and a diagnosis may be made. The neuronal cells would then be screened for their resistance and susceptibilities to various known (and potentially novel) therapeutics to assess the best therapy for the patient.

Insofar as is known, drug screening for neural disorders has not been done to date in 3D models. Information and insights gained will guide future human clinical trials.

The present disclosure provides three-dimensional neural cell culture systems for the screening and development of diagnostic and therapeutic agents having efficacy for the treatment of aberrant neural disorders as discussed above, including without limitation, epilepsy. Aberrant neural disorders may be manifested through abnormal response to synchronization or asynchronization, directed growth signals from external alternating electric field.

In one embodiment, the present disclosure provides a well characterized 3D neural cellular model which recapitulates directed growth and maintenance of neuronal cells from brain tissue to facilitate the identification of agents having efficacy against neural diseases. Moreover, such models can be individualized to identify those most likely to benefit and to further create personalized therapy regimens that are appropriate to the patient being treated. Accordingly, provided herein is a cell culture-based system which exhibit disease state of neuronal cell development.

In certain embodiments, the present method is used for screening such as but are not limited to, drug efficacy and/or toxicity screenings, investigative/mechanistic toxicology, target discovery/identification, drug repositioning studies, pharmacokinetics and pharmacodynamics assays.

Thus, another aspect of the present disclosure comprises a method of use of the cultures described above in a screening method to identify agents which modulate the ability of neural cells directed growth and the ability of the neuronal cells to respond to external alternating electric filed.

In yet another embodiment, mature brain tissue are placed in culture as described above and subjected to the methods disclosed herein. Patient specific cultures such as these provide the means to identify and streamline diagnostic and therapeutic approaches.

While the methods described herein can be used for all neuronal cell types, a well characterized 3D neuronal cell model which recapitulates neural disorders is described herein which will assist in the identification of agents have efficacy against this disease.

In certain embodiments, multi-well plate assays (e.g., 384 wells) may be used to test compounds that specifically impair neural disorders. For example, bioluminescence assays would be employed in each well as read outs for markers related to neural disorders. Identification of agents which disrupt neural cell growth and maintenance is particularly desirable. A combinatorial chemistry approach will be employed to identify molecules with greatest activity and then iterations of these molecules will be developed for further cycles of screening. These assays should facilitate identification of therapeutic agents for their ability to modulate neural cell growth and maintenance. Such agents include, without limitation, nucleic acids, polypeptides, small molecule compounds, peptidomimetics. In certain embodiments, candidate agents can be screened from large libraries of synthetic or natural compounds. The skilled person is aware of other sources and can readily purchase the same. Once therapeutically efficacious compounds are identified in the screening assays described herein, they can be formulated into pharmaceutical compositions and utilized for the treatment of neural disease.

Also provided herein is a method for identifying a candidate agent that modulates neuronal cell activity, said method comprises: contacting a neuronal cell culture with a candidate agent, wherein said neuronal cell culture comprises a 3D culture of neuronal cells; and assaying the neuronal cell culture for neuronal activity in the presence of said candidate agent, wherein said assaying for neuronal activity comprises comparing said neuronal activity in the presence of said candidate agent to neuronal activity in the absence of said candidate agent, wherein a change in said neuronal activity indicates that the candidate agent modulates neuronal cell activity.

In some embodiments, the neuronal cells are assayed for neuronal activity. In certain embodiments, the assay involves staining the neuronal cells with an agent that binds specifically to a neuronal cell process. In some embodiments, the neuronal cell process is a dendrite or an axon. In certain embodiments, the neuronal cells are transfected with a gene of interest encoding a detectable molecule and the neuronal cells are assayed for neuronal activity by detecting the detectable molecule. In certain embodiments, the neuronal activity comprises growth of a neuronal cell process. In some embodiments, the neuronal cell process is a dendrite or an axon. In certain embodiments, the detectable molecule is a fluorescent protein optionally under the control of a conditional promoter.

The following are examples of the present invention and are not to be construed as limiting.

6. EXAMPLES

The experimental setup of the present disclosure comprises dissociated cortical neurons growing on a silk fibroin film with embedded gold wires.

6.1 Stimulation Strategy

Electrical field was imposed to cortical neurons by a pair of substrate-embedded gold wires spanning the in vitro culture (FIG. 1A). FIG. 1A shows a biphasic, rectangular wave. FIG. 1A shows the simulated EF distribution by the COMSOL software, as described previously (Tang-Schomer et al., 2014c). The biphasic wave introduced EF of alternating polarity during the positive and negative phases of the wave function, at the rate of the wave frequency.

In conventional stimulation experiments, the parameters of stimulus (amplitude, frequency, duration) are determined by paring with intracellular recording of evoked responses of targeted neurons (Bagley and Westbrook, 2012; Jayakar et al., 1992). This study used voltage (160 mV across 6 mm) that showed in a similar system frequency-dependent calcium responses of cortical neurons (Tang-Schomer et al., 2014a; Tang-Schomer et al., 2014c). Our setup generated a theoretical EF strength of 27 mV/mm, above the threshold extracellular voltage gradient of 5-10 mV/mm for evoked neuronal response (Jefferys, 1995).

6.2 Network Analysis and Unsupervised Community Detection

A local greedy-optimization algorithm was used to automatically determine the best partition of the neuronal population (i.e., the best number of communities and composition of each community) with minimal computational cost (FIGS. 1B-C). We defined the communities returned by the algorithm as functional clusters as the neurons within the community had fluorescence time series with high degree of temporal correlation.

Specifically, we envisioned each neuron in the culture as a node in a fully connected network, i.e., we assumed an edge between nodes, i,j, for all i,j=1, 2, 3, . . . , N, where N is the number of labeled neurons in the culture (FIG. 1B). For each pair (i,j), a weight $w_{i,j}$ was assigned to the edge between i and j, with $w_{i,j}$ being the Pearson correlation coefficient between the normalized fluorescence intensity time series estimated for neuron i and j, respectively. The functional network is univocally defined by the weighted adjacency matrix (Newman, 2010)

$$A = \begin{bmatrix} 0 & w_{1,2} & \cdots & w_{1,N} \\ \vdots & & \ddots & \vdots \\ w_{N,1} & w_{N,2} & \cdots & 0 \end{bmatrix} \quad (1)$$

which is a N×N symmetric matrix and has zeros on the main diagonal because no node forms edges with itself. We applied static community detection (Newman, 2010) on A to identify meaningful group structures in the neuronal network. A community is a set of nodes (i.e., cultured neurons) that are connected among one another more densely than they are to nodes in other communities, and nodes within a community may share similar structural or functional properties (Newman, 2010).

We used the Louvain algorithm (LA) (Blondel et al., 2008) to partition matrix A in communities (FIG. 1C). Briefly, LA identifies communities in a network by optimizing a quality function known as "modularity index" Q (Newman, 2010), which measures the density of edges inside the communities compared to edges between communities. Communities are estimated by comparison between the assigned network and a null model (Newman-Girvan null model)(Newman, 2010) and high modularity index values indicate large separation between communities. Because LA is a locally greedy optimization algorithm, we ran the community detection procedure for a total of 100 optimizations and used a consensus partition method (Lancichinetti and Fortunato, 2012) to obtain a consistent community partitioning in each network. After the functional clusters were determined, individual neurons were color-coded accordingly onto the original fluorescence image, to compare with their physical partitioning.

6.3 Network Synchronization Under Alternating EF with Increasing Frequencies When we monitored cortical cultures without stimulation for 10 minutes at a time, no oscillatory calcium responses were found, and calcium signals fluctuated within 20% of the baseline level. Cortical cultures under alternating EF of a constant frequency also failed to produce synchronized activities.

To our surprise, when biphasic, rectangular waves with field polarity alternating from 0.2 Hz to 200 Hz were applied, large-scale, synchronized oscillations of cortical neurons were observed (FIGS. 2A-E). FIG. 2A shows the example of neurons stained with fluo4, a calcium indicator, adjacent to a silk film-embedded gold wire electrode (field of view, 750 by 750 µm).

FIG. 2B shows the stimulation protocol of alternating EF with increasing frequencies and the average calcium signal time series of the cortical culture. The experiment was conducted in a temperature controlled (37° C.) environmental chamber and lasted for less than 1 hour. Stimulus was introduced at the 3rd minute of live imaging and increased from 0.2 Hz by 10-fold a time to 200 kHz for 6 minutes per condition. The average calcium signal showed synchronous oscillations of ~12 minutes wave length (70 neurons measured).

The community detection algorithm was used to sort the neurons based on the statistical significance of the differences of their calcium signals, and two clusters were identified (FIG. 2C). Neurons in the same cluster were highly correlated (i.e., Pearson's correlation coefficient >0.5) (yellow). Neurons belonging to different clusters were either poorly correlated (i.e., Pearson's correlation coefficient close to 0) or negatively correlated (i.e., Pearson's correlation coefficient close to −1) (blue). Calcium signal time-series were then color-coded (FIG. 2D) according to whether they referred to neurons in Cluster 1 (black) or Cluster 2 (red). Cluster 1 contained "non-responders" with calcium signals fluctuating close to the baseline level. Cluster 2 contained "super-responders" with calcium signal increases >5 folds of the baseline level.

When mapped onto the original image, the functional clusters found remarkable match with the neurons' physical partitioning (FIG. 2E). Neurons belonging to the same functional cluster resided in close proximity to each other, and separate from neurons belonging to the other cluster (Cluster 1, non-responders, white; Cluster 2, super-responders, red).

6.4 Entrainment of Sub-Populations' Oscillations by Network Synchronization

By manual examination of calcium signal traces, we further divided the apparent "non-responders" into two groups, modest-responders with <5-fold signal changes but displaying synchronized activities, and the rest as noisy-responders. When mapped onto the original image, these sub-populations were found to belong to distinctive physical groups (FIG. 3A): the super-responders and modest-responders as two separate neuronal aggregates (in red and white circles, respectively), and the noisy-responders consisting cells dispersed in the surrounding areas (arrows). FIGS. 3B.-G. display representative images at specific time-points (in minute), demonstrating different fluorescence changes of neuronal sub-populations.

FIGS. 3H.-I. show the average calcium time series from super-responders (red, n=14, 20%), modest-responders (blue, n=17, 24%) and noisy-responders (black, n=39, 56%). The super-responders had peak signal levels of ~10-fold increases, compared to <2-fold changes of the other groups (FIG. 3H). Further close examination of the low-amplitude signal changes of the modest- and noisy-responders revealed that they, too, exhibited synchronized oscillations (FIG. 3I). Notably, all three sub-populations' oscillatory patterns were entrained by the network-level synchronous oscillation. The sub-population showed group-specific amplitude and phase patterns. For example, the modest-responders (blue) had opposite phase responses than the super-responders (red), i.e, peaks in one plot correspond to troughs in the other plot and vice versa. The noisy-responders' signal trace (black) had its major peaks in phase with other sub-populations, but contained two smaller peaks.

6.5 Symmetrical Phase Changes and Dependence on Group-Specific Spontaneous Activities To understand the phase differences between the super-responders and modest-responders, we examined individual calcium time series (FIGS. 3J-K, FIG. J, super-responder; FIG. K, modest-responder). The traces showed remarkable synchrony within each sub-population. The synchronous oscillations of the two groups exhibited opposite phase changes.

We then focused our analysis on the initial period of the experiment, when the culture was switched from being un-stimulated for the first 3 minutes to 0.2 Hz alternating EF for another 6 minutes. FIGS. 3L-M show the average calcium signal time series of the first 6-min (FIG. 1, super-responder; FIG. M, modest-responder). The two sub-populations had opposite activity trends prior to stimulation, with spontaneous calcium signal increases and decreases, respectively. There were significant differences of their signal levels at the $3^{rd}$ minute compared to the $1^{st}$ minute. Upon stimulation, the different calcium responses continued their opposite trajectory that were further enhanced by the 0.2 Hz EF. There were significant differences of the signal levels at 1 minute post-stimulation (the $4^{th}$ minute) compared to right before the stimulation (the $3^{rd}$ minute).

The above findings showed that a random network of cortical culture contained sub-populations of distinctive physical partitioning and endogenous activity levels. Alternating EF of increasing frequencies induced synchronization within each sub-population as well as across the entire network, while retaining group-specific oscillatory patterns. The binary response of activity increase or decrease contributed to the opposite phase patterns of different sub-populations.

6.6 Symmetrical Sub-Population's Oscillatory Patterns Under Alternating EF with Decreasing Frequencies Considering that applied EF of a constant frequency failed to induce network synchronization, we suspected that the context of EF frequency change was critical. We therefore conducted a different experiment, in which a different cortical culture was exposed to alternating EF of decreasing frequencies (FIGS. 4A-D). We applied biphasic, rectangular waves (peak-to-peak 160 mV) with frequencies starting from 200 kHz and decreased by 10-fold to 0.2 Hz for 6 minutes per condition. FIG. 4A shows the fluo-4 stained neurons adjacent to a silk film-embedded gold wire; the wire was right blow the imaged area outside the field of view.

FIG. 4B shows the average calcium time series (black dots) from 63 neurons measured. The mean activity level appeared to be mostly flat with a down-ward trend, with large variance of each data point. When we plotted the variance spread (FIG. 4B, crosses), measured as the ratio of standard derivation to the mean, a dependence on EF frequency was found. The baseline variance of 26% decreased to 7% after 5 min of 200 kHz stimulation, maintained at ~12% during 20 kHz stimulation, and rose progressively as the frequency decreased, until reaching 102% at the end of the experiment (total time <1 hr). These results suggested that there were mixed responses of different sub-populations, and functional association of these groups depended on EF frequency change.

We used the community detection algorithm to automatically group the 63 neurons into two functional clusters (FIG. 4C). Neurons within a cluster were highly correlated and poorly or negatively correlated to neurons in the other cluster, thus reflecting a marked functional separation between clusters. Color-coded calcium signal time series in FIG. 4D revealed cluster-specific signal patterns that were previously obscured in the total average trace (FIG. 4B). Cluster 1 (black) neurons had increased activity and Cluster 2 (red) neurons decreased activity. Notably, there was symmetry of plots between the two groups with peaks in one group corresponded to troughs of the other group.

6.7 Suppression of Spontaneous Activity by High Frequency Alternating EF

To understand the differences between Cluster 1 and 2, we mapped individual neurons onto the original image (FIG. 5A, Cluster 1 in white. Cluster 2 in red). The functional clusters matched neuronal physical groups, as neurons belonging to the same cluster were located in proximity to one other and separate from the other cluster. FIGS. 5B-F display representative images at specific time-points, demonstrating different fluorescence changes of neuronal sub-populations. FIG. 5G shows the average calcium time series of the two clusters (Cluster 1, black. Cluster 2, red), demonstrating group-specific oscillatory patterns. Both clusters started with opposite spontaneous activity changes (increase versus decrease), had suppressed activities during 200 kHz and 20 kHz stimulation, and continued with opposite activity changes with regard to amplitude and phase patterns as the frequency decreased.

We then examined the differences of the two sub-populations during the initial period of the experiment (FIGS. 5H-I), when the culture was switched from being unstimulated for the first 3 minutes to under 200 kHz alternating EF stimulation for another 6 minutes. Cluster 1 (FIG. 5H) and Cluster 2 (FIG. 5I) neurons had calcium signal increase of 15±6% (n=33, p<0.01)) and decrease of 36±10% (n=30, p<0.01), respectively, at the $3^{rd}$ minute compared to the $1^{st}$ minute. Upon stimulation of 200 kHz alternating EF, the opposite calcium signaling trends were attenuated, and both sub-populations headed towards the baseline level.

6.8 Network Desynchronization Under Alternating EF with Decreasing Frequencies

By closer examination of each neuron's activity, we further divided the clusters into four groups, cluster 1a (n=20, 32%), 1b (n=13, 21%), 2a (n=16, 25%), 2b (n=14, 22%) (FIGS. 6A-F). FIG. 6A shows the general distribution of the sub-populations. Cluster 1a and 2a contained two well-separated neuronal aggregates. Cells interspaced in surrounding areas were contained in Cluster 1b and 2b. FIG. 6B shows each cluster's average calcium signal time series. The variance at each data point remained consistent within each group in contrast to the highly variable total average response in FIGS. 4C-F, indicating similar intra-group but different inter-group signal patterns. All clusters showed suppressed activities under 200 kHz and 20 kHz stimulation. However, starting from 2k Hz, there was great divergence of activity trends with group-specific oscillatory patterns as the frequency decreased. FIGS. 6C-F show pair-wise comparison of calcium signal time series. Striking symmetry was found between sub-population-specific oscillatory patterns, as highlighted in grey. Cluster 1a showed phase symmetry (i.e., peak versus trough) and opposite activity changes (i.e., increase versus decrease) with Cluster 2a (FIG. 6C) and Cluster 2b (FIG. 6D) under all frequencies (2 k-0.2 Hz). Cluster 1b showed symmetric phase and activity changes in specific frequency ranges, with Cluster 2b between 2 k to 20 Hz (FIG. 6E) and Cluster 1a at <2 Hz (FIG. 6F). Taken together, these behavior suggested a network de-synchronization process. The initial globally suppressed network diverged into two groups, Cluster 1 and 2 with opposite activity trends and phase patterns. As the alternating EF frequency decreased, neurons in Cluster 2 split into subgroups of 2a and 2b with oscillations of synchronized phase patterns but different amplitudes. Neurons in Cluster 1 split into subgroups of 1a and 1b that initially had synchronized phase patterns and different amplitudes, but under further decreased EF frequency, exhibited opposite phase patterns.

6.9 Lack of Synchronized Activity Under EF without Polarity Change or Continuous Frequency Change To examine the role of EF polarity in network synchrony, we designed a different set of stimulation experiments with monophasic EF of similar frequency changes as the alternating EF (FIGS. 7A-E); different batches of cortical cultures were used. FIG. 7A shows wave function comparison of biphasic EF and monophasic pulse trains of a fixed 0.1 millisecond pulse duration. The pulse train captured the initial moment of field potential change upon each stimulus at the same frequency as the corresponding biphasic waves. However, the pulse trains lacked field polarity change of the biphasic waves.

Figures 7B, 7C:
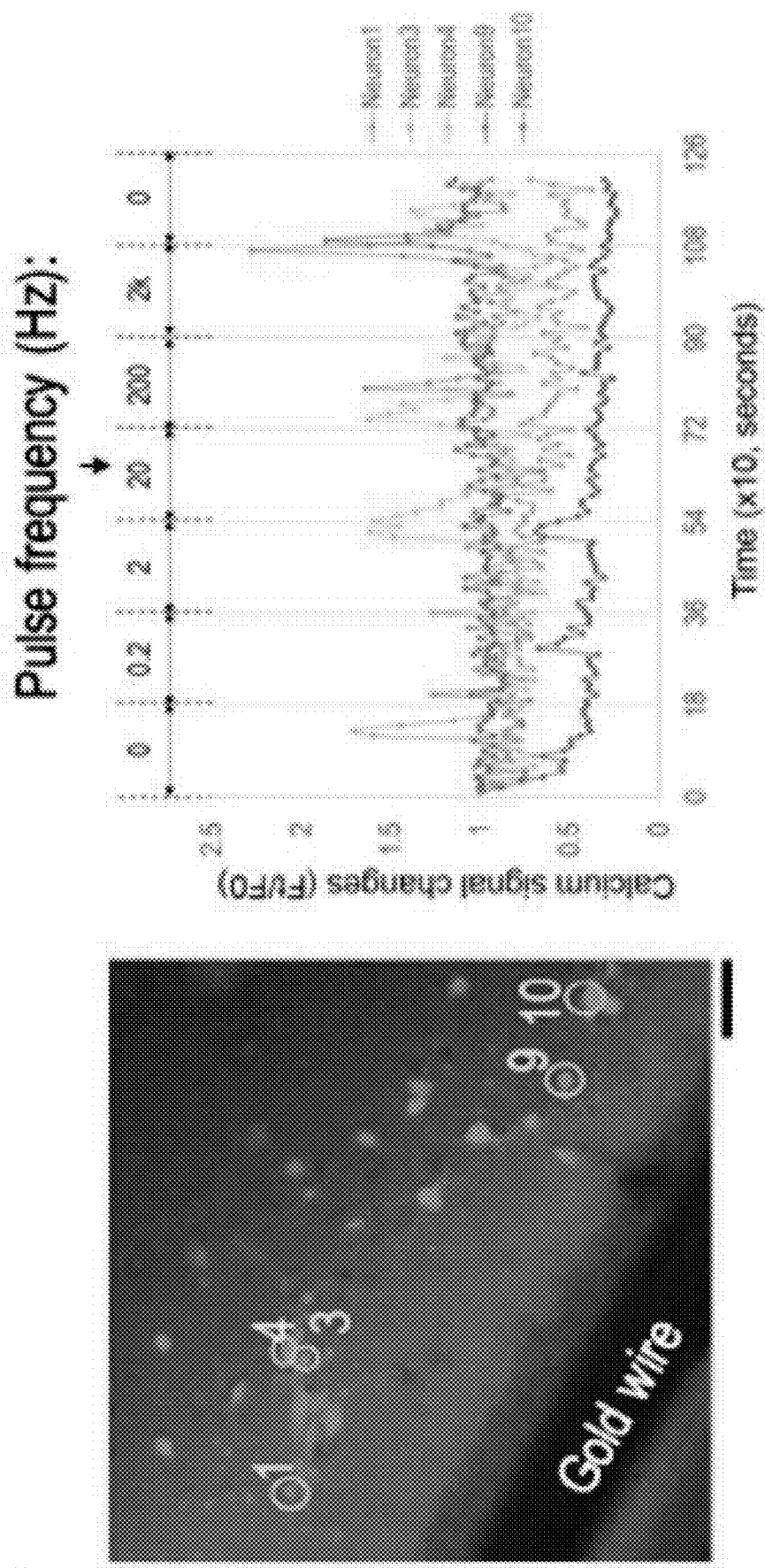
Figure 7E:
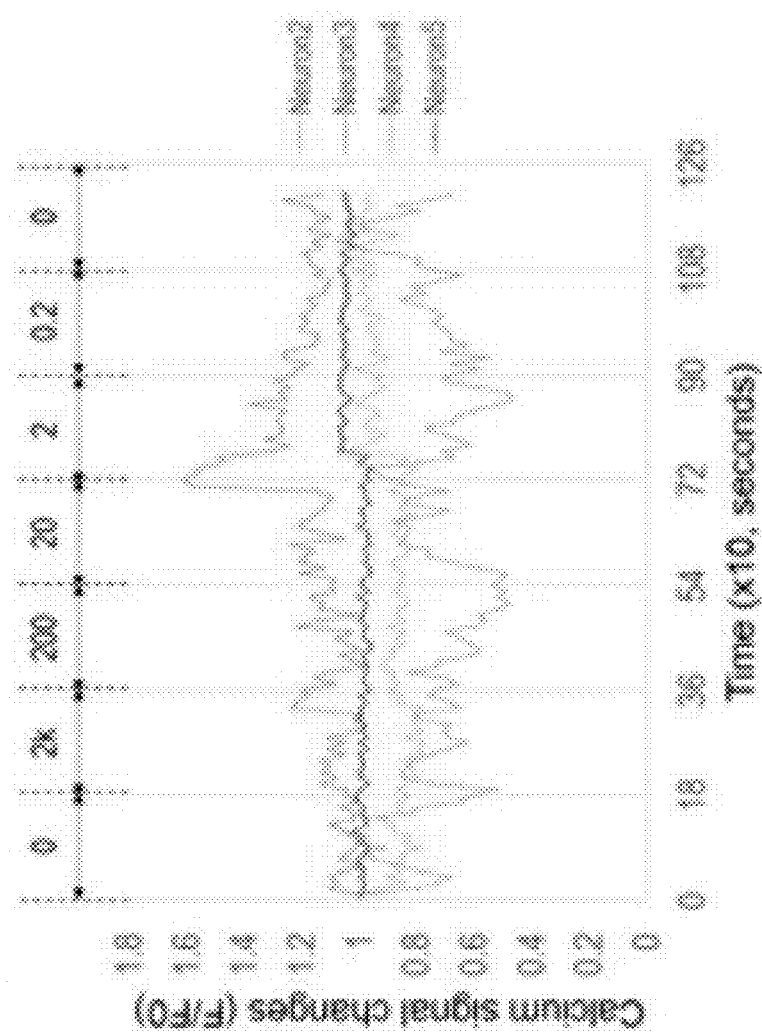
Figure 7D:
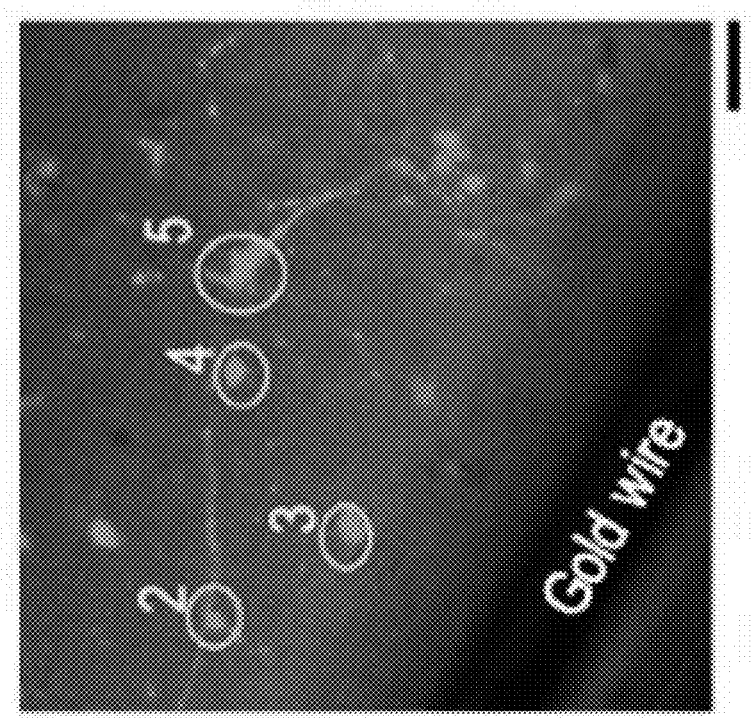

The pulse train was delivered at frequencies ranging from 0.2 Hz to 2k Hz for 3 minutes for each condition, and calcium fluorescence images were collected every 10 seconds. FIGS. 7B-E show fluorescence images of neurons (7B, 7D) and corresponding calcium time series (7C, 7E) under conditions of increasing frequencies and decreasing frequencies, respectively. In both scenarios, a majority of the neurons showed activity fluctuation within ~20% of the baseline levels, and only selective neurons with spiking activities as shown in FIGS. 7C and 7E (non-spiking activities were omitted). Statistical analysis of fluorescence intensity time series from individual neurons determined that neuronal activities in both scenarios were largely uncorrelated. Pearson's correlation coefficients between spiking neurons were close to 0, indicating that these neurons activated independently from one another.

In another set of experiments, we examined the role of frequency change by introducing a 3-minute zeroing period (i.e., no stimulation) in-between frequency changes of alternating EF; frequencies were changed from 0.2 Hz to 200 kHz or vice versa in similar orders as previous experiments (FIGS. 3A-M, 4A-D). Only a few random neurons showed spiking activities, and no synchronized oscillations were found (data not shown).

6.10 Hypothesis of Coordinated Stimulation by Alternating EF

Based on these findings, we proposed a hypothesis of network synchrony control by applied EF of alternating polarity (FIGS. 8A-E). Applied EF results in the polarization of the membrane of the nearby cells (Jefferys, 1995; Bikson et al., 2004; Radman et al., 2009). In general, neuronal elements are depolarized near cathode and hyperpolarized near anode. However, the spatial distribution of such polarization under a uniform EF is highly variable, depending on cell biophysics and morphologies (Yi et al., 2017; Bikson et al., 2004; Radman et al., 2009). By extending these concepts to a neuronal network, we hypothesized that different populations are depolarized under a same uniform EF, and that as the field polarity changes, the populations switch to the other activation state (i.e., hyperpolarization vs. depolarization). Therefore, biphasic EF would result in coordinated stimulation of neuronal populations.

As illustrated in FIG. 8B, two populations (1 and 2) with different EF threshold are located at different distances from a nearby electrode; the other electrode would be too far away to impose direct effect. When the electrode is cathode (left), population 1 is activated (in green, + indicating depolarization) and population 2 non-activated (in white, − indicating no change or hyperpolarization). When the electrode turns to anode (right), population 1 is in-activated and population 2 activated. FIG. 8C illustrates the resulting calcium transients upon neuronal activation (left for population 1; right for population 2). There would be a timed delay of the population activation, as the inverse of two times of the EF frequency. Control of the frequency (FIG. 8D) would provide a means to temporally associate or dissociate the two neuronal sub-populations' evoked activities.

FIG. 8E illustrates the hypothesized network synchrony control by EF alternating frequency. In vitro studies of random cortical networks have shown that repetitive, timed stimulation of loosely associated neurons can induce synchronized bursts of the neurons and their neighbors (Shahaf and Marom, 2001; Tateno and Jimbo, 1999). Increasing EF frequency would be analogous to repetitive stimulus with increasingly shorter timing. In addition, the wide range of frequencies could activate many sub-populations of different responsiveness. It would result in network synchrony (FIG. 8E, left). The initial response to the applied EF would depend on neurons' endogenous activities, as shown in FIG. 3D. Moreover, binary responses to EF (activity increase or decrease) would lead to symmetrical phase pattern, as shown in FIGS. 3A-M, 5A-I. Therefore, group-specific oscillations with different amplitude or opposite phase patterns would be expected (FIG. 8E, left, a, b, c).

Conversely, decreasing EF frequency could dissociate the endogenous activities of different neuronal sub-populations (FIG. 8E, right). High frequency EF is known to suppress neuronal activities (Wagenaar et al., 2004; Chao et al., 2005; Madhavan et al., 2006; Birdno and Grill, 2008), also shown in our studies with the initial 200 kHz stimulation (FIGS. 5H, I). As the frequency decreases, the timing between neuronal activation increases, and the sub-populations are less likely to fire together, resulting in divergent oscillatory patterns. Population-specific responsiveness could be the different amplitudes, for example, FIG. 8E-f versus g, or different phase patterns as d versus e.

6.11 Discussion

We presented results of the behavior of a random cortical network under applied electrical field. Each neuron's activity was captured by calcium live imaging and matched to its physical location in the network. Calcium signal time series were subjected to cluster analysis for unbiased detection of neuronal communities of similar activity patterns. Spatial and temporal associations of neuronal activities revealed large scale, synchronized oscillations of a random network under alternating EF of changing frequencies. EF without polarity change or frequency change failed to produce synchronized activities among neurons. These findings formed the basis of a hypothesized network control mechanism, involving coordinated stimulation of different sub-populations by alternating field polarity. Change of EF frequency was critical for control of the timed delay of group-specific activities, by associating or dissociating different sub-populations via frequency increases or decreases, respectively. These novel EF effects on random neuronal networks provide important understanding of network synchrony underlying brain functions and neuromodulation applications.

6.12 Neural Network Manipulation—System Setup and Analysis

A thin silk fibroin-based film with embedded gold wires provided the interface system for in vitro cortical cultures. Compared to rigid MEA substrates, the flexible and transparent silk film provides greater ease and superb compatibility with in vitro neuronal cultures (Tang-Schomer et al., 2014c) as well as in vivo brain implants (Tang-Schomer et al., 2014c; Kim et al., 2010). The wire embedding method simplifies interface fabrication compared to the lithographic process for surface electrodes (Tang-Schomer et al., 2014a), with excellent interface stability requiring no additional adhesives or bonding. Regarding signal transmission, the thin silk film (~5 μm) poses no significant barrier (>90% conductivity) (Hronik-Tupaj et al., 2013). The gold wire provides double layer capacitive charging (Brummer and Turner, 1977) and alteres the ionic composition near the electrode. By applying charge-neural biphasic field, potential pH buildup at the electrode-solution interface would be eliminated and field propagation increased at high frequencies (Wagenaar et al., 2004; Graves et al., 2011). These features support the use of silk film-based neural-electric interface as a suitable system for investigating EF effects on neural networks. Sorting activities onto source neurons and grouping them based on common behaviors are not trivial tasks (Morin et al., 2005). Recorded electrical signals have superior temporal resolution allowing for temporal correlation analysis, for example, the delay between stimulus and the first evoked pulse. Temporal correlation of these signaling events forms the basis for inferring functional association of distributed neuronal populations. In comparison, the temporal features of calcium signals are less sharp (Robinson et al., 1993), and slow fluorescence imaging further limits the temporal resolution. In this study, we used confocal 3D imaging to maximize captured neurons that took almost 1 minute for each z-stack. Calcium imaging provides undisputable spatial resolution and allows for the signal trace to be mapped to the source neuron. The individually traceable time series have provided a multi-dimensional picture of the network dynamics for each cell at each time point.

We used community detection in functional networks for the unsupervised identification of neuronal communities that, within a given culture, exhibit homogenous fluorescence-based discharge patterns. Community detection is an established area of network analysis (Newman, 2010), and it has been recently used to unravel structural and dynamical properties of complex neuronal networks such as the epileptogenic brain network in patients with drug-resistant epilepsy (Khambhati et al., 2015), circadian-clock-related networks of neurons in the suprachiasmatic nucleus (Park et al., 2016), and networks of ganglion cells from retina (Billeh et al., 2014). It should be noted, though, that community detection algorithms are typically applied to large (i.e., more than 1,000 nodes) networks while we used here the Louvain algorithm on small (i.e., up to 70 nodes) neuronal networks. As the size of the network grows, however, the community detection remains feasible. Locally-greedy, resolution-adaptive algorithms (Bassett et al., 2013) and null models (Newman, 2010) are available to guarantee fast neuron clustering, while avoiding the detection of spurious and statistically nonsignificant communities.

6.13 Point and Distributed Electrical Fields for Network Stimulation

Point-source pulse stimulation is the most commonly used modality in neurophysiology studies. Specific stimulation frequencies have been associated with functional responses, for example, hippocampal resting activity (5 Hz), long-term potentiation (LTP, 100 Hz, 1-3 s), long-term depression (LTD, 0.5-5 Hz for 5-30 min), or homeostatic synaptic depression (3 Hz, 12-24 h) (Larson et al., 1986; Staubli et al., 1999; Malenka and Bear, 2004; Goold and Nicoll, 2010).

As evident from the examples that follow, it is discovered that: 1) There were sub-population-specific responses to the same stimulus; 2) The initial evoked responses were dependent on group-specific endogenous activities prior to the stimulation; 3) The evoked response was binary (activity increase or decrease) upon stimulation. In addition, our study showed that time varying frequency, but not constant frequency, produced synchronized network activities.

However, evoking network synchrony with point stimulation would require pre-selecting a site for stimulation, matching the initiating stimulus with the selected neuron's responsiveness, and tailoring stimulus time series for each affected neuron (or ensembles) in the network. These tasks would be daunting, if not impossible, for a random network. Alternatively, distributed EF stimulation used in our study would allow different sub-populations to be activated simultaneously. Assuming that stimuli-induced changes are operated under the pathway-specific principle, group-specific responses would be paced by network-level changes. As such, intrinsic activity fluctuations would be expected to ride along a slower wave of network oscillation. Indeed, in both scenarios of alternating EF stimulation, the different group-specific calcium signal time series showed oscillatory patterns in synchrony with one other at a time scale (tens of minutes) much longer than previously reported neuronal activities (milliseconds). The oscillatory patterns were not precisely aligned with the temporal changes of stimulus, in part due to the crude temporal resolution (in minutes) used in the present disclosure. Nevertheless, it is interesting to note that the network-level oscillation had a wave length of ~12 minutes, about one round of frequency changes of 6 minute per frequency. Accordingly, our results imply that the network may not only respond to EF frequency and duration, but also to the change of EF frequency over a longer time scale.

6.14 Network Synchrony Under EF of Alternating Polarity at Changing Frequencies Disclosed herein is control of network synchrony with EF of alternating polarity and changing frequencies. Field polarity change was found to be essential for network synchronization, as monophasic fields of the same frequency changes failed to produce correlated activities among neurons (FIGS. 7A-E). Other systems have shown that temporal coordination of distributed neuronal activities establishes network synchrony (Singer, 1999). The alternating field polarity could introduce a timed delay of half period of the biphasic wave, and therefore, temporally coordinate the stimulation of different neuronal sub-populations in a network (FIGS. 8A-E). As illustrated in FIG. 8B, different sub-populations are activated with regard to the nearby electrode's status as cathode or anode. In vitro cortical cultures consist of many neuronal types with a wide range of sensitivities to EF as low as 5 mV/mm (Jefferys, 1995; Bikson et al., 2004). In general, neuronal elements are depolarized near cathode and hyperpolarized near anode. However, the spatial distribution of such polarization is modified by a neuron's complex morphology, summation of which would lead to either somatic depolarization or hyperpolarization (Yi et al., 2017). Neuronal sensitivities to different stimulus shapes were examined in Wagnenaar's studies using MEAs in cortical cultures (Wagenaar et al., 2004). It was found that the transition between the positive and negative phases is the most effective stimulus compared to other pulse shapes. Therefore, it is reasonable to assume different activation state of sub-populations that are dependent on their endogenous activities and location in the field.

Another key factor is change of polarity alternating rate, or the time differential of the EF frequency. Alternating EF of a constant frequency did not produce correlated activities among neurons, neither did introducing resting-periods in-between EF frequency changes. These results suggested that change of EF frequency was necessary for inducing large scale, synchronized activities of neurons. The hypothesis of coordinated stimulation by EF frequency-dependent timed delay could explain these findings (FIGS. 8D, E). Increasing the frequency of the biphasic wave would increase temporal correlation of the activation of different sub-populations, therefore, lead to time coordinated network activities. Conversely, when the frequency of EF polarity change decreases, different sub-populations would be less coordinated, resulting in more divergent activities with group-specific amplitude and phase patterns.

It seems unnecessary to increase the frequency up to 200 kHz, as high frequency stimulation is known to pace networks to refractory state (Wagenaar et al., 2005; Chao et al., 2005; Madhavan et al., 2006). It is possible that the induced synchronous oscillation could persist after reaching a frequency threshold. The present disclosure focused on neurons adjacent to the electrode (within 750 µm). Less response would be expected of the neurons in distant areas as there would be little voltage gradient in the middle of the culture. At present, it is unclear whether synchronous oscillation near the electrode can propagate to other part of the network. Detailed mapping of neuronal communities in relation to field polarity and strength will provide insights on how the network communicates changes.

6.15 Implications for Functional Modulation of Neural Networks

Synchronous oscillatory activity in the cerebral cortex plays a crucial role in implementing complex brain functions (e.g., memory, cognition) as well as encoding information (Buzsaki, 2006). Numerous studies, both in vitro and in vivo, have focused on the mechanisms that sustain oscillations and their synchronization as well as on the relationship between neural oscillations and network dynamics (e.g., for a review, see (Buzsaki and Draguhn, 2004)). Abnormal increments in synchronization are reported as a key component in chronic neurological disorders, e.g., Parkinson's disease and epilepsy, and in the impairment of decision-making capabilities (Tan et al., 2013; Ross et al., 2013; Cao et al., 2016; Broggini et al., 2016). Furthermore, a complex interaction between synchronized neural oscillations and electrical stimuli is involved in deep brain stimulation (DBS) therapies for Parkinson's, essential tremor, and dystonia (Gross and Lozano, 2000; Ferrucci et al., 2008), and in transcranial direct current stimulation (tDCS) therapies for Alzheimer's disease (Ferrucci et al., 2008) and stroke (Hummel et al., 2005). Our study demonstrates that widespread oscillations can be induced in a neural population in vitro by using a coordinated electrical stimulation paradigm with biphasic rectangular waves. Our solution may be used to recreate oscillatory conditions in vitro with a fine spatial and temporal resolution. The system provides an easy-to-use testbed for reproducing pathological oscillatory activities in large neural populations as well as studying the effects of exogenous inputs (e.g., chemical compounds or novel neuromodulation approaches) on neural oscillations.

6.16 Electrical Stimulation and Soluble Factors

Figure 9D:
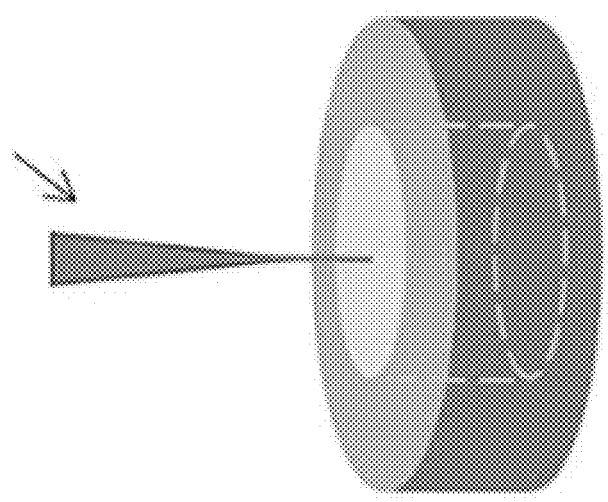

FIGS. 9A-D shows the schematics of the 3D brain tissue model (FIG. 9A) and approaches of delivering exogenous electrical signals (FIGS. 9B-C) or soluble factors (FIG. 9D). The 3D brain tissue is composed of silk protein material-based scaffold and infused extracellular matrix (ECM) gel, such as collagen type I gel used in this study, as described previously (Tang-Schomer, 2014, 2015). The center region of the donut-shaped scaffold is filled with ECM gel only, for axon outgrowth; whereas the cell bodies are confined to the scaffold region.

To apply an electric field (EF) (FIGS. 9B-C), a pair of thin gold wires (dia. 100 μm) were threaded into a 3D scaffold, abutting the central hole, in parallel with a distance close to 2 mm, and embedded within the collagen matrix. The placement of the wires was either horizontal (FIG. 9B) or vertical (FIG. 9C) to introduce different EF directions. The colored heat-map shows simulated EFs on the plane directly between the electrode pairs To introduce soluble factors (FIG. 9D), a 10 μL Hamilton syringe was used to deliver 1 μL drug solution into the center of a solidified 3D tissue model.

6.17 Axon 3D Growth at 24 hr after Electrical Stimulation

Axon growth at 24 hr after electrical stimulation (i.e., DIV 4) was compared, of varying frequencies at 0.5, 2, 20 and 200 Hz and 2 kHz (FIGS. 10A-J). In all samples, axons showed β III-tubulin stained extensions into the center core of collagen gel matrix (FIGS. 10A-H, representative immunofluorescence images of 2D projections). Interestingly, neurite outgrowth showed a preference of orientation towards the embedded electrodes. In samples with vertically placed electrodes, neurites aligned perpendicular to the electrode (FIG. 10B, bright field; 10C, fluorescence image; 10D, merged; the electrode marked with a dashed line). The electrode-preferred growth orientation was not affected by AC field frequencies, as shown in FIGS. 10E-H.

Figures 10F, 10G, 10H:
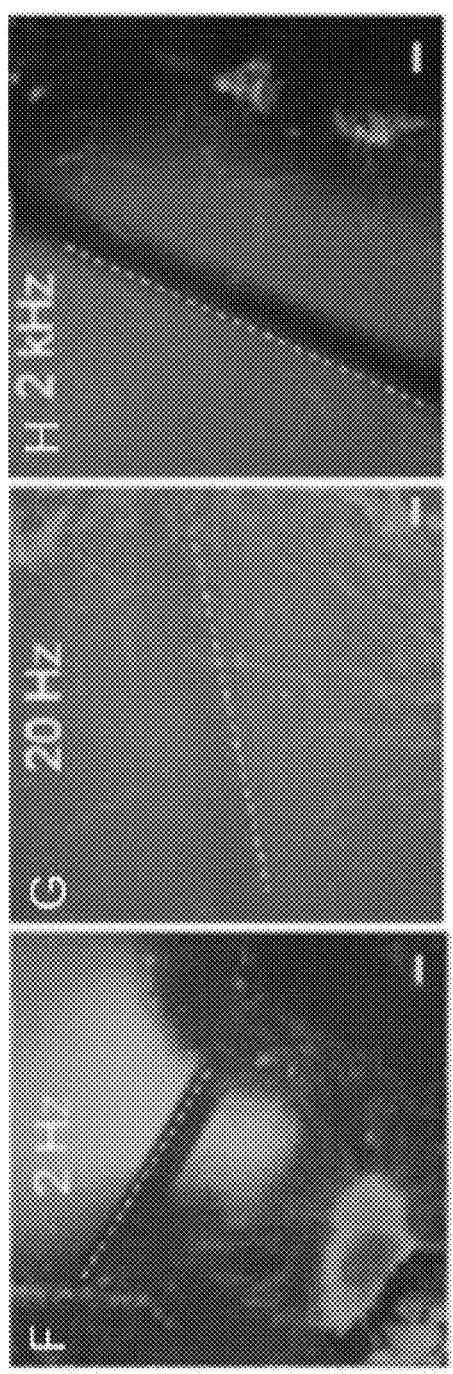
Figure 10E:
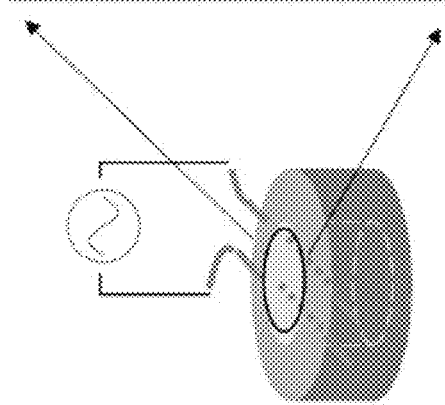
Figure 10I:
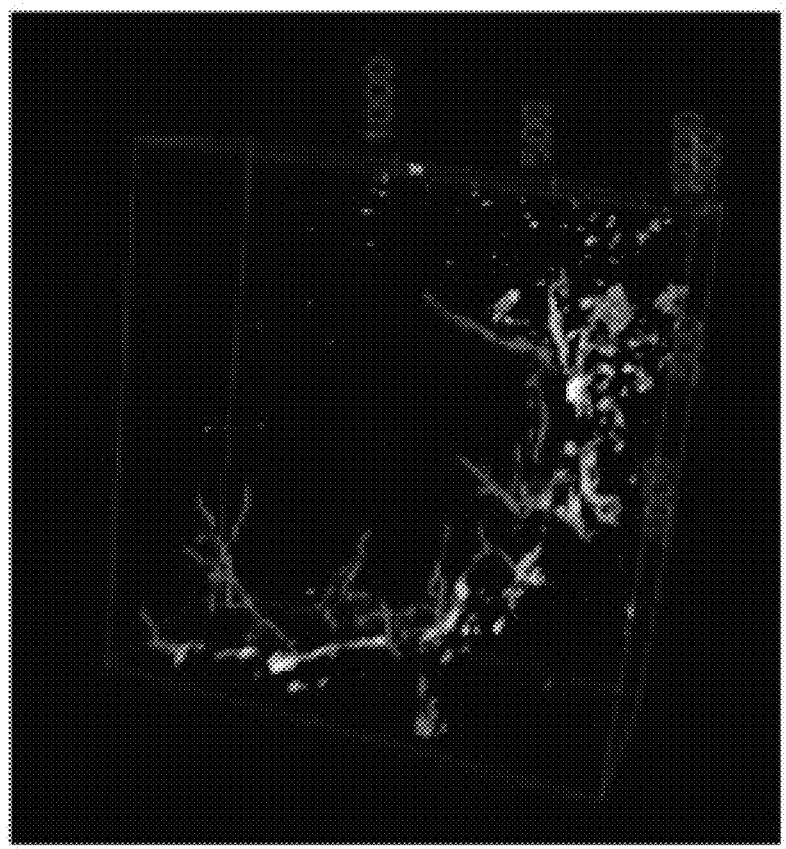
Figure 10J:
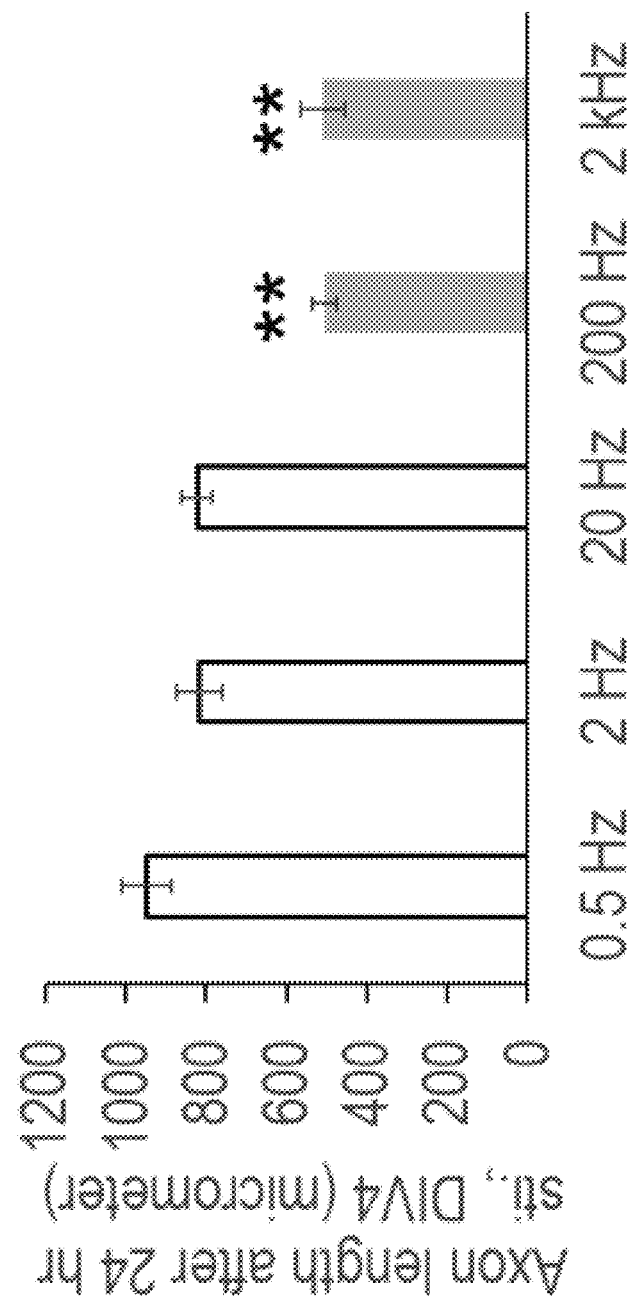

We used 3D neurite tracing to measure axon lengths in 3D (FIGS. 10J-J). FIG. 10I shows an example of 3D neurite tracing. Axon lengths at 0.5, 2, 20, 200 Hz and 2 kHz were 946.4±60.6 (n=41), 815.5±56.9 (n=28), 821.8±38.9 (n=87), 505.6±28.3 (n=20), 508.2±54.7 (n=10) μm, respectively (FIG. 10J). Axon lengths at 200 Hz and 2 kHz were significantly shorter than at 0.5, 2 and 20 Hz (Students' t-test, **, p<0.01), and neurons in 3D cultures under 2 kHz showed signs of cell death after 24 hr stimulation.

6.18 Axon 3D Growth Under Electrical Stimulation Up to DIV 7

Figure 11M:
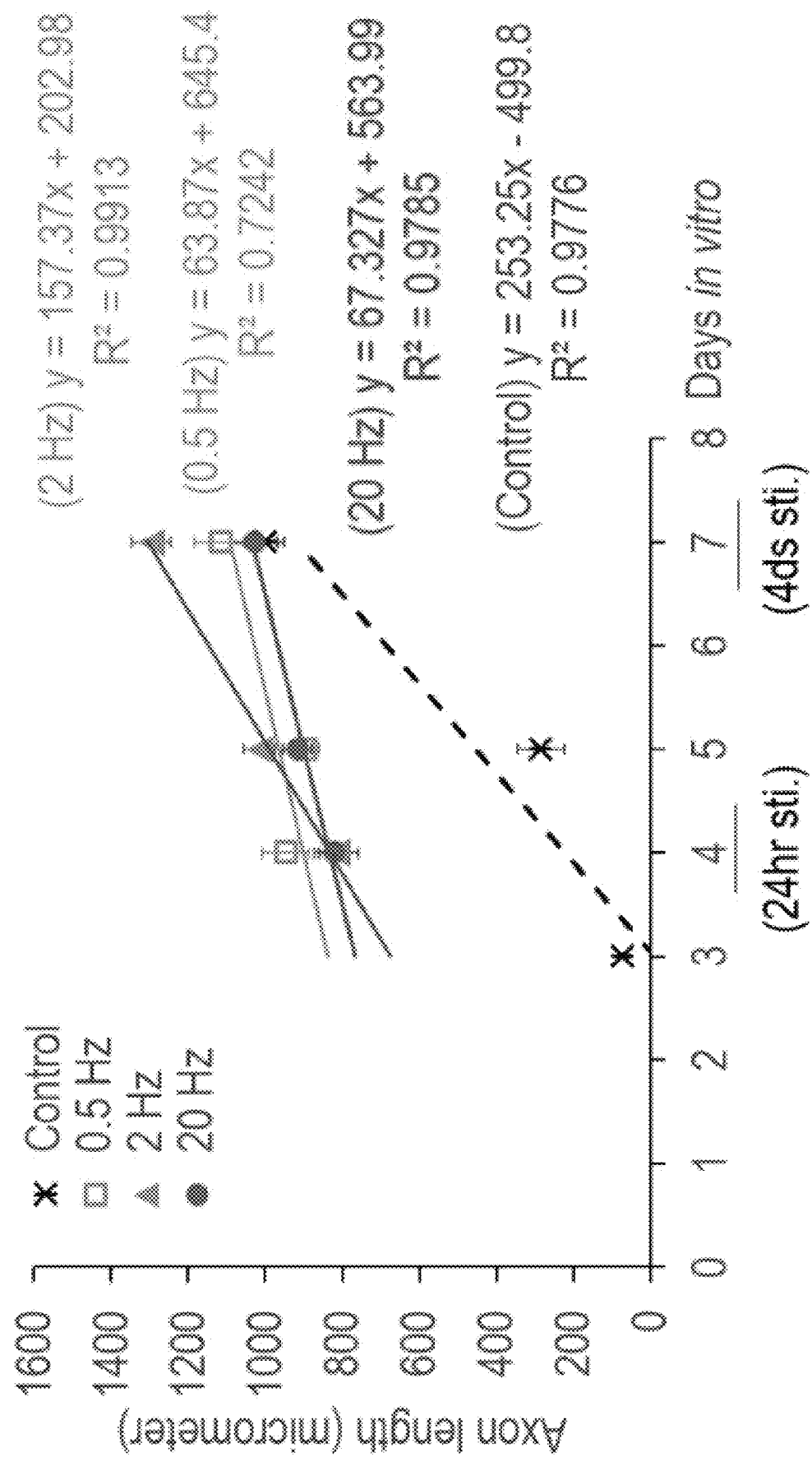
Figure 11N:
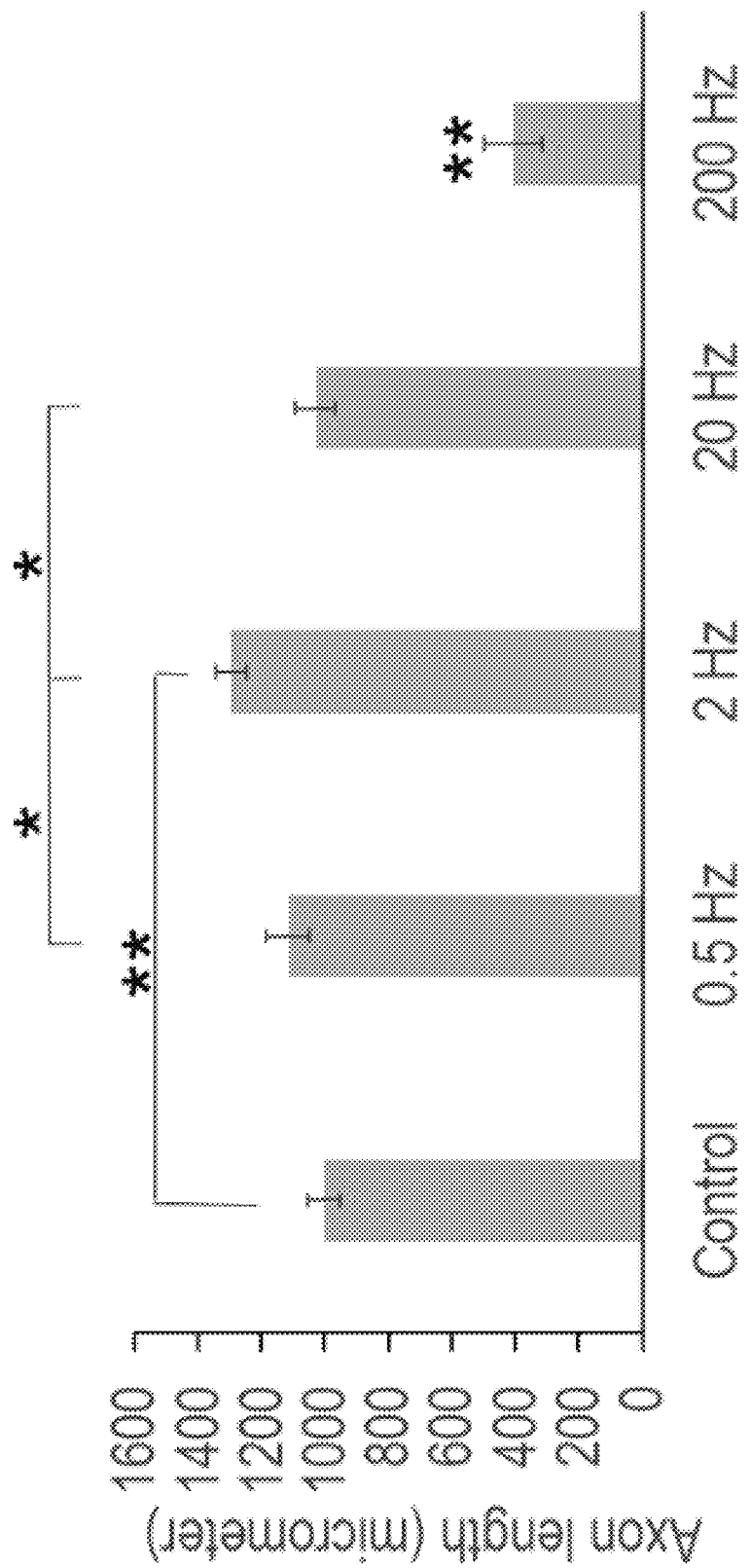

Axon growth of 3D cultures was examined under electrical stimulation of 0.5-200 Hz up to 4 days (i.e., DIV 7) (FIGS. 11A-N). FIGS. 11A-I show representative 2D projections of β III-tubulin stained axons in the center core region of 3D cultures. Among all the frequencies tested, 200 Hz showed axon length decrease from 693.8±59.1 μm (n=9) after 48 hours to 405.4±90.5 μm (n=4) after 4 days of stimulation, indicating inhibition of axon length growth. Cultures stimulated at 0.5, 2 and 20 Hz showed linear relationships between days in vitro and axon length increases (FIG. 11M). 2 Hz showed stronger effect on axon length growth compared to 0.5 Hz and 20 Hz.

Though the grow curve slopes of stimulated cultures appeared to be smaller than control cultures, axon lengths were longer compared to the control at corresponding time points. For example, there was significant length increases under electrical stimulation after 48 hr, e.g., DIV 5, compared to the control; this finding suggested an immediate boost of axon length growth by electrical stimulation.

After 4 days electrical stimulation (FIG. 11N), axon length was the longest at 2 Hz of 1296.1±49.8 μm (n=40), significantly longer than unstimulated control cultures of 1000.2±50.6 μm (n=21; **, p<0.01) and cultures at 0.5 Hz of 1115.2±68.2 (n=18; *, p<0.05) or at 20 Hz of 1029.5±62.5 μm (n=18; **, p<0.01). Axon length of 200 Hz stimulated cultures was the shortest with significant differences than other conditions.

6.19 Axon 3D Orientation after Electrical Stimulation

Disclosed is a 3D environment that confer a higher degree of freedom of neurite movement, therefore providing more direct effects of electric fields on axon orientation. FIGS. 12A-C outline the schematics of hypothesized axon orientation under electrical fields. Based on DC field-induced cathode-orienting neurite outgrowth (FIG. 4A), a neuron would sense an adjacent electrode under AC field as an on-off cathode (with the rate depending on AC field frequency), therefore grow towards it perpendicularly (FIG. 12B). Between paired electrodes, as in the case of the center region of the 3D brain tissue model, once the neurite has traversed away from its originating electrode for half a distance of an EF, it would seek the other closer electrode as the cathode; the outcome would be axon tracts in parallel to the EF direction (FIG. 12C)

Figure 12G:
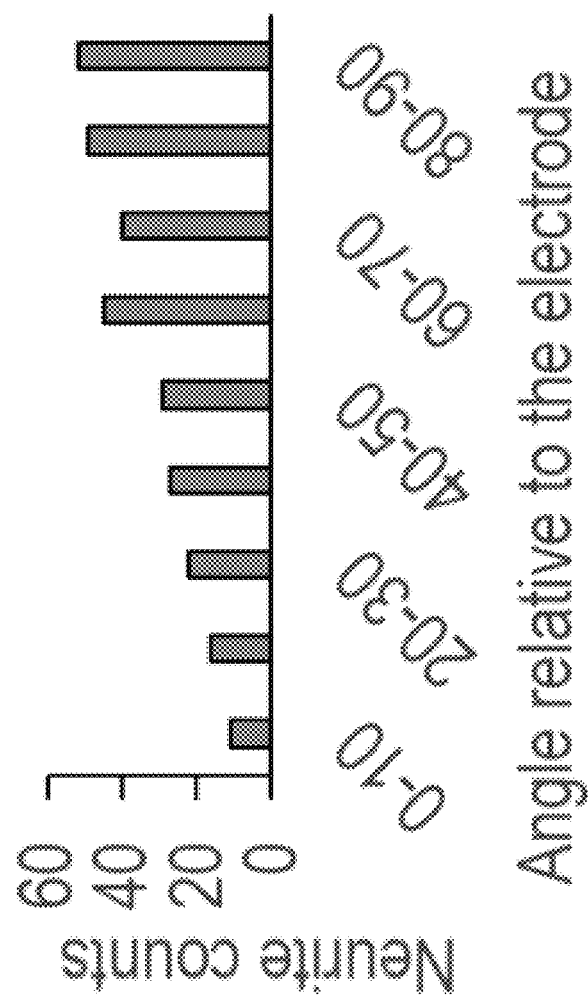
Figures 12H, 12I, 12J:
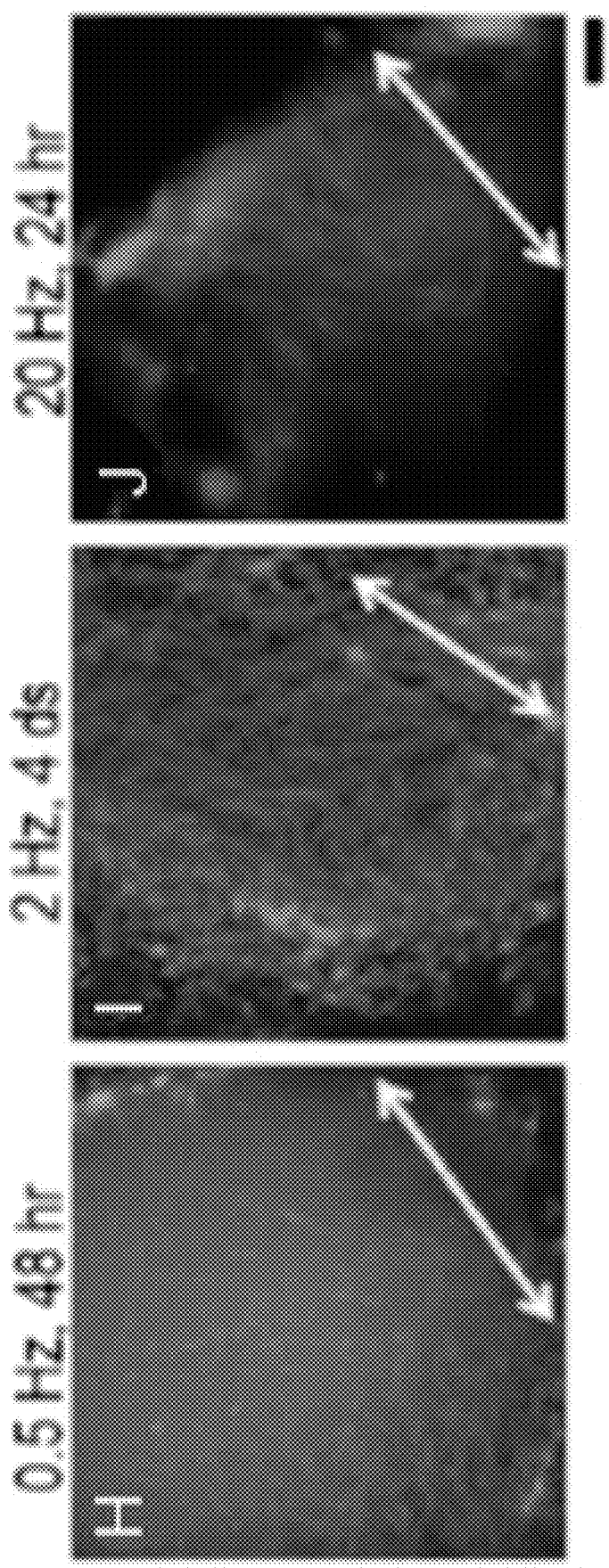

3D axon growth showed evidence of AC-induced orientation (FIGS. 12D-K). As previously noted (FIGS. 10A-D), neurons adjacent to electrodes grew their extensions in perpendicular to the electrode, under all AC field frequencies tested (FIG. 12D-G). Measurement of the angles of neurites trespassing an electrode showed that ~74% (215/291) neurites oriented between 45 to 90 degrees of the electrode (FIG. 12G).

Figure 12K:
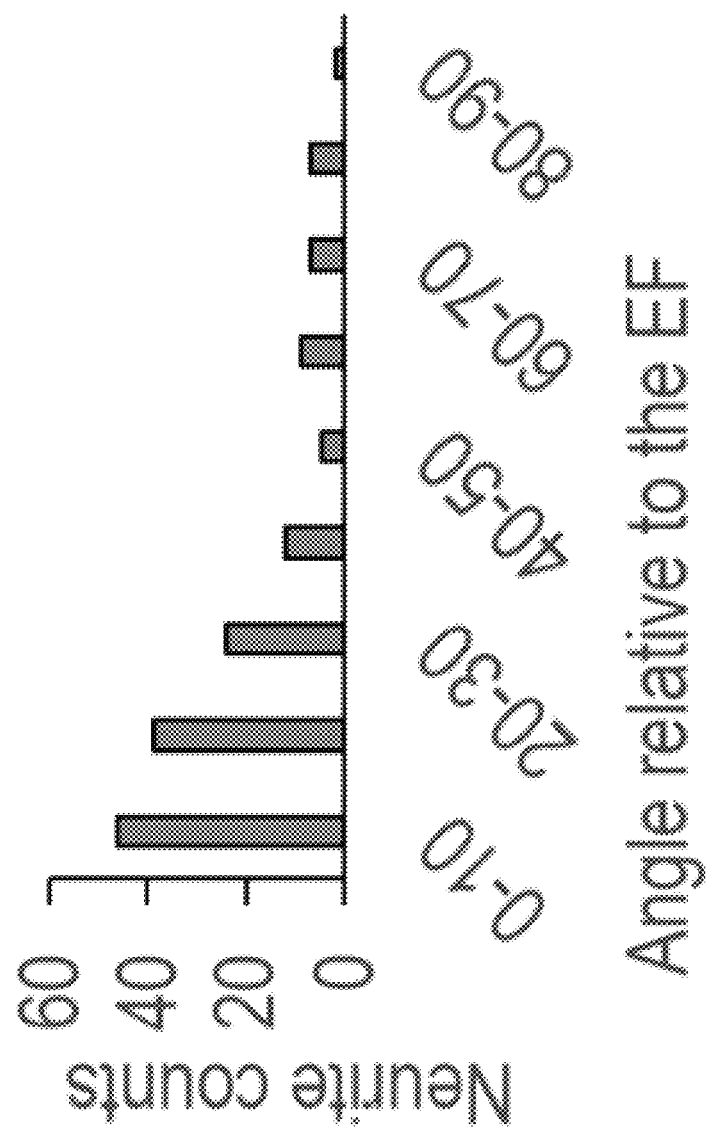

In the center core of 3D cultures, axons showed parallel alignment to the EF field, under all AC frequencies tested (FIGS. 12H-K; EF field direction marked in arrows). Measurement of the angles of neurites in the 3D center core showed that ~72% (109/151) neurites oriented between 0 to 30 degrees of the EF direction (FIG. 12K).

6.20 Axon 3D Growth after Local Delivery of Soluble Factors

Figures 13G, 13H, 13I, 13J:
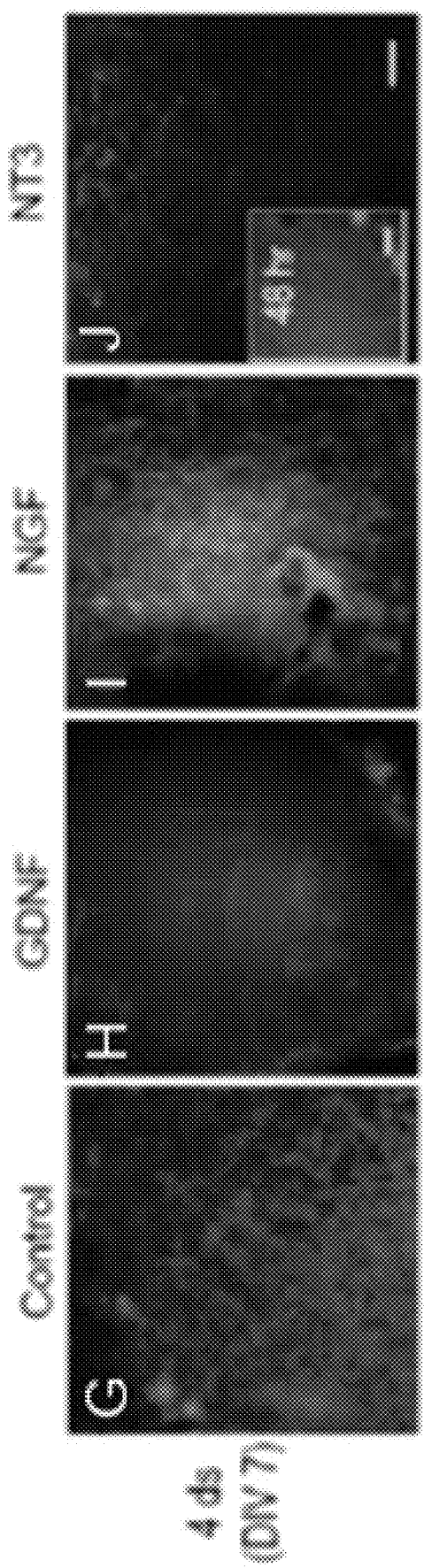

Axon growth in the 3D brain tissue model was compared after local delivery of soluble factors, including extracellular matrix components such as laminin (LN) and fibronectin (FN) and brain-derived neurotrophic factor (BDNF), glial-derived neurotrophic factor (GDNF), neurotrophin-3 (NT3), and nerve growth factor (NGF) (FIGS. 13A-M). FIGS. 13A-J show representative 2D projections of β III-tubulin stained axons in the center core of 3D cultures. Compared to neurotrophic factors, ECM components such as LN and FN produced more abundant axons (FIGS. 13A-F). Among the neurotrophic factors, BDNF produced most abundant axons, followed by NGF and BDNF. NT3 showed mixed results with signs of axon degeneration after 4 days (FIG. 13J) compared to robust growth after 48 hr exposure (FIG. 13J, inset).

Figure 13K:
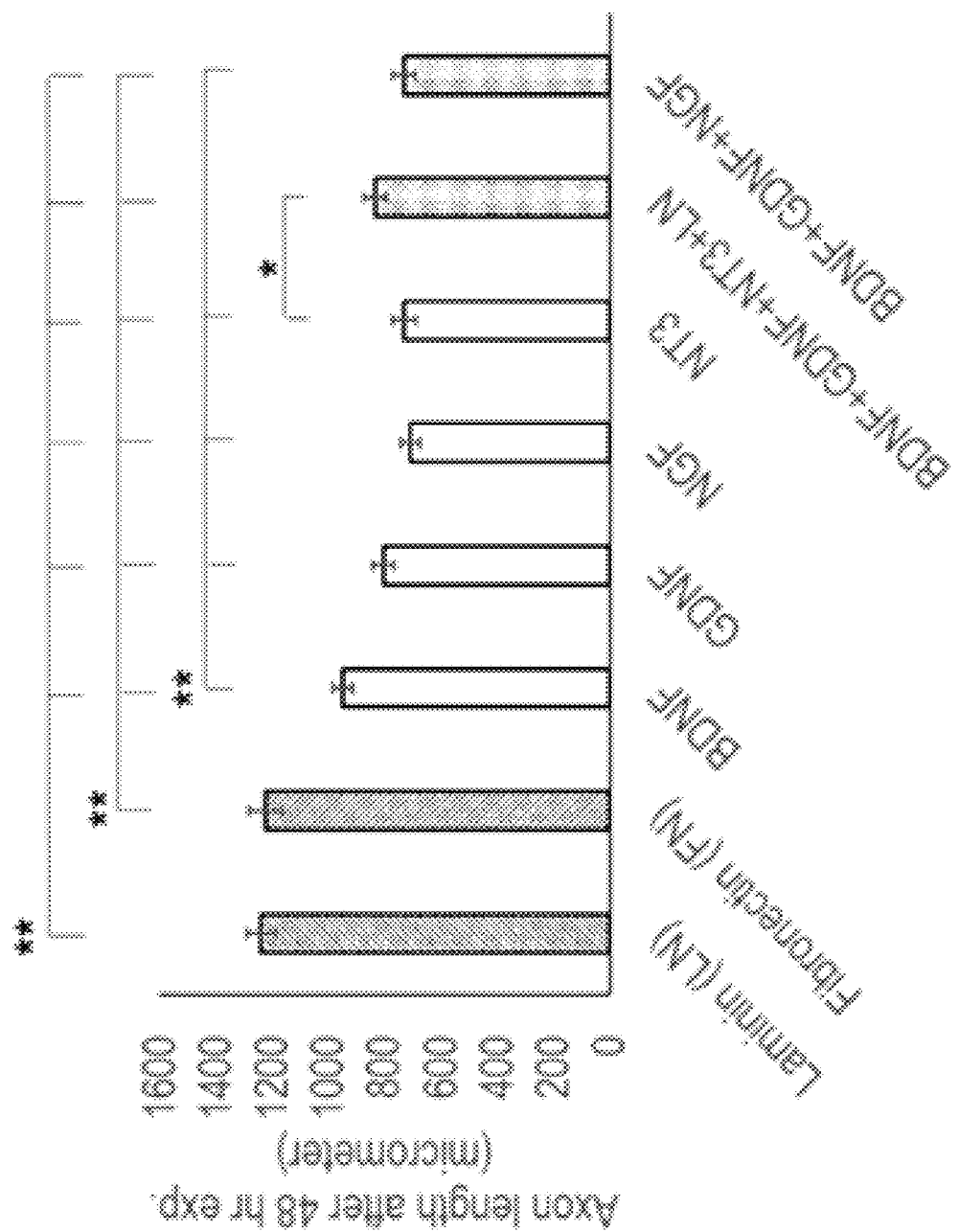
Figure 13L:
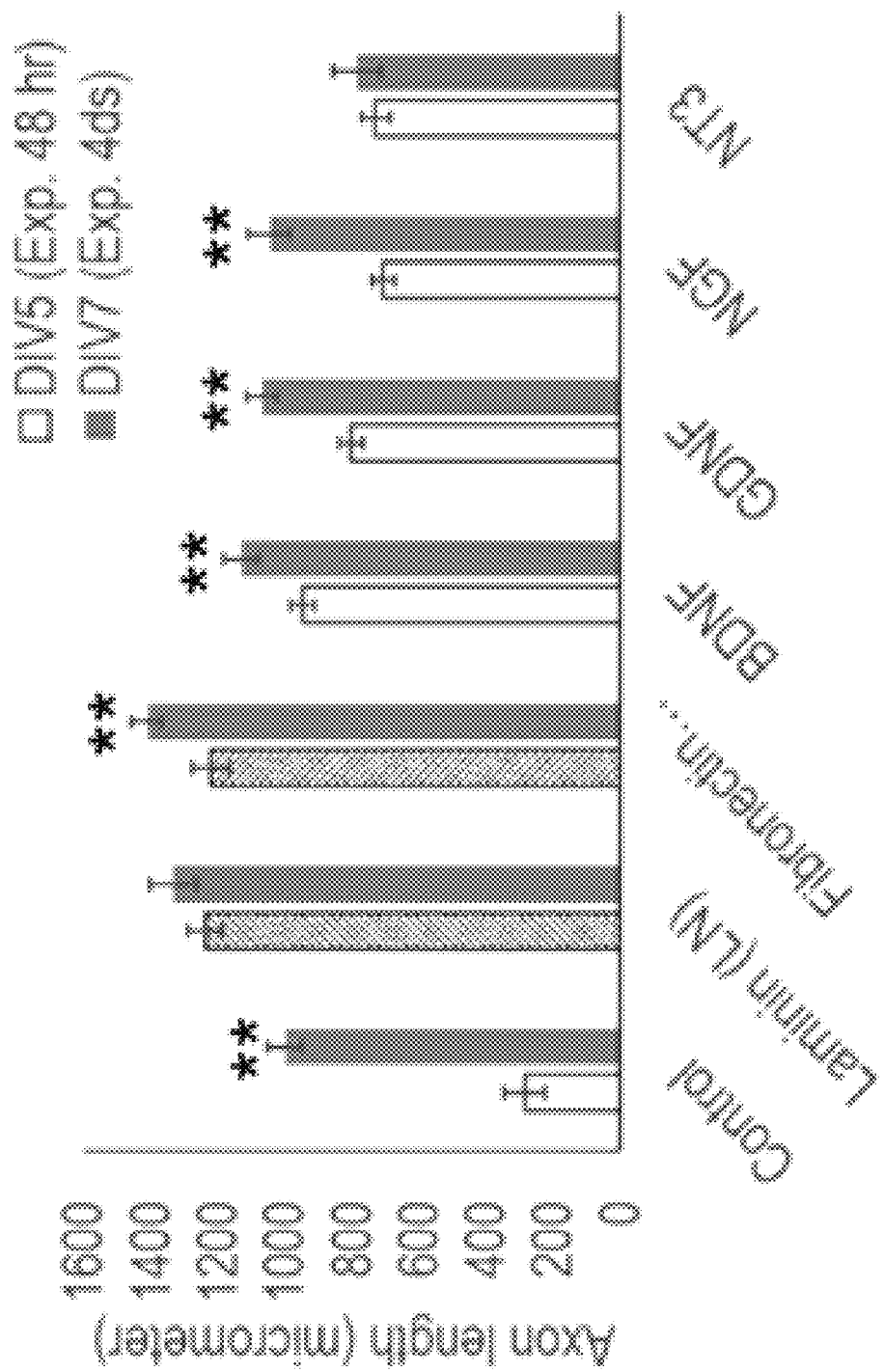
Figure 13M:
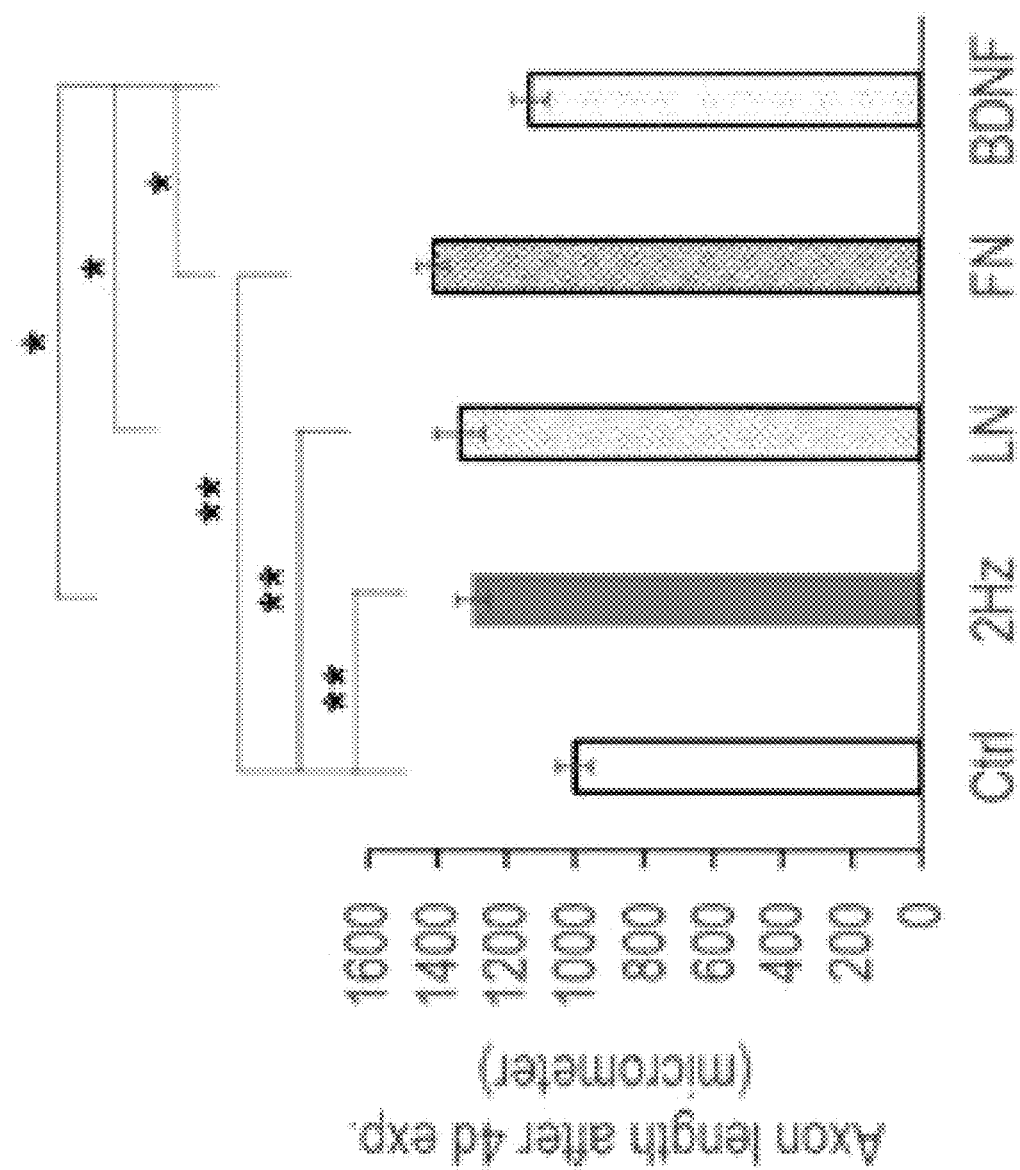

Axon lengths under LN and FN exposure for 48 hr were 1237.7±51.3 (n=37) and 1220.7±57.5 (n=22), respectively, significantly longer than all the neurotrophic factors tested (FIG. 13K). Among the neurotrophic factors, BDNF showed the longest length growth of 946.8±35.2 µm (n=90), with significant differences than GDNF of 802.5±38.0 µm (n=43), NT3 of 728.2±42.5 µm (n=58) µm, NGF of 706.5±33.4 µm (n=44). Combinations of soluble factors failed to show synergistic length growth promotion; with lengths of 831.3±40.4 µm (n=39) and 731.2±38.9 µm (n=39) under BDNF, GDNF, NT3, LN combinations and BDNF, GDNF, NGF combinations, respectively.

Axon length showed significant increases from 48 hr to 4 ds exposure (FIG. 13L), under all soluble factors tested except LN and NT3. Axon lengths after 4 ds exposure of LN, FN, BDNF, GDNF, NT3 and NGF were 1332.5±71.0 (n=28) and 1411.8±45.1 (n=14), 1131.1±52.0 (n=43), 1068.3±43.9 (n=49), 784.3±71.6 (n=4) and 1045.6±61.9 (n=21), respectively. The biggest length increases by LN and FN compared to the control indicated that ECM components played more significant roles in the early days (<DIV 5) of neurite growth. In comparison, the neurotrophic factors (BDNF, GDNF, NGF) may promote the later stage, i.e., day 5 to 7, of neurite growth. The differences between LN or FN with all the neurotropic factors (BDNF, GDNF, NT3 and NGF) were significant; and there was no significant difference among these neurotropic factors other than NT3.

The above results show that conditions that produced significant axon length growth were 2 Hz field stimulation and exposure to LN, FN and BDNF. Comparisons of axon lengths at DIV 7 under these conditions (FIG. 13M) revealed that 2 Hz stimulation and LN or FN local delivery produced axons of ~30%, 33% and 41% longer, respectively, compared to the control; and ~15%, 18% and 25% longer, respectively, compared to BDNF (*, p<0.05; **, p<0.01). BDNF produced axons of ~13% longer than the control, with no statistical difference (p=0.31).

The axon lengths under 2 Hz stimulation and LN or FN exposure were found to be statistically similar (p=0.68 vs LN; p=0.09 vs. FN).

6.21 Neural-Electric Interface

Gold wires were embedded in a bioengineered 3D brain tissue-like model. The wires were supported by the silk protein material-based scaffold and embedded within the infused collagen gel. Based on the strong effect of electric field on neurite alignment, it is important to place the electrode in the 3D culture system in ways that neurite orientation could be observed in relation to the electrode. In our model, the wires were positioned at the interface of the cell body-containing scaffold region and the axon-containing gel region, spanning the neurite outgrowth area. This setup ensures direct effect of applied electrical field on axon growth, not neuronal cell bodies. In addition, the horizontal and vertical placements of the wire pair allowed imaging of axon extensions in-between and in the vicinity of the electrodes, respectively.

6.22 Electrical Stimulation to Promote Neuronal Growth

Biphasic square waves of 0.5 Hz to 2 kHz were used to promote neuronal growth, it is found that 2 Hz produced most pronounced effect on axon length growth with 30% increase than unstimulated control cultures. In contrast, 200 Hz and 2 kHz inhibited axon growth after 24 hr stimulation. Both 0.5 Hz and 20 Hz showed initial axon length increase at 24 hr but no difference after 4 days compared to control. It is possible that 2 Hz is the optimal AC frequency to elicit neuronal response, while maintaining an effective field potential by allowing sufficient dissipation of the capacitance built-up at the electrode/fluid interface in the 3D culture system.

Characterization of field potential distribution in the 3D culture system will be needed to further elucidate the mechanism. Nevertheless, this study provides a first report of AC stimulation-enhanced axon 3D growth. It is important to note that the AC frequency we used here is different than frequencies for pulsed field stimulation. Our system essentially is continuous field stimulation only with field polarity alternating at the set frequency; and the AC field strength remains constant. Pulse field has a delay after a short (microseconds to milliseconds) pulse stimulation; and the applied field strength is proportional to the frequency of pulses. Accordingly, studies of 20 Hz being effective in neuronal regenerative growth cannot be compared with the 20 Hz AC field used in this study. Axotomized and repaired rodent nerve hind-limb models, 1 h to 2 weeks of continuous electrical stimulation (20 Hz, 100 µs, 0.5-5 V) resulted in accelerated axonal regeneration (230-233) The frequency of 20 Hz was chosen because it is the physiologically relevant frequency of motoneuron discharge, and the chosen intensity level was high enough to induce firing (231).

In terms of field strength, the physiologically significant range of endogenous gradients of electrical fields of vertebrates is on the order of 10 mV-1V/mm (Borgens and others). Studies of 2D neuronal cultures suggest a range of 10-500 mV/mm to produce growth cone turning response. The growth rate of *Xenopus* neurite was increased twofold to threefold in fibers turned toward the cathode, depending on the magnitude of the imposed fields with the most marked responses occurring between 70 and 140 mV/mm (12, 14, 16-19, 22, 28). In our study, we chose conditions that was previously shown in 2D culture of rat cortical neurons to evoke immediate calcium responses without cellular damage, i.e, ~100 mV/mm of 2 Hz-2 kHz biphasic square wave (Tang-Schomer et al., 2014a). The setup in this study generated a theoretical electric field strength of 80 or 160 mV/mm (e.g, at 160 mV peak-to-peak or 320 mV across ~2 mm distance, respectively). We found that 160 mV/mm did significant harm to neurons after 24 hr continuous stimulation at all frequencies tested, though neurons appeared to be intact and functional with short-term stimulation (in hours) under same conditions. Studies of electrically stimulated *Xenopus* axon turning show that the extent of neurite alignment under a uniform DC field was similar to pulsed fields with different frequencies but equivalent time-averaged field (Poo's study). These results indicate that neuronal response to applied electrical field depends on cumulative field effect, lower field strength for longer time or higher strength with less time. In certain embodiments, the field intensity is 200-300 μV/mm, 300-400 μV/mm, 400-500 μV/mm. In certain embodiments, the duration is 1-2 weeks, 2-3 weeks, 3-4 weeks, 4-6 weeks, 6-8 weeks, 8-10 weeks, 10-12 weeks, 12-15 weeks. In one embodiment, the field intensity and duration is 200 μV/mm for up to 4 weeks. In one embodiment, the oscillating electric fields is 500-600 μV/mm for 18 days. In one embodiment the oscillating electric fields is 500-600 μV/mm, 15-min on/15-min off, for up to 15 weeks. In comparison, the 2 Hz AC field stimulation (80 mV/mm for 4 days) found effective in the 3D neuronal culture system could be further optimized for prolonged 3D tissue growth.

6.23 Differential Effects of Neurotrofic Factors on Tissue-Scale 3D Axon Growth The disclosure herein demonstrates that the innate electrical activity of neurons as well as extrinsic electrical activity significantly modulates the growth of neurons. Levels of brain-derived neurotrophic factor (BDNF), a soluble factor promoting neuronal outgrowth and survival, are greater for animals receiving electrical stimulation as compared with unstimulated controls.

6.24 Implications for Neural Tissue Engineering

Electric field exist in periods when active neurogenesis is occurring, involving neuronal division, neuronal migration, and axonal guidance. This offers substantial scope for an applied EF to act as a robust guidance cue to direct axonal growth in a spatially and temporally controlled manner. The present disclosure may be used to recreate axon aligned tracts in vitro with a fine spatial and temporal resolution, and therefore it provides an easy-to-use testbed for reproducing aligned axon tract formation in large neural populations as well as studying the effects of exogenous inputs (e.g., chemical compounds or novel neuromodulation approaches) on 3D neuronal growth. The present disclosure provides basis for further optimizing stimulation parameters, in conjunction of delivery of growth promoting soluble factors in a brain mimetic 3D environment.

6.25 Materials and Methods

6.25.1 Silk Film Supported Neural-Electric Interface

Silk films were processed as previously reported (Tang-Schomer et al., 2014c). Briefly, silk fibroin (1-2%) solution extracted from *Bombyx mori* silkworm cocoons (Tajima Shoji Co., Yokohama, Japan) was prepared. A pair of gold wires (100 μm dia., SPM Inc., Armonk, N.Y., USA) were positioned at 6 mm apart onto a PDMS mold (16 mm dia.), and immersed in silk solution. After drying in air, the silk film (~5 μm thickness) was peeled off the mold with the gold wires embedded in the film. Films were rendered water-insoluble by β-sheet formation via water annealing in a water-filled desiccator for >5 h. To prepare for cell culture, the film was UV sterilized, coated with 20 μg/ml poly-L-lysine (Sigma-Aldrich, St. Louis, Mo., USA) overnight, washed and dried prior to introducing cells.

6.25.2 Primary Cortical Neuronal Culture

The rat brain tissue dissociation protocol was approved by Tufts University Institutional Animal Care and Use Committee and complies with the NIH Guide for the Care and Use of Laboratory Animals (IACUC #B2011-45). Cortices from embryonic day 18 (E18) Sprague Dawley rats (Charles River, Wilmington, Mass., USA) were isolated, dissociated with trypsin (0.3%, Sigma) and DNase (0.2%, Roche Applied Science, Indianapolis, Ind., USA) followed with trypsin inhibition with soybean proteins (1 mg/mL, Sigma), centrifuged, and plated at 200,000-625,000 cells/cm$^2$ in NeuroBasal media (Invitrogen, Carlsbad, Calif., USA) supplemented with B-27 neural supplement, penicillin/streptomycin (100 U/mL and 100 μg/mL), and GlutaMax (2 mM) (Invitrogen). Cultures were maintained in 37° C., 100% humidity and 5% $CO_2$ in an incubator (Forma Scientific, Marietta, Ohio, USA) for up to 16 days in vitro (DIV 1-16). Cultures of DIV 14-16 were used for stimulation.

6.25.3 Electrical Stimulation

For the synchronization experiments, the interface cultures were set up with extensions of the silk protein film-embedded gold wires connected to an electrical stimulator, as previously described (Tang-Schomer et al., 2014c). The field potential was set at 160 mV between the electrodes, and validated with an oscilloscope. A functional generator (Tenma Universal Test Center 72-5085, MCM Electronics, Centerville Ohio, USA) delivered biphasic, rectangular waves with frequencies ranging from 0.2 Hz-200 kHz. Monophasic pulses (0.1 millisecond) were delivered by a Grass S44 stimulator and SIUS stimulation isolation unit at frequencies ranging from 0.2 Hz-2 kHz. A total of twelve cultures from six independent batches of cells (i.e., rats) were used. Voltage applied across each silk film was verified prior to stimulation with an oscilloscope. No cellular damage was observed during all our experiments, based on morphological characterization.

For directed growth stimulation of axonal growth experiment, all the interface cultures were set up with the two electrodes spaced 6 mm apart with extensions connected to electrical stimulators, as previously described (Tang-Schomer et al., 2014c). Electrical fields of biphasic waves were delivered to the 3D tissue culture, inside an incubator, via the gold wires connecting to a functional generator outside the incubator. Waves of different frequencies (peak-to-peak 160 mV, 0.5 Hz-2 kHz) were applied starting at the $3^{rd}$ day of in vitro culture (DIV 3). A functional generator (Tenma Universal Test Center 72-5085, MCM Electronics, Centerville Ohio, USA) delivered biphasic, rectangular waves with frequencies ranging from 0.5 Hz-2 kHz. Voltage applied across each silk film was verified prior to stimulation.

6.25.4 Statistical Analysis

All data presented are expressed as mean±standard error of mean. Statistical analysis was carried out suing single-factor analysis of variance. A value of p≤0.05 was considered statistically significant.

6.25.5 Calcium Imaging and Image Analysis

Calcium dye Fluo-4 AM (Invitrogen) was used to visualize changes in intracellular calcium concentration. Experiments were performed in controlled saline solution (CSS: 120 mM NaCl, 5.4 mM KCl, 0.8 mM $MgCl_2$, 1.8 mM $CaCl_2$), 15 mM glucose, and 25 mM HEPES, pH 7.4). Cultures were loaded with 1 μg/ml dye solution (in PBS containing 0.2% DMSO) at 37° C. for 30 min, washed with PBS, and incubated in fresh media for another 30° min. The cultures were mounted onto a confocal microscope (Leica TCS SP2, Leica Microsystems, Wetzlar, Germany) within an environmental chamber with the temperature maintained at 37° C.

During stimulation, time-lapse fluorescence images were acquired with the same optical settings (at Ex/Em of 488/525 nm). For field stimulation, we imaged a 30-section z-stack every minute for 45-60 minutes. Time-series fluorescence images of one focal plane at the middle-point of a z-stack were used for image analysis. For pulse stimulation, images at a fixed focal plane were acquired every 10 seconds (i.e., $\Delta t=10$ s) for 20-30 minutes.

NIH Image J software suite was used to quantify the fluorescence intensity. Circular selection was made for each cell body, and the mean fluorescence intensity was measured. A neuron's fluorescence intensity at a specific time point t ($F_t$) divided by the intensity at time 0 ($F_0$, no stimulation) of the same neuron gave the calcium signal change and reported as $F_t/F_0$.

6.25.6 Network Analysis and Unsupervised Community Detection

For the analysis of the functional connectivity between neurons, a.k.a. network analysis (Newman, 2010), sample distribution of the fluorescence intensities at time 0 ($F_0$) was estimated and the values of mean ($\mu_0$) and standard deviation ($\sigma_0$) were computed. Each fluorescence intensity time series $F_t$ was normalized by subtracting $\mu_0$ and dividing by $\sigma_0$. This normalization procedure aimed at preserving the range of fluorescence intensities observed across each cortical culture while removing time-series-specific biases. The normalized fluorescence intensity time series were then used to run the network partition algorithm described in Results and to identify functional clusters.

6.25.7 Silk Protein-Based Scaffolds and Extracellular Matrix (ECM) Gel Preparation Silk solution and porous scaffolds were prepared from *Bombyx mori* cocoons as described previously (Tang-Schomer et al., 2014). Salt-leached porous silk mats of 100 mm dia. were provided by David Kaplan's laboratory at Tufts University. A biopsy punch was used to generate donut-shaped silk protein-based scaffold (outer diameter, 5 mm; inner diameter, 2 mm; height, 2 mm). Silk scaffolds were autoclaved, coated with poly-L-lysine (10 μg/mL, Sigma) overnight, and washed 3 times with phosphate buffered saline (PBS, Sigma).

Collagen gel was prepared from high-concentration rat tail type I collagen (8-10 mg/ml, Fisher Scientific), 10×M199 medium (Thermo Fisher) and 1 M sodium hydroxide mixed at a ratio of 88:10:2, followed by gelling at 37° C. for 1-2 hrs.

To make a scaffold-gel composite structure, the scaffolds were washed with ECM gels in the liquid form to replace the medium within the scaffold, followed by incubation at 37° C. for 1-2 hours before culture medium immersion. To make tissue spheroid-gel structure, approximately 50 μL matrix gel solution was used to embed the spheroids in U-shaped wells of a 96-well plate.

6.25.8 Cell Plating

For 2D cultures, cells were plated at 105,263 cells/$cm^2$ in 6-well plate (corresponding to 1 million cells/well). One plate per time-point was used, totaling 14 plates. For 3D scaffold-based cultures, the scaffolds were immersed in high-density cell suspensions (~100 million cells/mL) for 24 hours followed by extensive washes with media, and proceed to scaffold-only cultures or ECM gel-infused composite cultures. For scaffold-free cultures, cell dissociates were distributed at ~40,000 cells/well to U-shaped wells of a 96-well plate. At 3 days in vitro (DIV 3), some 3D cultures and tissue spheroids in suspension cultures were embedded in ECM matrix.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description is offered by way of illustration only and not as a limitation.

REFERENCES

Ali, M. M., Sellers, K. K., and Frohlich, F. (2013). Transcranial alternating current stimulation modulates large-scale cortical network activity by network resonance. *J. Neurosci.* 33, 11262-11275. doi: 10.1523/JNEUROSCI.5867-12.2013

Bagley, E. E., and Westbrook, G. L. (2012). Short-term field stimulation mimics synaptic maturation of hippocampal synapses. *J. Physiol.* 590, 1641-1654. doi: 10.1113/jphysiol.2011.224964

Bakkum, D. J., Chao, Z. C., and Potter, S. M. (2008a). Long-term activity-dependent plasticity of action potential propagation delay and amplitude in cortical networks. *PLoS one* 3:e2088. doi: 10.1371/journal.pone.0002088

Bakkum, D. J., Chao, Z. C., and Potter, S. M. (2008b). Spatio-temporal electrical stimuli shape behavior of an embodied cortical network in a goal-directed learning task. *J. Neural Eng.* 5, 310-323. doi: 10.1088/1741-2560/5/3/004

Bassett, D. S., and Bullmore, E. (2006). Small-world brain networks. *Neuroscientist* 12, 512-523. doi: 10.1177/1073858406293182

Bassett, D. S., Porter, M. A., Wymbs, N. F., Grafton, S. T., Carlson, J. M., and Mucha, P. J. (2013). Robust detection of dynamic community structure in networks. *Chaos* 23:013142. doi: 10.1063/1.4790830

Berridge, M. J., Lipp, P., and Bootman, M. D. (2000). The versatility and universality of calcium signalling. *Nat. Rev. Mol. Cell Biol.* 1, 11-21. doi: 10.1038/35036035

Bestmann, S., De Berker, A. O., and Bonaiuto, J. (2015). Understanding the behavioural consequences of noninvasive brain stimulation. *Trends Cogn. Sci.* 19, 13-20. doi: 10.1016/j.tics.2014.10.003

Bikson, M., Inoue, M., Akiyama, H., Deans, J. K., Fox, J. E., Miyakawa, H., et al. (2004). Effects of uniform extracellular DC electric fields on excitability in rat hippocampal slices in vitro. *J. Physiol.* 557, 175-190. doi: 10.1113/jphysiol.2003.055772

Billeh, Y. N., Schaub, M. T., Anastassiou, C. A., Barahona, M., and Koch, C. (2014). Revealing cell assemblies at multiple levels of granularity. *J. Neurosci. Methods* 236, 92-106. doi: 10.1016/j.jneumeth.2014.08.011

Birdno, M. J., and Grill, W. M. (2008). Mechanisms of deep brain stimulation in movement disorders as revealed by changes in stimulus frequency. *Neurotherapeutics* 5, 14-25. doi: 10.1016/j.nurt.2007.10.067

Bito, H., Deisseroth, K., and Tsien, R. W. (1996). CREB phosphorylation and dephosphorylation: a Ca(2+)- and stimulus duration-dependent switch for hippocampal gene expression. *Cell* 87, 1203-1214. doi: 10.1016/S0092-8674(00)81816-4

Blondel, V. D., Guillaume, J. L., Lambiotte, R., and Lefebvre, E. (2008). Fast unfolding of communities in large networks. *J. Statist. Mech.* 2008:10008. doi: 10.1088/1742-5468/2008/10/P10008

Broggini, A. C. S., Esteves, I. M., Romcy-Pereira, R. N., Leite, J. P., and Leao, R. N. (2016). Pre-ictal increase in theta synchrony between the hippocampus and prefrontal cortex in a rat model of temporal lobe epilepsy. *Exp. Neurol.* 279, 232-242. doi: 10.1016/j.expneurol.2016.03.007

Brummer, S. B., and Turner, M. J. (1977). Electrochemical considerations for safe electrical stimulation of the nervous system with platinum electrodes. *IEEE Trans. Biomed. Eng.* 24, 59-63. doi: 10.1109/TBME.1977.326218

Burnett, P., Robertson, J. K., Palmer, J. M., Ryan, R. R., Dubin, A. E., and Zivin, R. A. (2003). Fluorescence imaging of electrically stimulated cells. *J. Biomol. Screen.* 8, 660-667. doi: 10.1177/1087057103258546

Burns, S. P., Santaniello, S., Yaffe, R. B., Jouny, C. C., Crone, N. E., Bergey, G. K., et al. (2014). Network dynamics of the brain and influence of the epileptic seizure onset zone. *Proc. Natl. Acad. Sci. U.S.A.* 111, E5321-E5330. doi: 10.1073/pnas.1401752111

Buzsaki, G., and Draguhn, A. (2004). Neuronal oscillations in cortical networks. *Science* 304, 1926-1929. doi: 10.1126/science.1099745

Buzsaiki, G. (2006). *Rhythms of the Brain*. New York, N.Y.: Oxford University Press. doi: 10.1093/acprof:oso/9780195301069.001.0001

Cao, B., Wang, J., Mu, L., Poon, D. C., and Li, Y. (2016). Impairment of decision making associated with disruption of phase-locking in the anterior cingulate cortex in viscerally hypersensitive rats. *Exp. Neurol.* 286, 21-31. doi: 10.1016/j.expneurol.2016.09.010

Chao, Z. C., Bakkum, D. J., and Potter, S. M. (2007). Region-specific network plasticity in simulated and living cortical networks: comparison of the center of activity trajectory (CAT) with other statistics. *J. Neural Eng.* 4, 294-308. doi: 10.1088/1741-2560/4/3/015

Chao, Z. C., Bakkum, D. J., Wagenaar, D. A., and Potter, S. M. (2005). Effects of random external background stimulation on network synaptic stability after tetanization: a modeling study. *Neuroinformatics* 3, 263-280. doi: 10.1385/NI:3:3:263

Chwalek, K., Sood, D., Cantley, W. L., White, J. D., Tang-Schomer, M., and Kaplan, D. L. (2015a). Engineered 3D silk-collagen-based model of polarized neural tissue. *J. Vs. Exp.* 104:e52970. doi: 10.3791/52970

Chwalek, K., Tang-Schomer, M. D., Omenetto, F. G., and Kaplan, D. L. (2015b). In vitro bioengineered model of cortical brain tissue. *Nat. Protoc.* 10, 1362-1373. doi: 10.1038/nprot.2015.091

Darbon, P., Scicluna, L., Tscherter, A., and Streit, J. (2002). Mechanisms controlling bursting activity induced by disinhibition in spinal cord networks. *Eur. J. Neurosci.* 15, 671-683. doi: 10.1046/j.1460-9568.2002.01904.x Domachuk, P., Perry, H., Amsden, J. J., Kaplan, D. L., and Omenetto, F. G. (2009). Bioactive "self-sensing" optical systems. *Appl. Phys. Lett.* 95:253702. doi: 10.1063/1.3275719

Eytan, D., Brenner, N., and Marom, S. (2003). Selective adaptation in networks of cortical neurons. *J. Neurosci.* 23, 9349-9356. doi: 10.1523/JNEUROSCI.23-28-09349.2003

Ferrucci, R., Mameli, F., Guidi, I., Mrakic-Sposta, S., Vergari, M., Marceglia, S., et al. (2008). Transcranial direct current stimulation improves recognition memory in Alzheimer disease. *Neurology* 71, 493-498. doi: 10.1212/01.wnl.0000317060.43722.a3

Frohlich, F. (2014). Endogenous and exogenous electric fields as modifiers of brain activity: rational design of noninvasive brain stimulation with transcranial alternating current stimulation. *Dialogues Clin. Neurosci.* 16, 93-102.

Frohlich, F. (2015). Experiments and models of cortical oscillations as a target for noninvasive brain stimulation. *Prog. Brain Res.* 222, 41-73. doi: 10.1016/bs.pbr.2015.07.025

Goold, C. P., and Nicoll, R. A. (2010). Single-cell optogenetic excitation drives homeostatic synaptic depression. *Neuron* 68, 512-528. doi: 10.1016/j.neuron.2010.09.020

Graves, M. S., Hassell, T., Beier, B. L., Albors, G. O., and Irazoqui, P. P. (2011). Electrically mediated neuronal guidance with applied alternating current electric fields. *Ann. Biomed. Eng.* 39, 1759-1767. doi: 10.1007/s10439-011-0259-8

Gross, R. E., and Lozano, A. M. (2000). Advances in neurostimulation for movement disorders. *Neurol. Res.* 22, 247-258. doi: 10.1080/01616412.2000.11740667

Holtmaat, A., and Svoboda, K. (2009). Experience-dependent structural synaptic plasticity in the mammalian brain. *Nat. Rev. Neurosci.* 10, 647-658. doi: 10.1038/nrn2699

Hronik-Tupaj, M., Raja, W. K., Tang-Schomer, M., Omenetto, F. G., and Kaplan, D. L. (2013). Neural responses to electrical stimulation on patterned silk films. *J. Biomed. Mater. Res. A* 101, 2559-2572. doi: 10.1002/jbm.a.34565

Hummel, F., Celnik, P., Giraux, P., Floel, A., Wu, W. H., Gerloff, C., et al. (2005). Effects of non-invasive cortical stimulation on skilled motor function in chronic stroke. *Brain* 128, 490-499. doi: 10.1093/brain/awh369

Hutt, A., Griffiths, J. D., Herrmann, C. S., and Lefebvre, J. (2018). Effect of Stimulation waveform on the non-linear entrainment of cortical alpha oscillations. *Front. Neurosci.* 12:376. doi: 10.3389/fnins.2018.00376

Jayakar, P., Alvarez, L. A., Duchowny, M. S., and Resnick, T. J. (1992). A safe and effective paradigm to functionally map the cortex in childhood. *J. Clin. Neurophysiol.* 9, 288-293. doi: 10.1097/00004691-199204010-00009

Jefferys, J. G. (1995). Nonsynaptic modulation of neuronal activity in the brain: electric currents and extracellular ions. *Physiol. Rev.* 75, 689-723. doi: 10.1152/physrev.1995.75.4.689

Jimbo, Y., Kawana, A., Parodi, P., and Torre, V. (2000). The dynamics of a neuronal culture of dissociated cortical neurons of neonatal rats. *Biol. Cybern.* 83, 1-20. doi: 10.1007/PL00007970

Jimbo, Y., Tateno, T., and Robinson, H. P. (1999). Simultaneous induction of pathway-specific potentiation and depression in networks of cortical neurons. *Biophys. J.* 76, 670-678. doi: 10.1016/S0006-3495(99)77234-6

Kamioka, H., Maeda, E., Jimbo, Y., Robinson, H. P., and Kawana, A. (1996). Spontaneous periodic synchronized bursting during formation of mature patterns of connections in cortical cultures. *Neurosci. Lett.* 206, 109-112. doi: 10.1016/S0304-3940(96)12448-4

Khambhati, A. N., Davis, K. A., Oommen, B. S., Chen, S. H., Lucas, T. H., Litt, B., et al. (2015). Dynamic network drivers of seizure generation, propagation and termination in human neocortical epilepsy. *PLoS Comput. Biol.* 11:e1004608. doi: 10.1371/journal.pcbi.1004608

Kilgore, K. L., and Bhadra, N. (2004). Nerve conduction block utilising high-frequency alternating current. *Med. Biol. Eng. Comput.* 42, 394-406. doi: 10.1007/BF02344716

Kim, D. H., Kim, Y. S., Amsden, J., Panilaitis, B., Kaplan, D. L., Omenetto, F. G., et al. (2009). Silicon electronics on silk as a path to bioresorbable, implantable devices. *Appl. Phys. Lett.* 95:133701. doi: 10.1063/1.3238552

Kim, D. H., Viventi, J., Amsden, J. J., Xiao, J., Vigeland, L., Kim, Y. S., et al. (2010). Dissolvable films of silk fibroin for ultrathin conformal bio-integrated electronics. *Nat. Mater* 9, 511-517. doi: 10.1038/nmat2745

Kirkby, L. A., Sack, G. S., Firl, A., and Feller, M. B. (2013). A role for correlated spontaneous activity in the assembly of neural circuits. *Neuron* 80, 1129-1144. doi: 10.1016/j.neuron.2013.10.030

Kryukov, A. K., Petrov, V. S., Averyanova, L. S., Osipov, G. V., Chen, W., Drugova, O., et al. (2008). Synchronization phenomena in mixed media of passive, excitable, and oscillatory cells. *Chaos* 18:037129. doi: 10.1063/1.2956985

Kwan, A. C. (2008). What can population calcium imaging tell us about neural circuits? *J. Neurophysiol.* 100, 2977-2980. doi: 10.1152/jn.91037.2008

Lafon, B., Rahman, A, Bikson, M., and Parra, L. C. (2017). Direct current stimulation alters neuronal input/output function. *Brain Stimul.* 10, 36-45. doi: 10.1016/j.brs.2016.08.014

Lancichinetti, A., and Fortunato, S. (2012). Consensus clustering in complex networks. *Sci. Rep.* 2:336. doi: 10.1038/srep00336

Larson, J., Wong, D., and Lynch, G. (1986). Patterned stimulation at the theta frequency is optimal for the induction of hippocampal long-term potentiation. *Brain Res.* 368, 347-350. doi: 10.1016/0006-8993(86)90579-2

Leondopulos, S. S., Boehler, M. D., Wheeler, B. C., and Brewer, G. J. (2012). Chronic stimulation of cultured neuronal networks boosts low-frequency oscillatory activity at theta and gamma with spikes phase-locked to gamma frequencies. *J. Neural Eng.* 9, 026015. doi: 10.1088/1741-2560/9/2/026015

Luhmann, H. J., Sinning, A., Yang, J. W., Reyes-Puerta, V., Stuttgen, M. C., Kirischuk, S., et al. (2016). Spontaneous neuronal activity in developing neocortical networks: from single cells to large-scale interactions. *Front. Neural Circ.* 10:40. doi: 10.3389/fncir.2016.00040

Maeda, E., Robinson, H. P., and Kawana, A. (1995). The mechanisms of generation and propagation of synchronized bursting in developing networks of cortical neurons. *J. Neurosci.* 15, 6834-6845. doi: 10.1523/JNEUROSCI.15-10-06834.1995

Malenka, R. C., and Bear, M. F. (2004). LTP and LTD: an embarrassment of riches. *Neuron* 44, 5-21. doi: 10.1016/j.neuron.2004.09.012

Manyakov, N. V., and Van Hulle, M. M. (2008). Synchronization in monkey visual cortex analyzed with an information-theoretic measure. *Chaos* 18:037130. doi: 10.1063/1.2949928

Marom, S., and Shahaf, G. (2002). Development, learning and memory in large random networks of cortical neurons: lessons beyond anatomy. *Q. Rev. Biophys.* 35, 63-87. doi: 10.1017/S0033583501003742

Mathie, A., Kennard, L. E., and Veale, E. L. (2003). Neuronal ion channels and their sensitivity to extremely low frequency weak electric field effects. *Radiat. Prot. Dosim.* 106, 311-316. doi: 10.1093/oxfordjournalsspd.a006365

McIntyre, C. C., and Grill, W. M. (2002). Extracellular stimulation of central neurons: influence of stimulus waveform and frequency on neuronal output. *J. Neurophysiol.* 88, 1592-1604. doi: 10.1152/jn.2002.88.4.1592

Morin, F. O., Takamura, Y., and Tamiya, E. (2005). Investigating neuronal activity with planar microelectrode arrays: achievements and new perspectives. *J. Biosci. Bioeng.* 100, 131-143. doi: 10.1263/jbb.100.131

Newman, M. E. J. (2010). *Networks: An Introduction.* New York, N.Y.: Oxford University Press. doi: 10.1093/acprof:oso/9780199206650.001.0001

O'Brien, R. J., Kamboj, S., Ehlers, M. D., Rosen, K. R., Fischbach, G. D., and Huganir, R. L. (1998). Activity-dependent modulation of synaptic AMPA receptor accumulation. *Neuron* 21, 1067-1078. doi: 10.1016/S0896-6273(00)80624-8

O'Keefe, J., and Recce, M. L. (1993). Phase relationship between hippocampal place units and the EEG theta rhythm. *Hippocampus* 3, 317-330. doi: 10.1002/hipo.450030307

Opitz, T., De Lima, A. D., and Voigt, T. (2002). Spontaneous development of synchronous oscillatory activity during maturation of cortical networks in vitro. *J. Neurophysiol.* 88, 2196-2206. doi: 10.1152/jn.00316.2002

Park, J., Zhu, H., O'sullivan, S., Ogunnaike, B. A., Weaver, D. R., Schwaber, J. S., et al. (2016). Single-cell transcriptional analysis reveals novel neuronal phenotypes and interaction networks involved in the central circadian clock. *Front. Neurosci.* 10:481. doi: 10.3389/fnins.2016.00481

Parodi, P., Jimbo, Y., Kawana, A., Macri, D., and Torre, V. (1998). Segmentation of the response of a neuronal network into clusters with similar activity. *Biosystems* 48, 171-178. doi: 10.1016/50303-2647(98)00063-X Radman, T., Ramos, R. L., Brumberg, J. C., and Bikson, M. (2009). Role of cortical cell type and morphology in subthreshold and suprathreshold uniform electric field stimulation in vitro. *Brain Stimul.* 2, 215-228, 228.e1-e3. doi: 10.1016/j.brs.2009.03.007

Rebola, N., Srikumar, B. N., and Mulle, C. (2010). Activity-dependent synaptic plasticity of NMDA receptors. *J. Physiol.* 588, 93-99. doi: 10.1113/jphysiol.2009.179382

Robinson, H. P., Kawahara, M., Jimbo, Y., Torimitsu, K., Kuroda, Y., and Kawana, A. (1993). Periodic synchronized bursting and intracellular calcium transients elicited by low magnesium in cultured cortical neurons. *J. Neurophysiol.* 70, 1606-1616. doi: 10.1152/jn.1993.70.4.1606

Ross, B., Jamali, S., Miyazaki, T., and Fujioka, T. (2013). Synchronization of beta and gamma oscillations in the somatosensory evoked neuromagnetic steady-state response. *Exp. Neurol.* 245, 40-51. doi: 10.1016/j.expneurol.2012.08.019

Shahaf, G., and Marom, S. (2001). Learning in networks of cortical neurons. *J. Neurosci.* 21, 8782-8788. doi: 10.1523/JNEUROSCI.21-22-08782.2001

Singer, W. (1999). Neuronal synchrony: a versatile code for the definition of relations? *Neuron* 24, 111-125. doi: 10.1016/S0896-6273(00)80821-1

Staubli, U., Scafidi, J., and Chun, D. (1999). GABAB receptor antagonism: facilitatory effects on memory parallel those on LTP induced by TBS but not HFS. *J. Neurosci.* 19, 4609-4615. doi: 10.1523/JNEUROSCI.19-11-04609.1999

Sun, J. J., Kilb, W., and Luhmann, H. J. (2010). Self-organization of repetitive spike patterns in developing neuronal networks in vitro. *Eur. J. Neurosci.* 32, 1289-1299. doi: 10.1111/j.1460-9568.2010.07383.x Tagawa, Y., Mizuno, H., and Hirano, T. (2008). Activity-dependent development of interhemispheric connections in the visual cortex. *Rev. Neurosci.* 19, 19-28. doi: 10.1515/REVNEURO.2008.19.1.19

Tan, H., Pogosyan, A., Anzak, A., Ashkan, K., Bogdanovic, M., Green, A. L., et al. (2013). Complementary roles of different oscillatory activities in the subthalamic nucleus in coding motor effort in Parkinsonism. *Exp. Neurol.* 248, 187-195. doi: 10.1016/j.expneurol.2013.06.010

Tang-Schomer, M. D., Davies, P., Graziano, D., Thurber, A. E., and Kaplan, D. L. (2014a). Neural circuits with long-distance axon tracts for determining functional connectivity. *J. Neurosci. Methods* 222, 82-90. doi: 10.1016/j.jneumeth.2013.10.014

Tang-Schomer, M. D., Hu, X., Tupaj, M., Tien, L. W., Whalen, M., Omenetto, F., et al. (2014b). Film-based implants for supporting neuron-electrode integrated interfaces for the brain. *Adv. Funct. Mater* 24, 1938-1948. doi: 10.1002/adfm.201303196

Tang-Schomer, M. D., White, J. D., Tien, L. W., Schmitt, L. I., Valentin, T. M., Graziano, D. J., et al. (2014c). Bioengineered functional brain-like cortical tissue. *Proc. Natl. Acad. Sci. U.S.A.* 111, 13811-13816. doi: 10.1073/pnas.1324214111

Tateno, T., and Jimbo, Y. (1999). Activity-dependent enhancement in the reliability of correlated spike timings in cultured cortical neurons. *Biol. Cybern.* 80, 45-55. doi: 10.1007/s004220050503

Tateno, T., Kawana, A., and Jimbo, Y. (2002). Analytical characterization of spontaneous firing in networks of developing rat cultured cortical neurons. *Phys. Rev. E Stat. Nonlin. Soft Matter Phys.* 65:051924. doi: 10.1103/PhysRevE.65.051924

Tien, L. W., Wu, F., Tang-Schomer, M. D., Yoon, E., Omenetto, F. G., and Kaplan, D. L. (2013). Silk as a multifunctional biomaterial substrate for reduced glial scarring around brain-penetrating electrodes. *Adv. Funct. Mater* 23, 3185-3193. doi: 10.1002/adfm.201203716

Uhlhaas, P. J., and Singer, W. (2010). Abnormal neural oscillations and synchrony in schizophrenia. *Nat. Rev. Neurosci.* 11, 100-113. doi: 10.1038/nrn2774

Wagenaar, D. A., Madhavan, R., Pine, J., and Potter, S. M. (2005). Controlling bursting in cortical cultures with closed-loop multi-electrode stimulation. *J. Neurosci.* 25, 680-688. doi: 10.1523/JNEUROSCI.4209-04.2005

Wagenaar, D. A., Pine, J., and Potter, S. M. (2004). Effective parameters for stimulation of dissociated cultures using multi-electrode arrays. *J. Neurosci. Methods* 138, 27-37. doi: 10.1016/j.jneumeth.2004.03.005

Wagner, T., Valero-Cabre, A., and Pascual-Leone, A. (2007). Noninvasive human brain stimulation. *Annu. Rev. Biomed. Eng.* 9, 527-565. doi: 10.1146/annurev.bioeng.9.061206.133100

Watts, D. J., and Strogatz, S. H. (1998). Collective dynamics of 'small-world' networks. *Nature* 393, 440-442. doi: 10.1038/30918

Yaffe, R. B., Borger, P., Megevand, P., Groppe, D. M., Kramer, M. A., Chu, C. J., et al. (2015). Physiology of functional and effective networks in epilepsy. *Clin. Neurophysiol.* 126, 227-236. doi: 10.1016/j.clinph.2014.09.009

Yi, G. S., Wang, J., Deng, B., and Wei, X. L. (2017). Morphology controls how hippocampal CA1 pyramidal neuron responds to uniform electric fields: a biophysical modeling study. *Sci. Rep.* 7:3210. doi: 10.1038/s41598-017-03547-6

Yoo, S. S., Teh, E. K., Blinder, R. A., and Jolesz, F. A. (2004). Modulation of cerebellar activities by acupuncture stimulation: evidence from fMRI study. *Neuroimage* 22, 932-940. doi: 10.1016/j.neuroimage.2004.02.017

Yu, H., Liu, J., Cai, L., Wang, J., Cao, Y., and Hao, C. (2017). Functional brain networks in healthy subjects under acupuncture stimulation: an EEG study based on nonlinear synchronization likelihood analysis. *Phys. A Statist. Mech. Appl.* 468, 566-577. doi: 10.1016/j.physa.2016.10.068

Yu, H., Wang, J., Deng, B., Wei, X., Che, Y., Wong, Y. K., et al. (2012). Adaptive backstepping sliding mode control for chaos synchronization of two coupled neurons in the external electrical stimulation. *Commun. Nonlin. Sci. Numer. Simul.* 17, 1344-1354. doi: 10.1016/j.cnsns.2011.07.009

Yu, H., Wang, J., Deng, B., Wei, X., Wong, Y. K., Chan, W. L., et al. (2011a). Chaotic phase synchronization in small-world networks of bursting neurons. *Chaos* 21:013127. doi: 10.1063/1.3565027

Yu, H., Wang, J., Liu, Q., Wen, J., Deng, B., and Wei, X. (2011b). Chaotic phase synchronization in a modular neuronal network of small-world subnetworks. *Chaos* 21:043125. doi: 10.1063/1.3660327

Yu, H., Wang, J., Liu, Q., Deng, B., and Wei, X. (2013). Delayed feedback control of bursting synchronization in small-world neuronal networks. *Neurocomputing* 99, 178-187. doi: 10.1016/j.neucom.2012.03.019

Yu, H., Wu, X., Cai, L., Deng, B., and Wang, J. (2018). Modulation of spectral power and functional connectivity in human brain by acupuncture stimulation. *IEEE Trans. Neural. Syst. Rehabil. Eng.* 26, 977-986. doi: 10.1109/TNSRE.2018.2828143

Zhang, L. I., and Poo, M. M. (2001). Electrical activity and development of neural circuits. *Nat. Neurosci.* 4(Suppl.), 1207-1214. doi: 10.1038/nn753

Aurand, E. R., Wagner, J., Lanning, C., Bjugstad, K. B., 2012. Building biocompatible hydrogels for tissue engineering of the brain and spinal cord. J. Funct. Biomater. 3, 839-863.

Bakkum, D. J., Chao, Z. C., Potter, S. M., 2008. Spatiotemporal electrical stimuli shape behavior of an embodied cortical network in a goal-directed learning task. J. Neural Eng. 5, 310-323.

Balkowiec, A., Katz, D. M., 2002. Cellular mechanisms regulating activity-dependent release of native brain-derived neurotrophic factor from hippocampal neurons. J. Neurosci. 22, 10399-10407.

Barros, C. S., Franco, S. J., Muller, U., 2011. Extracellular matrix: functions in the nervous system. Cold Spring Harb Perspect. Biol. 3, a005108.

Borgens, R. B., Shi, R., 1995. Uncoupling histogenesis from morphogenesis in the vertebrate embryo by collapse of the transneural tube potential. Dev. Dyn. 203, 456-467.

Borgens, R. B., Blight, A. R., Murphy, D. J., Stewart, L., 1986. Transected dorsal column axons within the guinea pig spinal cord regenerate in the presence of an applied electric field. J. Comp. Neurol. 250, 168-180.

Borgens, R. B., Toombs, J. P., Breur, G., Widmer, W. R., Waters, D., Harbath, A. M., March, P., Adams, L. G., 1999. An imposed oscillating electrical field improves the recovery of function in neurologically complete paraplegic dogs. J. Neurotrauma 16, 639-657.

Carballo-Molina, O. A., Velasco, I., 2015. Hydrogels as scaffolds and delivery systems to enhance axonal regeneration after injuries. Front. Cell. Neurosci. 9, 13.

Chao, M. V., 2003. Neurotrophins and their receptors: a convergence point for many signalling pathways. Nat. Rev. Neurosci. 4, 299-309.

Chwalek, K., Tang-Schomer, M. D., Omenetto, F. G., Kaplan, D. L., 2015. In vitro bioengineered model of cortical brain tissue. Nat. Protoc. 10, 1362-1373.

Davenport, R. W., McCaig, C. D., 1993. Hippocampal growth cone responses to focally applied electric fields. J. Neurobiol. 24, 89-100.

Dodd, J., Jessell, T. M., 1988. Axon guidance and the patterning of neuronal projections in vertebrates. Science 242, 692-699.

Gabriel, S., Lau, R. W., Gabriel, C., 1996. The dielectric properties of biological tissues: II. Measurements in the frequency range 10 Hz to 20 GHz. Phys. Med. Biol. 41, 2251-2269.

Graves, M. S., Hassell, T., Beier, B. L., Albors, G. O., Irazoqui, P. P., 2011. Electrically mediated neuronal guidance with applied alternating current electric fields. Ann. Biomed. Eng. 39, 1759-1767.

Hilton, B. J., Bradke, F., 2017. Can injured adult CNS axons regenerate by recapitulating development? Development 144, 3417-3429.

Hinkle, L., McCaig, C. D., Robinson, K. R., 1981. The direction of growth of differentiating neurones and myoblasts from frog embryos in an applied electric field. J. Physiol. 314, 121-135.

Hoffman-Kim, D., Mitchel, J. A., Bellamkonda, R. V., 2010. Topography, cell response, and nerve regeneration. Annu. Rev. Biomed. Eng. 12, 203-231.

Ingvar, S., 1920. Reaction of cells to the galvanic current in tissue cultures. Proc Soc Exp Biol Med. 17, 198-199.

Jaffe, L. F., Poo, M. M., 1979. Neurites grow faster towards the cathode than the anode in a steady field. J. Exp. Zool. 209, 115-128.

Jefferys, J. G., 1995. Nonsynaptic modulation of neuronal activity in the brain: electric currents and extracellular ions. Physiol. Rev. 75, 689-723.

Jin, G., Yang, G. H., Kim, G., 2015. Tissue engineering bioreactor systems for applying physical and electrical stimulations to cells. J. Biomed. Mater. Res. B. Appl. Biomater. 103, 935-948.

Koser, D. E., Thompson, A. J., Foster, S. K., Dwivedy, A., Pillai, E. K., Sheridan, G. K., Svoboda, H., Viana, M., Costa, L. D., Guck, J., Holt, C. E., Franze, K., 2016. Mechanosensing is critical for axon growth in the developing brain. Nat. Neurosci. 19, 1592-1598.

Lancaster, M. A., Renner, M., Martin, C. A., Wenzel, D., Bicknell, L. S., Hurles, M. E., Homfray, T., Penninger, J. M., Jackson, A. P., Knoblich, J. A., 2013. Cerebral organoids model human brain development and microcephaly. Nature 501, 373-379.

Leondopulos, S. S., Boehler, M. D., Wheeler, B. C., Brewer, G. J., 2012. Chronic stimulation of cultured neuronal networks boosts low-frequency oscillatory activity at theta and gamma with spikes phase-locked to gamma frequencies. J. Neural Eng. 9, 026015-2560/9/2/026015. Epub 2012 Feb. 23.

McCaig, C. D., 1986. Electric fields, contact guidance and the direction of nerve growth. J. Embryol. Exp. Morphol. 94, 245-255.

McCaig, C. D., Rajnicek, A. M., 1991. Electrical fields, nerve growth and nerve regeneration. Exp. Physiol. 76, 473-494.

Myers, J. P., Santiago-Medina, M., Gomez, T. M., 2011. Regulation of axonal outgrowth and pathfinding by integrin-ECM interactions. Dev. Neurobiol. 71, 901-923.

Pan, L., Borgens, R. B., 2012. Strict perpendicular orientation of neural crest-derived neurons in vitro is dependent on an extracellular gradient of voltage. J. Neurosci. Res. 90, 1335-1346.

Pan, L., Alagapan, S., Franca, E., Leondopulos, S. S., DeMarse, T. B., Brewer, G. J., Wheeler, B. C., 2015. An in vitro method to manipulate the direction and functional strength between neural populations. Front. Neural Circuits 9, 32.

Patel, N., Poo, M. M., 1982. Orientation of neurite growth by extracellular electric fields. J. Neurosci. 2, 483-496.

Patel, N. B., Poo, M. M., 1984. Perturbation of the direction of neurite growth by pulsed and focal electric fields. J. Neurosci. 4, 2939-2947.

Rajnicek, A. M., Foubister, L. E., McCaig, C. D., 2006. Growth cone steering by a physiological electric field requires dynamic microtubules, microfilaments and Rac-mediated filopodial asymmetry. J. Cell. Sci. 119, 1736-1745.

Rajnicek, A. M., Gow, N. A., McCaig, C. D., 1992. Electric field-induced orientation of rat hippocampal neurones in vitro. Exp. Physiol. 77, 229-232.

Rogers, S. L., Letourneau, P. C., Palm, S. L., McCarthy, J., Furcht, L. T., 1983. Neurite extension by peripheral and central nervous system neurons in response to substratum-bound fibronectin and laminin. Dev. Biol. 98, 212-220.

Schubert, D., 1992. Collaborative interactions between growth factors and the extracellular matrix. Trends Cell Biol. 2, 63-66.

Shapiro, S., Borgens, R., Pascuzzi, R., Roos, K., Groff, M., Purvines, S., Rodgers, R. B., Hagy, S., Nelson, P., 2005. Oscillating field stimulation for complete spinal cord injury in humans: a phase 1 trial. J. Neurosurg. Spine 2, 3-10.

Shi, R., Borgens, R. B., 1995. Three-dimensional gradients of voltage during development of the nervous system as invisible coordinates for the establishment of embryonic pattern. Dev. Dyn. 202, 101-114.

Sood, D., Chwalek, K., Stuntz, E., Pouli, D., Du, C., Tang-Schomer, M. D., Georgakoudi, I., Black, L. D., Kaplan, D., Fetal Brain Extracellular Matrix Boosts Neuronal Network Formation in 3D Bioengineered Model of Cortical Brain Tissue.—ACS Biomater. Sci. Eng.,—131.

Tandon, N., Cannizzaro, C., Chao, P. H., Maidhof, R., Marsano, A., Au, H. T., Radisic, M., Vunjak-Novakovic, G., 2009. Electrical stimulation systems for cardiac tissue engineering. Nat. Protoc. 4, 155-173.

Tang-Schomer, M. D., Davies, P., Graziano, D., Thurber, A. E., Kaplan, D. L., 2014a. Neural circuits with long-distance axon tracts for determining functional connectivity. J. Neurosci. Methods 222, 82-90.

Tang-Schomer, M. D., White, J. D., Tien, L. W., Schmitt, L. I., Valentin, T. M., Graziano, D. J., Hopkins, A. M., Omenetto, F. G., Haydon, P. G., Kaplan, D. L., 2014b. Bioengineered functional brain-like cortical tissue. Proc. Natl. Acad. Sci. U.S.A 111, 13811-13816.

Tang-Schomer, M. D., Hu, X., Hronik-Tupaj, M., Tien, L. W., Whalen, M. J., Omenetto, F. G., Kaplan, D. L., 2014c. Film-Based Implants for Supporting Neuron?Electrode Integrated Interfaces for The Brain. Advanced Functional Materials 24, 1938-1948.

Wood, M. D., Willits, R. K., 2009. Applied electric field enhances DRG neurite growth: influence of stimulation media, surface coating and growth supplements. J. Neural Eng. 6, 046003.

Yao, L., McCaig, C. D., Zhao, M., 2009. Electrical signals polarize neuronal organelles, direct neuron migration, and orient cell division. Hippocampus 19, 855-868.

Zoladz, J. A., Pilc, A., 2010. The effect of physical activity on the brain derived neurotrophic factor: from animal to human studies. J. Physiol. Pharmacol. 61, 533-541.

What is claimed is:

1. A method to modulate directed growth of neuronal axon comprising
   providing a 3D culture comprising
      a bioactive scaffold,
      a gel region adjacent to the scaffold,
      electrode pair at the interface of the scaffold and the gel region, wherein the electrode pair is spaced at least about 2 mm apart and spans a length of the interface, and
      a neuronal cell comprising a neuronal cell body, an axon, and neurites, wherein the neuronal cell body is immobilized on the scaffold and the axon and neurites have free movement and growth in the gel region,
   applying an alternating field electrical signal to the gel region in the 3D culture for a period of time to stimulate directed growth of the neuronal axon,
   wherein the alternating field electric signal is applied with the electrode pair spaced at least about 2 mm apart, and wherein the alternating field electric signal spans gel region.

2. The method of claim 1 wherein the 3D culture further comprises an extracellular matrix and growth factors.

3. The method of claim 1 wherein the alternating field is about 80 mV/mm at 0.5 Hz to 2 kHz.

4. The method of claim 1 wherein the alternating field electrical signal is 2 Hz and applied to the 3D culture for 7 days in the presence of LN, FN, BDNF or a combination thereof.

5. The method of claim 1, wherein the electrode pair is spaced at 2-4 mm, 4-6 mm, 6-8 mm or 8-10 mm apart.

6. The method of claim 1, further comprising the step of transplanting the cultured neuronal cell into a subject.

7. The method of claim 1 wherein the alternating field is 80 mV/mm at 2 Hz to 20 Hz.

8. The method of claim 1 wherein the alternating field is 80 mV/mm at about 0.5 Hz to 20 Hz and the alternating field electrical signal is applied to the 3D culture for less than 4 days.

9. The method of claim 1 wherein the directed growth of neuronal axon is assayed using beta III-tubulin immunostaining, confocal imaging, 3D neurite tracing or a combination thereof.

10. The method of claim 1 wherein the neuronal axon has a growth increase of 10-20%, 20-30%, 30-33%, 33-40%, 40-41%, 41-50%, or 50-60% in axon length as compared to neuronal axon without the alternating field electrical signal.

11. The method of claim 1 wherein the neuronal axon grows 600-700 μM, 700-800 M, 800-900 μM, 900-1000 μM, 1000-1100 μM, 1100-1200 μM, 1200-1300 μM, 1300-1400 μM, 1400-1500 μM, 1500-1600 μM, 1600-1700 μM, 1700-1800 μM, or 1800-1900 μM.

12. The method of claim 1 wherein the neuronal axon grows perpendicular to the electrode applying the alternating field having a field direction.

13. The method of claim 1 wherein the neuronal axon forms synapses with one or more neuronal cells in the culture.

14. The method of claim 1 wherein the alternating field is 10-500 mV/mm.

15. The method of claim 1, wherein the alternating field is applied at 0.2-0.5 Hz, 0.5-1 Hz, 1-10 Hz, 10-20 Hz, 20-30 Hz, 30-40 Hz, 40-50 Hz, 50-60 Hz, 60-80 Hz, 80-100 Hz, 100-120 Hz, 120-140 Hz, 140-160 Hz, 160-180 Hz, 180-200 Hz, or 200-2000 Hz.

16. The method of claim 1, wherein the neuronal axon grows between paired electrodes, in parallel to the field direction.

17. The method of claim 1, wherein the neuronal axon grows between paired electrodes, perpendicular to the electrodes.

18. The method of claim 1, wherein the 3D culture comprises a plurality of neuronal cells which interact to form multicellular neural aggregates.

19. The method of claim 1, wherein the 3D culture has a donut shape comprising a scaffold outer region and a center gel region.

* * * * *